(12) United States Patent
Miserez et al.

(10) Patent No.: US 12,037,418 B2
(45) Date of Patent: Jul. 16, 2024

(54) HYDROGEL-FORMING PEPTIDES, AND METHODS OF USE THEREOF

(71) Applicant: Nanyang Technological University, Singapore (SG)

(72) Inventors: Ali Gilles Tchenguise Miserez, Singapore (SG); Shu Hui Hiew, Singapore (SG); Chor Yong Tay, Singapore (SG); Jun Kit Wang, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 158 days.

(21) Appl. No.: 17/364,153

(22) Filed: Jun. 30, 2021

(65) Prior Publication Data

US 2022/0024979 A1 Jan. 27, 2022

(30) Foreign Application Priority Data

Jun. 30, 2020 (SG) .......................... 10202006312Q

(51) Int. Cl.
```
C07K 7/08      (2006.01)
A61K 35/17     (2015.01)
A61K 38/00     (2006.01)
A61L 27/22     (2006.01)
A61L 27/52     (2006.01)
A61L 27/54     (2006.01)
```

(52) U.S. Cl.
CPC ................ *C07K 7/08* (2013.01); *A61K 35/17* (2013.01); *A61L 27/227* (2013.01); *A61L 27/52* (2013.01); *A61L 27/54* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 2014/0271843 A1* | 9/2014 | Ma | ........................ | A61K 9/0024 424/463 |
| 2014/0302144 A1* | 10/2014 | Koutsopoulos | ...... | A61K 9/5015 514/7.7 |
| 2015/0274789 A1* | 10/2015 | Guerette | ................ | A61L 27/227 524/21 |
| 2017/0119892 A1* | 5/2017 | Brudno | ................. | A61K 9/0024 |

FOREIGN PATENT DOCUMENTS

| | | |
|---|---|---|
| WO | WO 2014062134 A9 | 4/2014 |
| WO | WO-2018070942 A1 * | 4/2018 |

OTHER PUBLICATIONS

J. Gen. Physiol. vol. 136 No. 6 585-592 (2010) (Year: 2010).*
Adessi and Soto, Current Medicinal Chemistry, 2002, 9, 963-978 (Year: 2002).*
Adams et al., "A new method for maintaining homogeneity during liquid-hydrogel transitions using low molecular weight hydrogelators," *Soft Matter* 5:1856-1862, 2009.
Ahearne, "Introduction to cell-hydrogel mechanosensing," *Interface Focus* 4:1-12, 2014.
Armen et al., "The role of α-, 310-, and π-helix in helix →coil transitions," *Protein Science* 12:1145-1157, 2003.
Bai et al., "Primary Structure Effects on Peptide Group Hydrogen Exchange," *Proteins: Structure, Function, and Genetics* 17:75-86, 1993.
Bakota et al., "Injectable Multidomain Peptide Nanofiber Hydrogel as a Delivery Agent for Stem Cell Secretome," *Biomacromolecules* 12:1651-1657, 2011.
Banwell et al., "Rational design and application of responsive a-helical peptide hydrogels," *Nature Materials* 8:596-600, 2009.
Bertolani et al., "Supramolecular amplification of amyloid self-assembly by iodination," *Nature Communications* 6:1-9, 2015.
Bussi, "Hamiltonian replica exchange in GROMACS: a flexible implementation," *Molecular Physics* 112(3-4):379-384, 2014.
Cao et al., "Elasticity in Physically Cross-Linked Amyloid Fibril Networks," *Physical Review Letters* 120:158103-1-158103-6, 2018.
Carrejo et al., "Multidomain Peptide Hydrogel Accelerates Healing of Full-Thickness Wounds in Diabetic Mice," *ACS Biomater. Sci. Eng.* 4:1386-1396, 2018.
Case et al., "The Amber Biomolecular Simulation Programs," *Journal of Computational Chemistry* 26(16):1668-1688, 2005.
Cierpicki et al., "Amide proton temperature coefficients as hydrogen bond indicators in proteins," *Journal of Biomolecular NMR* 21:249-261, 2001.
Clarke et al., "Tunable Pentapeptide Self-Assembled β-Sheet Hydrogels," *Angew. Chem. Int. Ed.* 57:7709-7713, 2018.
Cui et al., "Self-Assembly of Peptide Amphiphiles: From Molecules to Nanostructures to Biomaterials," *Pept. Sci.* 94(1):1-18, 2010.
De Brevern, "Extension of the classical classification of β-turns," *Scientific Reports* 6:1-15, 2016.
Ding et al., "From Soft Self-Healing Gels to Stiff Films in Suckerin-Based Materials Through Modulation of Crosslink Density and β-Sheet Content," *Adv. Mater.* 27:3953-3961, 2015.
Ding et al., "Squid suckerin microneedle arrays for tunable drug release," *J. Mater. Chem. B.* 5:8467-8478, 2017.
Dinjaski et al., "Recombinant protein blends: silk beyond natural design," *Current Opinion in Biotechnology* 39:1-7, 2016.
Discher et al., "Tissue Cells Feel and Respond to the Stiffness of Their Substrate," *Science* 310:1139-1143, Nov. 18, 2005.

(Continued)

*Primary Examiner* — Melissa L Fisher
*Assistant Examiner* — Joseph Fischer
(74) *Attorney, Agent, or Firm* — Seed IP Law Group LLP

(57) ABSTRACT

The present invention, as disclosed herein, provides an isolated peptide, and a composition or material comprising a hydrogel, for the delivery of an active agent. The hydrogel comprises one or more isolated peptides and an active agent encapsulated in the hydrogel. The hydrogel is at least partially in a β-sheet conformation. Further provided are a method for the encapsulation of an active agent in a hydrogel, a method for treating or diagnosing a condition or disease in a subject in need thereof.

20 Claims, 64 Drawing Sheets
Specification includes a Sequence Listing.

(56) References Cited

OTHER PUBLICATIONS

Dong et al., "A rapid crosslinking injectable hydrogel for stem cell delivery, from multifunctional hyperbranched polymers via RAFT homopolymerization of PEGDA," *Polym. Chem.* 6:6182-6192, 2015.
Engler et al., "Matrix Elasticity Directs Stem Cell Lineage Specification," *Cell* 126: 677-689, Aug. 25, 2006.
Essmann et al., "A smooth particle mesh Ewald method," *J. Chem. Phys.* 103(19):8577-8593, Nov. 15, 1995.
Fosgerau et al., "Peptide therapeutics: current status and future directions," *Drug Discovery Today* 20(1):122-128, Jan. 2015.
Frederix et al., "Exploring the sequence space for (tri-)peptide self-assembly to design and discover new hydrogels," *Nature Chemistry* 7:30-37, Jan. 2015.
Gardel et al., "Elastic Behavior of Cross-Linked and Bundled Actin Networks," *Science* 304:1301-1305, May 28, 2004.
Gonzalez et al., "Strong, Tough, Stretchable, and Self-Adhesive Hydrogels from Intrinsically Unstructured Proteins," *Adv. Mater.* 29:1604743, 2017. (8 pages).
Greenfield et al., "Tunable Mechanics of Peptide Nanofiber Gels," *Langmuir* 26(5):3641-3647, 2010.
Grishina et al., "Contributions of Tryptophan Side Chains to the Circular Dichroism of Globular Proteins: Exciton Couplets and Coupled Oscillators," *Faraday Discuss.* 99:245-262, 1994.
Guerette et al., "Nanoconfined β-Sheets Mechanically Reinforce the Supra-Biomolecular Network of Robust Squid Sucker Ring Teeth," *ACSNano* 8(7):7170-7179, 2014.
Hauser et al., "Natural tri- to hexapeptides self-assemble in water to amyloid β-type fiber aggregates by unexpected α-helical intermediate structures," *PNAS* 108(4):1361-1366, Jan. 25, 2011.
Hedegaard et al., "Fluorophore labeling of a cell-penetrating peptide significantly alters the mode and degree of biomembrane interaction," *Scientific Reports* (8)6327:1-14, 2018.
Hiew et al., "A Short Peptide Hydrogel with High Stiffness Induced by 3 10-Helices to β-Sheet Transition in Water," *Adv. Sci.* 6:1901173, 2019. (11 pages).
Hiew et al., "Modular peptides from the thermoplastic squid sucker ring teeth form amyloid-like cross-β supramolecular networks," *Acta Biomaterialia* 46:41-54, 2016.
Hiew et al., "Squid Sucker Ring Teeth: Multiscale Structure-Property Relationships, Sequencing, and Protein Engineering of a Thermoplastic Biopolymer," *ACS Biomater. Sci. Eng.* 3:680-693, 2017.
Huang et al., "CHARMM36 All-Atom Additive Protein Force Field: Validation Based on Comparison to NMR Data," *Journal of Computational Chemistry* 34: 2135-2145, 2013.
Hwang et al., "Matrix Topographical Cue-Mediated Myogenic Differentiation of Human Embryonic Stem Cell Derivatives," *Polymers* 9:1-13, 2017.
Jorgensen et al., "Comparison of simple potential functions for simulating liquid water," *J. Chem. Phys.* 79(2):926-935, Jul. 15, 1983.
Khalily et al., "Tuning viscoelastic properties of supramolecular peptide gels via dynamic covalent crosslinking," *Org. Biomol. Chem.* 13:1983-1987, 2015.
Khan et al., "Gauging a Hydrocarbon Ruler by an Intrinsic Exciton Probe," *Biochemistry* 46:4565-4579, 2007.
Kim et al., "Current Understanding of Stem Cell and Secretome Therapies in Liver Diseases," *Tissue Eng Regen Med* 14(6):653-665, 2017.
Kong et al., "Fourier Transform Infrared Spectroscopic Analysis of Protein Secondary Structures," *Acta Biochimica et Biophysica Sinica* 39(8):549-559, 2007.
Kumar et al., "Supramolecular propensity of suckerin proteins is driven by β-sheets and aromatic interactions as revealed by solution NMR," *Biomater. Sci.* 6:2440-2447, 2018.
Kuwata et al., "NMR-detected hydrogen exchange and molecular dynamics simulations provide structural insight into fibril formation of prion protein fragment 106-126," *PNAS* 100(25):14790-14795, Dec. 9, 2003.
Kwon et al., "Recent advances in stem cell therapeutics and tissue engineering strategies," *Biomaterials Research* 22(36):1-8, 2018.
Laskowski et al., "Procheck: a program to check the stereochemicai quality of protein structures.," *J. Appl. Cryst.* 26:283-291, 1993.
Latza et al., "Multi-scale thermal stability of a hard thermoplastic protein-based material," *Nature Communications* 6:1-8, Sep. 21, 2015.
Lee et al., "Investigation of wound healing process guided by nano-scale topographic patterns integrated within a microfluidic system," *PLoS ONE* 13(7):1-16, Jul. 26, 2018.
Lee et al., "NMRFAM-SPARKY: enhanced software for biomolecular NMR spectroscopy," *Bioinformatics* 31(8):1325-1327, 2015.
Li et al., "Designing hydrogels for controlled drug delivery," *Nature Reviews Materials* 1:1-17, Dec. 2016.
Loo et al., "Peptide Bioink: Self-Assembling Nanofibrous Scaffolds for Three-Dimensional Organotypic Cultures," *Nano. Lett.* 15:6919-6925, Jul. 2015.
Loo et al., "Ultrashort peptide nanofibrous hydrogels for the acceleration of healing of burn wounds," *Biomaterials* 35:4805-4814, 2014.
MacKintosh et al., "Elasticity of Semiflexible Biopolymer Networks," *Physical Review Letters* 75(24):4425-4429, Dec. 11, 1995.
Madrigal et al., "A review of therapeutic effects of mesenchymal stem cell secretions and induction of secretory modification by different culture methods," *Journal of Translational Medicine* 12(260):1-14, 2014.
Marmaras et al., "Topography-mediated apical guidance in epidermal wound healing," *Soft Matter* 8:6922-6930, 2012.
Marusina et al., "Tunable hydrogels for mesenchymal stem cell delivery: Integrin-induced transcriptome alterations and hydrogel optimization for human wound healing," *Stem Cells* 38:231-245, 2020.
Mezzenga et al., "The self-assembly, aggregation and phase transitions of food protein systems in one, two and three dimensions," *Rep. Prog. Phys.* 76:1-43, 2013.
Millhauser et al., "Estimating the Relative Populations of 3 10-Helix and α-Helix in Ala-rich Peptides: A Hydrogen Exchange and High Field NMR Study," *J. Mol. Biol.* 267:963-974, 1997.
Monera et al., "Relationship of Sidechain Hydrophobicity and α-Helical Propensity on the Stability of the Single-stranded Amphipathic α-Helix," *Journal of Peptide Science* 1:319-329, 1995.
Myers et al., "Corrections: On the sequencing and assembly of the human genome," *PNAS* 99:4145-4146, 2002.
Nagai et al., "The mechanical stimulation of cells in 3D culture within a self-assembling peptide hydrogel," *Biomaterials* 33:1044-1051, 2012.
Newcomb et al., "Advances in cryogenic transmission electron microscopy for the characterization of dynamic self-assembling nanostructures," *Current Opinion in Colloid & Interface Science* 17:350-359, 2012.
Nguyen et al., "Bioactive factor delivery strategies from engineered polymer hydrogels for therapeutic medicine," *Progress in Polymer Science* 39:1235-1265, 2014.
Ozbas et al., "Salt-Triggered Peptide Folding and Consequent Self-Assembly into Hydrogels with Tunable Modulus," *Macromolecules* 37:7331-7337, 2004.
Perez et al., "The Powerful Functions of Peptide-Based Bioactive Matrices for Regenerative Medicine," *Annals of Biomedical Engineering* 43(3):501-514, Mar. 2015.
Perrone et al., "The use of silk-based devices for fracture fixation," *Nat. Commun.* 5:1-9, Mar. 2014.
Ping et al., "Supramolecular β-Sheets Stabilized Protein Nanocarriers for Drug Delivery and Gene Transfection," *ACS Nano* 11:4528-4541, 2017.
Robert et al., "The skin regeneration potential of a pro-angiogenic secretome from human skin-derived multipotent stromal cells," *Journal of Tissue Engineering* 10:1-10, 2019.
Rodriguez et al., "Silk based bioinks for soft tissue reconstruction using 3-dimensional (3D) printing with in vitro and in vivo assessments," *Biomaterials* 117:105-115, 2017.
Ryckaert et al., "Numerical Integration of the Cartesian Equations of Motion of a System with Constraints: Molecular Dynamics of n-Alkanes," *Journal of Computational Physics* 23:327-341, 1977.

(56) References Cited

OTHER PUBLICATIONS

Sahoo et al., "Injectable network biomaterials via molecular or colloidal self-assembly," *Advanced Drug Delivery Reviews 127*:185-207, 2018.

Sato et al., "Peptide supramolecular materials for therapeutics," *Chem. Soc. Rev. 47*:7539-7551, 2018.

Seow et al., "Transparent crosslinked ultrashort peptide hydrogel dressing with high shape-fidelity accelerates healing of full-thickness excision wounds," *Scientific Reports 6*:1-12, 2016.

Sereda et al., "Reversed-phase chromatography of synthetic amphipathic α-helical peptides as a model for ligand/receptor interactions Effect of changing hydrophobic environment on the relative hydrophilicity / hydrophobicity of amino acid side-chains," *Journal of Chromatography A 676*:139-153, 1994.

Singh et al., "Amyloid Formation from an α-Helix Peptide Bundle Is Seeded by 310-Helix Aggregates," *Chem. Eur. J. 17*:151-160, 2011.

Slaughter et al., "Hydrogels in Regenerative Medicine," *Adv. Mater. 21*:3307-3329, 2009.

Souza et al., "Nanostructured Antigen-Responsive Hydrogels Based on Peptides for *Leishmaniasis* Detection," *J. Braz. Chem. Soc. 28*(9):1619-1629, 2017.

Stephanopoulos et al., "Self-assembly for the synthesis of functional biomaterials," *Acta Materialia 61*:912-930, 2013.

Storm et al., "Nonlinear elasticity in biological gels," *Nature 435*:191-194, May 12, 2005.

Tay et al., "Micro-/Nano-engineered Cellular Responses for Soft Tissue Engineering and Biomedical Applications," *small 7*(10):1361-1378, 2011.

Tokareva et al., "Recombinant DNA production of spider silk proteins," *Microbial Biotechnology 6*(6):651-663, 2013.

Trappmann et al., "Extracellular-matrix tethering regulates stem-cell fate," *Nature Materials 11*:642-649, Jul. 2012.

Tsou et al., "Hydrogel as a bioactive material to regulate stem cell fate," *Bioactive Materials 1*:39-55, 2016.

Vass et al., "Vibrational Spectroscopic Detection of Beta- and Gamma-Turns in Synthetic and Natural Peptides and Proteins," *Chem. Rev. 103*:1917-1954, 2003.

Wang et al., "Adaptable Hydrogel Networks with Reversible Linkages for Tissue Engineering," *Adv. Mater. 27*:3717-3736, 2015.

Waters et al., "Stem cell secretome-rich nanoclay hydrogel: a dual action therapy for cardiovascular regeneration," *Nanoscale 8*:7371-7376, 2016.

Waters et al., "Stem cell-inspired secretome-rich injectable hydrogel to repair injured cardiac tissue," *Acta Biomaterialia 69*:95-106, 2018.

Williams, "Chapter 36: Hydrogels in Regenerative Medicine," *Principles of Regenerative Medicine, Third Edition*: 627-650, 2019.

Wilson et al., "Conformational Transitions in Model Silk Peptides," *Biophysical Journal 78*:2690-2701, May 2000.

Wishart et al., "The Chemical Shift Index: A Fast and Simple Method for the Assignment of Protein Secondary Structure through NMR Spectroscopy," *Biochemistry 31*:1647-1651, 1992.

Woody, "Aromatic Side-Chain Contributions to the Far Ultraviolet Circular Dichroism of Peptides and Proteins," *Biopolymers 17*:1451-1467, 1978.

Wu et al., "Geometry and Efficacy of Cross-Strand Trp/Trp, Trp/Tyr, and Tyr/Tyr Aromatic Interaction in a β-Hairpin Peptide," *Biochemistry 49*:4705-4714, 2010.

Yan et al., "Rheological properties of peptide-based hydrogels for biomedical and other applications," *Chem. Soc. Rev. 39*:3528-3540, 2010.

Yang et al., "Artificially Engineered Protein Polymers," *Annu. Rev. Chem. Biomol. Eng. 8*:549-575, 2017.

Yang et al., "Materials Stiffness-Dependent Redox Metabolic Reprogramming of Mesenchymal Stem Cells for Secretome-Based Therapeutic Angiogenesis," *Adv. Healthcare Mater. 8*:1-12, 2019.

Yang et al., "Obtaining information about protein secondary structures in aqueous solution using Fourier transform IR spectroscopy," *Nature Protocols 10*(3):382-396, 2015.

Yegappan et al., "Carrageenan based hydrogels for drug delivery, tissue engineering and wound healing," *Carbohydrate Polymers 198*:385-400, 2018.

Zhao et al., "Fabrication and physical and biological properties of fibrin gel derived from human plasma," *Biomed. Mater. 3*:1-9, 2008.

Zion Market Research, "Active Wound Care Market to Reach Value of USD 2,300 Million by 2024: Zion Market Research," New York, NY: Jul. 13, 2019. (7 pages).

* cited by examiner

| Assign-ment (%) | 20mM peptide incubation duration | | | | | | | | | | |
|---|---|---|---|---|---|---|---|---|---|---|---|
| | 0 h | 1 h | 2 h | 3 h | 4 h | 5 h | 6 h | 7 h | 8 h | 25 h | 50 h |
| β-sheet | 33.1 | 40.3 | 37.9 | 37.5 | 36.0 | 43.8 | 46.4 | 54.4 | 54.6 | 49.9 | 65.5 |
| Unordered | 15.0 | 13.7 | 14.6 | 13.7 | 18.3 | 11.8 | 13.4 | 6.1 | 8.1 | 11.2 | - |
| α-Helix | 14.3 | 14.7 | 14.1 | 15.2 | 13.1 | 13.4 | 9.7 | 13.5 | 11.2 | 14.3 | 16.4 |
| Turns or $3_{10}$ | 37.6 | 31.3 | 33.4 | 33.7 | 32.6 | 30.9 | 30.4 | 25.9 | 26.1 | 24.7 | 18.0 |

|  | GV8 monomer (solution NMR) | GV8 oligomer (solution NMR) | GV8 hydrogel (ssNMR) |
|---|---|---|---|
| Distance restraints | | | |
| Intraresidue ($|i-j|=0$) | 9 | 18 | 22 |
| Sequential ($|i-j|=1$) | 14 | 32 | 27 |
| Medium range ($2 \leq |i-j| \leq 4$) | 16 | 56 | 0 |
| Long range ($|i-j| \leq 5$) | 0 | 32 | 10 |
| Total NOE constraints (solution NMR) / dipolar contacts (ssNMR) | 39 | 138 | 59 |
| Distance restraints violations | | | |
| Number of violations | 9 | 51 | 33 |
| Maximum violation | $\leq 0.5$ | $\leq 0.5$ | $\leq 0.5$ |
| Average target function value | 4.49 | 34.36 | 17.37 |
| Deviation from mean structure | | | |
| Backbone atoms (Å) | 0.52 | 0.65 | 1.49 |
| Heavy atoms (Å) | 0.92 | 0.70 | 1.75 |
| Ramachandran plot for the mean structure | | | |
| % residues in the most favourable and additionally allowed regions | 100 | 100 | 85 |
| % residues in the generously allowed region | 0 | 0 | 15 |
| % residues in the disallowed region. | 0 | 0 | 0 |

FIG. 14

HYDROGEL-FORMING PEPTIDES, AND METHODS OF USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_579_SEQUENCE_LISTING.txt. The text file is 6.4 KB, was created on Jun. 28, 2021, and is being submitted electronically via EFS-Web.

CROSS-REFERENCE TO RELATED APPLICATION

This application claims the benefit of priority of Singapore Patent Application No. 10202006312Q filed Jun. 30, 2020, the contents of which being hereby incorporated by reference in its entirety for all purposes.

FIELD OF THE INVENTION

The present invention relates to hydrogel-forming peptides, in particular for the delivery of active agent(s) using hydrogels including the hydrogel-forming peptides, and methods of (active agent) encapsulation and administration using the hydrogel.

BACKGROUND OF THE INVENTION

Active wound management is defined as the application of biologically active agent(s) to a wound site. The global active wound care market is growing rapidly, due to increased government support in the research and development of wound care products, and the expected future increase in diabetic and geriatric populations. Thus, active wound management that shortens the wound healing and recovery process is required. According to Zion Market Research report (*Zion Market Res.* 2019), the market value for global active wound care was estimated to be at USD 950 million in 2017, and is expected to grow at a compound annual growth rate of around 13% between 2018 and 2024, generating up to USD 2,300 million by the end of 2024.

Peptide hydrogels are increasingly explored for biomedical applications such as wound healing patches (Y. Loo et al. *Biomater.* 2014, 35, 4805; N. C. Carrejo et al. *ACS Biomater. Sci. & Eng.* 2018, 4, 1386), cell culture scaffolds for tissue engineering (Y. Nagai et al. *Biomater.* 2012, 33, 1044), drug delivery vehicles (J. Y. Li et al. *Nat. Rev. Mater.* 2016, 1, 16071) or as substrates to study stem cell differentiation (B. Trappmann et al. *Nat. Mater.* 2012, 11, 642). Peptides are particularly attractive as building blocks for hydrogels because: (i) their chemical structure and poly-dispersity is fully controlled, (ii) they exhibit high biocompatibility (N. Stephanopoulos et al. *Acta. Mater.* 2013, 61, 912), and (iii) their degradation products (amino acids) are readily cleared or re-absorbed by metabolism (N. Stephanopoulos et al. *Acta. Mater.* 2013, 61, 912). In addition, bioactivity and functionality of the hydrogels can be achieved: for example, RGD peptides can be incorporated into the peptide sequence (H. G. Cui et al. *Biopoly.* 2010, 94, 1) to promote cell recognition, or the peptide can be chemically modified with fluorescent probes and dye reporters (S. F. Hedegaard et al. *Sci. Rep. UK.* 2018, 8, 6327), or with functional groups to promote subsequent crosslinking reactions (M. A. Gonzalez et al. *Adv. Mater.* 2017, 29, 1604743). Further, the ability to tune the gels' mechanical properties has become an increasingly important factor in the consideration of gel design (C. Q. Yan, *Chem. Soc. Rev.* 2010, 39, 3528). While some hydrogels employ crosslinking to vary the elastic properties (M. A. Khalily, *Org. Biomol. Chem.* 2015, 13, 1983), others can be altered by varying the amount of salt in the gelation buffer or by adjusting peptide concentration (Y. Loo et al. *Nano Left.* 2015, 15, 6919). Some peptides also employ organic solvents to trigger gelation or toxic chemicals for crosslinking, which is not ideal from a biocompatibility perspective (M. A. Khalily, *Org. Biomol. Chem.* 2015, 13, 1983; S. F. Souza J et al. *Brazil. Chem. Soc.* 2017, 28, 1619].

Recently, peptide hydrogels have been employed in regenerative medicine platforms, e.g. wound healing, by encapsulating living cells and/or therapeutic agents to promote the repair and recovery of damaged tissues (B. V. Slaughter et al. *Adv. Mater.* 2009, 21, 3307; D. F. Williams et al. *Prin. of Regen. Med.* (3rd Ed). 2019, 627). In cell-based therapies, mesenchymal stem cells (MSCs) are excellent therapeutic candidates due to their excellent self-renewal and differentiation potential, as well as good immune modulatory and pro-angiogenic functions which are beneficial for tissue regeneration (S. G. Kwon et al. *Biomater. Res.* 2018, 22, 36; M. J. Madrigal et al. *Transl. Med.* 2014, 12, 260). However, one of the common drawbacks of cell-based therapies is poor cell survivability in vivo. As such, various types of hydrogels have been designed, synthesized and functionalized to promote cell survivability, differentiation and the therapeutic efficacy of transplanted stem cells (Y. H. Tsou et al. *Bioact. Mater.* 2016, 1, 39; A. I. Marusina et al. *Stem Cells.* 2020, 38, 231; Y. Dong et al. *Poly. Chem.* 2015, 6, 6182). There is also evidence indicating that the stem cells could influence the host regenerative system via paracrine effects (D. Kim et al. *Tiss. Eng. Regen. Med.* 2017, 14, 653). Specifically, the totality of signaling molecules secreted by stem cells such as MSCs—also known as secretome— contain a broad repertoire of proteins (i.e. cytokines and growth factors) that have therapeutic benefits (H. Yang et al. *Adv. Healthcare Mater.* 2019, 8, 1900929), and the use of secretome encapsulated in hydrogel systems have gained increasing interest over the years as effective cell-free therapy approaches in the field of regenerative medicine.

Advancements in polymer and protein sciences have led to the development of various hydrogel-based delivery systems (J. Li et al. *Nat. Rev. Mater.* 2016, 1, 16071). In general, such systems should be biocompatible and processable under mild aqueous conditions to prevent the loss of the bioactivity of the encapsulated agent. Other features have also been incorporated to promote the regenerative process, such as bioactive domains (C. M Rubert Pérez et al. *Ann. Biomed Eng.* 2015, 43, 501; K. Sato et al. *Chem. Soc. Rev.* 2018, 47, 7539), tunable matrix stiffness (D. E. Clarke et al. *Angew. Chemie Int. Ed.* 2018, 57, 7709; B. Ozbas et al. *Macromol.* 2004, 37, 7331), chemical and physical cues to promote cell-matrix interactions, ease of self-assembly into a desired 3D shape (W. Y. Seow et al. *Sci. Reports.* 2016, 6, 32670), and patterned surfaces for contact-guided cell migration to the wound site (C. Y. Tay et al. *Small.* 2011, 7, 1361). Although various natural proteins have been explored as potential hydrogel materials, there are limitations to the approach, such as low production yields (O. Tokareva et al. *Micro. Biotech.* 2013, 6, 651) and harsh conditions to promote crosslinking or poor water solubility (G. S Perrone. *Nat. Comms.* 2014, 5, 3385; M. Rodriguez et al. *Biomater.* 2017, 117, 105)—which are highly protein-dependent.

Hydrogel-based delivery systems have also been employed for the delivery of secretome. The use of carrageenan (CG)-sulfated hydrophilic polysaccharides from red algae, and polyvinyl alcohol (PVA) hydrogels (R. Yegappan et al. *Carbohydrate Poly.* 2018, 198, 385) as carriers for conditioned media (CM) from multipotent stromal cells was recently reported (A. W. Robert et al. *J. Tiss. Eng.* 2019, 10, 2041731419833391), with both hydrogels performing subpar as compared to direct CM treatment for cutaneous wound healing and angiogenesis. The hydrogels also require complicated preparation procedures—CG hydrogels require heating, filtration, polymerization, while PVA hydrogels require heating and polymerization in a freeze-thaw cycle. In another delivery system, a nanocomposite hydrogel comprising gelatin methacrylate (GelMa) (R. Waters et al. *Nanoscale.* 2016, 8, 7371)/gelatin and Laponite® as a secretome-rich injectable hydrogel (R. Waters et al. *Acta Biomater.* 2018, 69, 95) was reported. Said hydrogel is shear-thinning, thus enabling precise injection and ease of secretome delivery to the wound site, and was reported to be used in the repair of injured cardiac tissue by promoting angiogenesis and reducing cardiac remodeling in rat models (R. Waters et al. *Acta Biomater.* 2018, 69, 95). However, constituents of the hydrogel (i.e. without secretome) have to be precisely mixed to achieve desired release properties. Further, the gelation of GelMA and Laponite® involves UV exposure for crosslinking (R. Waters et al. *Nanoscale.* 2016, 8, 7371). Exposing secretome to UV during the crosslinking process may subject the growth factors and cytokines in secretome to free radical attack and changes which result in the damage of secretomes' functions and efficacy. Since secretome consists of many components, it would be difficult to elucidate the effects of UV exposure on the various components in secretome. Multidomain peptides (MDPs) have also been reported to successfully load and deliver human embryonic stem cells secretome, such as $E_2(SL)_6$ $E_2$GRGDS (E. L Bakota et al. *Biomacromol.* 2011, 12, 1651), which forms a stable and nanofibrous hydrogel with a storage modulus (G') of an about 480 Pa in the presence of $Mg^{2+}$, and may be delivered by syringe due to its shear thinning property. However, the $E_2(SL)_6E_2$GRGDS MDPs are fragile, resulting in the reduction of the hydrogel retention time at the injection site and decreased secretome delivery duration. Further, the loading of secretome into the MDP requires a 24 h adsorption process as secretome diffuses through a permeable membrane setup which also does not allow for a desired amount of secretome to be loaded, or for the loading of higher concentrations of secretome—both of which may not be practical during production.

In recent years, there is a growing interest in short peptide (i.e. <10 amino acids) hydrogels as it allows for complete control of the sequence and structural chemistry down to the single amino acid level with a poly-dispersity index of 1 (N. Dinjaski et al. *Curr. Opi. Biotech.* 2016, 39, 1; H. Wang et al. *Adv. Mater.* 2015, 27, 3710; Y. J. Yang et al. *Rev. Chem. & Biomol. Eng.* 2017, 8, 549), and the peptides can be readily produced by solid phase peptide synthesis in relatively large scale. There is also growing evidence that designed short peptides can be processed into hydrogels (P. Frederix et al. *Nat. Chem.* 2015, 7, 30; C. A. E Hauser et al. *PNAS. USA.* 2011, 108, 1361) under mild conditions with tunable physico-chemical properties (which is of critical importance for biomedical applications) and excellent biocompatibility both in vitro and in vivo (K. Fosgerau et al. *Drug Disc. Today.* 2015, 20, 122). In many cases, such short peptide-based hydrogels are assembled from β-sheets, β-hairpins, or coiled-coil α-helices (E. F. Banwell et al. *Nat. Mater.* 2009, 8, 596; J. K. Sahoo et al. *Adv. Drug. Deliver. Rev.* 2018, 127, 185).

In particular, the inventors' have previously unveiled and sequenced "suckerin" proteins in international patent publication WO 2014/062134 A1 (S. H. Hiew et al., *ACS Biomater. Sci. & Eng.* 2017, 3, 680) which exhibits a block co-polymer primary structure and has been processed into various materials (D. Ding et al. *Adv. Mater.* 2015, 27, 3953; D. Ding et al. *J. Mater. Chem. B.* 2017, 5, 8467; V. Latza et al. *Nat. Comms.* 2015, 6, 8313; Y. Ping et al. *ACS Nano.* 2017, 11, 4528), including hydrogels via Ru-APS crosslinking (D. Ding et al. *Adv. Mater.* 2015, 27, 3953). Said "suckerin" proteins originate from suckerin proteins found in the sucker ring teeth (SRT) of the jumbo squid (P. A. Guerette et al. *ACS Nano.* 2014, 8, 7170; S. H. Hiew et al. *Acta Biomater.* 2016, 46, 41; S. H. Hiew et al. *ACS Biomater. Sci. & Eng.* 2016, 3, 680), which are a protein family with a characteristic modular primary structure consisting of long Gly-rich modules previously assumed to form mostly unordered domains that are interspersed by smaller Ala- and His-rich modules that self-assemble into stiffer β-sheet elements (S. H. Hiew et al. *Acta Biomater.* 2016, 46, 41; S. H. Hiew et al. *ACS Biomater. Sci. & Eng.* 2016, 3, 680). However, in a recent study by the inventors, NMR analysis indicated that the Gly-rich domain can also form β-sheets stabilized by aromatic side-chain interactions (A. Kumar et al. *Biomater. Sci.* 2018, 21, 401).

Despite various existing technologies, there is still a need for new short peptide-based hydrogels that have the potential to provide new characteristics, such as a broader range of moduli and water-based gelation. In particular, there is an unmet need for short peptide-based biocompatible hydrogels that form stable hydrogels under mild conditions (i.e. without the use of crosslinking agents and/or UV exposure) and exhibit a tunable, concentration-dependent mechanical response for the encapsulation and delivery of therapeutic agents such as secretome derived from MSCs. Wound healing is an example of a field where there is still particular need for such hydrogels which deliver encapsulated active agent(s) in a controlled manner for active wound management.

SUMMARY OF THE INVENTION

The present invention is based on the inventors' finding that certain peptides inspired by the suckerin protein (also referred to as GV8, GI8 peptides) described herein self-assemble into stable hydrogels under mild conditions without the need for toxic chemicals or free radical generating UV-light. During gelation, these peptides with an initial structure of $3_{10}$ helices undergo a novel and unique conformational transition into anti-parallel β-sheets with the formation of new inter-peptide hydrophobic interactions (FIG. 1). The inventors further observed that hydrogels derived from the peptides described herein exhibit a tunable, concentration-dependent mechanical response with an about 25-fold variation in storage modulus G', reaching a maximum value of about 35.5 kPa, which places such a hydrogel, despite comprising only natural amino acids, among the stiffest protein-based hydrogels. In addition, the inventors found that the hydrogels exhibit excellent biocompatibility in vitro and in vivo, making them promising candidates for the encapsulation and delivery of therapeutic agents. In fact, the incorporation of secretome derived from MSCs enhanced the structural integrity, shear modulus and reduced the degradation kinetics of the hydrogels. The hydrogels also exhibited controlled release of secretome, which promoted cell migration, cell proliferation, and ex ovo and in vivo angiogenesis, thereby accelerating the wound healing process. The present invention broadens the range of secondary structures available to create supramolecular hydrogels, and introduces $3_{10}$ helices as transient building blocks for gelation via a $3_{10}$ to β-sheet unique conformational transition. Further, the hydrogels of the present invention represent promising candidates for the encapsulation and delivery of therapeutic agents for active wound management.

In a first aspect, the present invention is thus directed to an isolated peptide comprising or consisting of the amino acid sequence:

$$(GX_1Z_1GGZ_2GB)_n(X_2)_m(GX_1Z_1GGZ_2GB)_o \quad \text{(SEQ ID NO: 3)}$$

wherein
each B is independently valine (V) or isoleucine (I);
each $X_1$ independently is an aliphatic amino acid, preferably leucine (L);
each $Z_1$, $Z_2$ is independently an aromatic amino acid, preferably tyrosine (Y);
$X_2$ is any amino acid;
m is 0 or an integer from 1 to 10;
n and o are independently 0 or an integer selected from 1, 2 or 3, provided that n+o is at least 1; and
wherein the isolated peptide is up to 50 amino acids in length.

In various embodiments, m is 0, o is 0 or both are 0.

In various embodiments, the isolated peptide comprises or consists of the amino acid sequence $(GX_1Z_1GGZ_2GB)_n$ (SEQ ID NO: 4), preferably it comprises or consists of the amino acid sequence $(GLYGGYGV)_n$ (SEQ ID NO: 5) or GLYGGYGV (SEQ ID NO: 1). In various other embodiments, the isolated peptide comprises or consists of the amino acid sequence $(GLYGGYGI)_n$ (SEQ ID NO: 6) or GLYGGYGI (SEQ ID NO: 2).

In various embodiments, the isolated peptide is at least partially in a $3_{10}$ helix conformation.

In various embodiments, the isolated peptide comprise or consist of the amino acid sequence, such as but not limited to: GLYGGYGV (SEQ ID NO: 1) or GLYGGYGI (SEQ ID NO: 2).

In various embodiments, the isolated peptide is up to 30 amino acids in length, up to 25 amino acids in length, up to 20 amino acids in length, up to 16 amino acids in length, up to 10 amino acids in length, and up to 8 amino acids in length.

In various embodiments, the isolated peptide is further acetylated at the N-terminus, and amidated at the C-terminus, i.e. that the isolated peptide comprises or consists of the amino acid sequence Ac-$(GX_1Z_1GGZ_2GB)_n(X_2)_m(GX_1Z_1GGZ_2GB)_o$-NH$_2$ (SEQ ID NO: 3).

In another aspect, the present invention is directed to a composition or a material for delivery of an active agent, wherein the composition or material comprises a hydrogel. The hydrogel includes the isolated peptides of the present invention, and, optionally, an active agent encapsulated in the hydrogel. In various embodiments, the peptides in the hydrogel are at least partially in a β-sheet conformation.

In various embodiments, the active agent is selected from the group comprising: complete cells, cellular components, proteins, (poly)peptides, carbohydrates, nucleic acids, lipids, (small) chemical compounds, nanoparticles, and combinations thereof.

In various embodiments, the active agent is a pharmaceutical or diagnostic agent.

In various embodiments, the pharmaceutical or diagnostic agent is secretome derived from MSC, for example, adipose-tissue derived MSC (also referred to as ADMSC). In various other embodiments, the pharmaceutical or diagnostic agent is vascular endothelial growth factor (VEGF).

In various embodiments, the composition or material is a pharmaceutical or diagnostic formulation for administration to a subject. In various embodiments, it can thus comprise any one or more auxiliaries, carriers and excipients that are pharmaceutically or diagnostically acceptable. In various embodiments, the composition or material is a hydrogel. The subject may be a mammal, for example, a human being.

In various embodiments, the composition or material is in the form of any one selected from the group of: a fibre, a filament, a film, a foam, a nano fibre, or a tissue scaffold.

The hydrogel itself is typically a colloidal gel with water as the dispersion medium.

In various embodiments, the pH of the composition or material is >4.0 and <8.0.

In a further aspect, the present invention is directed to a multi-layered composition or material for delivery of an active agent, the multi-layered composition or material comprising a multi-layered hydrogel. The hydrogel includes one or more isolated peptides of the present invention, and an active agent encapsulated in the multi-layered hydrogel. In various embodiments, the one or more isolated peptides in the multi-layered hydrogel are at least partially in a β-sheet conformation.

In still another aspect, the present invention is directed to a method for the encapsulation of an active agent in a hydrogel, the method comprising: (1) providing an aqueous solution of hydrogel-forming peptides, wherein the hydrogel-forming peptides comprise one or more isolated peptides of the present invention, (2) combining the aqueous solution of the hydrogel-forming peptides with a solution of an active agent, and (3) inducing formation of the hydrogel. In various embodiments, the one or more isolated peptides in the hydrogel are at least partially in a β-sheet conformation.

In various embodiments, the active agent in the combination step are also provided in the form of an aqueous solution. Said aqueous solution may have a pH below 8.0, and in some embodiments, is buffered such that the combination of the aqueous solution of the active agent with the aqueous solution of the hydrogel-forming peptides obtained in the combined aqueous solution has a pH below 8.0, for example, in the range of pH 4.0 to 7.5. In some embodiments, hydrogel formation occurs or is facilitated when the combination of the aqueous solution of the hydrogel-forming peptides and the active agent has a pH in the range of pH 5.0 to 7.5, for example, at pH 7.0 or at pH 6.5.

In various embodiments, the formation of the hydrogel occurs or is facilitated when the combined aqueous solution of the active agent and the hydrogel-forming peptides is at a temperature below 30° C., for example, in the range of 10° C. to 30° C. In some embodiments, inducing the formation of the hydrogel occurs or is facilitated at a temperature in the range of 20° C. to 25° C., for example, at 23° C. or 25° C.

In various embodiments, the formation of the hydrogel is facilitated in a time period of below 50 h, which includes the time required for the hydrogel to gelate and a post-gelation incubation time to maximize the stiffness of the hydrogel. In some embodiments, the formation of the hydrogel requires at least 1 h, or at least 2 h, for example, between 2 h to 10 h, or between 5 h to 10 h, or between 5 h to 9 h. In some embodiments, the post-gelation incubation time is in the range of 5 h to 20 h, for example, between 7 h to 12 h.

In various embodiments, the concentration of the one or more isolated hydrogel-forming peptides of the present invention in the combined aqueous solution of the hydrogel-forming peptides and the active agent is above 10 mM, for example, in the range of 10 mM to 80 mM. In some embodiments, the concentration of the one or more isolated peptides in the combined aqueous solution is in the range of 10 mM to 50 mM, for example, in the range of 10 mM to 30 mM, or in the range of 10 mM to 20 mM. In preferred embodiments, the concentration of the one or more isolated peptides is at about 20 mM, or at about 30 mM.

In various embodiments, the concentration of the active agent in the combined aqueous solution of the hydrogel-forming peptides and the active agent is above 5 µg/mL, for example, in the range of 6 µg/mL to 300 µg/mL, or in the range of 20 µg/mL to 300 µg/mL. In some embodiments, the concentration of the active agent in the combined aqueous solution is at about 6 µg/mL, at about 20 µg/mL, or at about 200 µg/mL.

In a further aspect, the present invention is directed to a method for diagnosing a condition or disease in a subject, comprising administering a composition or material comprising a hydrogel to a subject. In a still further aspect, the present invention is directed to a method for preventing or treating a condition or disease in a subject in need thereof. In such methods, the hydrogel comprises: (1) one or more hydrogel-forming peptides of the present invention, and (2) a pharmaceutical or diagnostic agent, wherein the pharmaceutical or diagnostic agent is encapsulated in the hydrogel. In various embodiments, the peptides comprised in the hydrogel are at least partially in a β-sheet conformation. The subject may be a mammal, for example, a human being.

In a non-limiting embodiment, the subject is a human afflicted by a tissue injury, and the pharmaceutical or diagnostic agent is secretome derived from MSCs, for example, ADMSC. The administration of the hydrogel is preferably topical, and secretome is optionally released from the hydrogel in a controlled manner.

In another non-limiting embodiment, the subject is a human afflicted by a tissue injury, and the pharmaceutical or diagnostic agent is the growth factor, VEGF. The administration of the hydrogel is preferably topical, and VEGF is optionally released from the hydrogel in a controlled manner.

It is understood that all combinations of the above disclosed embodiments are also intended to fall within the scope of the present invention. The details of one or more embodiments of the disclosure are set forth in the accompanying drawings and the detailed description below. Other features, objects and advantages will be apparent from the following detailed description and drawings, and from the claims.

BRIEF DESCRIPTION OF THE DRAWINGS

FIG. 4A-4G. Gelation kinetics observed via optical density measurements of $GX_8$ peptide solutions. Some sequences have higher solubilities than the others. FIG. 4A shows peptide GV8 incubated in DI water at various concentrations over a period of 40 h and observed for gelation via their absorbance at 550 nm; FIG. 4B shows peptide GL8 incubated in DI water at various concentrations over a period of 40 h and observed for gelation via their absorbance at 550 nm; FIG. 4C shows peptide GA8 incubated in DI water at various concentrations over a period of 40 h and observed for gelation via their absorbance at 550 nm; FIG. 4D shows peptide GF8 incubated in DI water at various concentrations over a period of 40 h and observed for gelation via their absorbance at 550 nm; FIG. 4E shows peptide GS8 incubated in DI water at various concentrations over a period of 40 h and observed for gelation via their absorbance at 550 nm; FIG. 4F shows peptide GK8 incubated in DI water at various concentrations over a period of 40 h and observed for gelation via their absorbance at 550 nm; FIG. 4G shows peptide GI8 incubated in DI water at various concentrations over a period of 40 h and observed for gelation via their absorbance at 550 nm. GI8 peptide self-assembly in water. FIG. 4H shows an inverted tube test to show hydrogel formation of a 10 mM GI8 peptide in water after 1 h incubation time. FIG. 4I shows a high resolution transmission electron microscopy (HR-TEM) image of self-assembled GI8 peptide fibrils after 40 m of incubation in water. FIG. 4J shows a selected area electron diffraction (SAED) pattern of the fibrils indicating higher order assemblies with 0.33 nm periodicity observed (plausibly attributed to interplanar spacing of the G-G side chain). FIG. 4K shows a CD spectra obtained of 10 mM GI8 peptide in water at 0 h and 48 h. Strong Y-Y cotton effect (228 nm) and 214 nm minima similar to that of GV8 peptide (plausibly turns and $3_{10}$ helix conformation) was observed at 0 h, whereas post-gelation spectra obtained of solution at 48 h show a β-sheet signature with low intensity as most peptides are involved in hydrogel formation (out of solution). FIG. 4L shows an ATR-FTIR spectra obtained of 10 mM GI8 peptide in water at 0, 24 and 48 h, which show a significant shift of Amide I band from mixed secondary structures to a β-sheet-dominated composition. Inset shows magnified Amide I band and a deconvoluted secondary structure composition of GI8 at different time points;

FIG. 5A shows an optical image of 2 beads formed by GL8 peptide and SEM images showing the morphology and fibrous macro-scale assembly of the beads. FIG. 5B shows that the Young's modulus obtained of GL8 beads performed via nanoindentation in dried and hydrated conditions were 8.34 GPa and 3.03 GPa respectively;

FIG. 6A shows cryo-EM micrographs of GV8 hydrogel fibrils and their twisted morphology (right image) with average periodicity of about 80 nm. FIG. 6B shows the AFM amplitude profile of dried GV8 hydrogel with fibers of about 6 nm to 10 nm height. FIG. 6C show SEM micrographs of GV8 hydrogel cross-section revealing sheet-like morphology (left image) made of fibers (right image). A photograph of the hydrogel is shown in the inset. FIG. 6D shows the scaling law plot of plateau G' vs. peptide concentration. FIG. 6E shows the CD spectra recorded over 50 h indicates significant increase in β-sheet content (intensity increase at $\lambda_{218\ nm}$). FIG. 6F shows the FTIR spectra recorded over 50 h indicates significant increase in β-sheet content (intensity increase at $\tilde{v}_{1634\ cm-1}$).

FIG. 8A shows amplitude sweeps that were performed on GV8 hydrogels of different concentrations (20 mM, 18 mM, 15 mM, 12 mM and 10 mM) to identify their linear viscoelastic region (LVE). FIG. 8B shows the storage modulus (G') obtained via frequency sweeps performed at 0.25% strain with n=3. FIG. 8C shows plots of 3 GV8 hydrogels at concentrations 20 mM, 15 mM and 10 mM illustrating their gel characteristics, storage modulus G'>G" (loss modulus);

FIG. 9A shows the SAXS profile for dried extruded GV8 gel. FIG. 9B shows the WAXS patterns of GV8 gel in the hydrated state. FIG. 9C shows the WAXS patterns of GV8 gel in the dried state;

FIG. 10A shows the deconvolution of ATR-FTIR spectra of GV8 self-assembly at 0 h. FIG. 10B shows the deconvolution of ATR-FTIR spectra of GV8 self-assembly at 1 h. FIG. 10C shows the deconvolution of ATR-FTIR spectra of GV8 self-assembly at 2 h. FIG. 10D shows the deconvolution of ATR-FTIR spectra of GV8 self-assembly at 3 h. FIG. 10E shows the deconvolution of ATR-FTIR spectra of GV8 self-assembly at 4 h. FIG. 10F shows the deconvolution of ATR-FTIR spectra of GV8 self-assembly at 5 h. FIG. 10G shows the deconvolution of ATR-FTIR spectra of GV8 self-assembly at 6 h. FIG. 10H shows the deconvolution of ATR-FTIR spectra of GV8 self-assembly at 7 h. FIG. 10I shows the deconvolution of ATR-FTIR spectra of GV8 self-assembly at 8 h. FIG. 10J shows the deconvolution of ATR-FTIR spectra of GV8 self-assembly at 25 h. FIG. 10K shows the deconvolution of ATR-FTIR spectra of GV8 self-assembly at 50 h.

FIG. 12A shows the 2D $^{1}$H-$^{1}$H TOCSY spectrum of 0.5 mM GV8 peptide delineating the individual spins of GV8 amino acid residues. FIG. 12B shows the bar diagram representation of NOE connectivities detected for GV8 peptide. FIG. 12C shows the 2D $^{1}$H-$^{1}$H NOESY spectra displaying weak ring interaction of Y3 and Y6. FIG. 12D shows the superimposition of ten lowest energy structures of GV8 peptide. FIG. 12E shows the representative structure of monomeric $3_{10}$ helix showing side chain stacking of Y3 and Y6;

FIG. 13A shows a CSD plot of H$^{\alpha}$ values from random coil of GV8 of hydrogel. FIG. 13B shows a one dimensional $^{1}$H spectra of 20 mM GV8 peptide as function of time (every 4 h) for 18 h. FIG. 13C shows a 2D $^{1}$H-$^{1}$H NOESY spectra at 0.5 mM peptide concentration of GL8 peptides indicating the absence of aromatic side chain interactions at 7.5 ppm to 7.0 ppm. FIG. 13D shows a 2D $^{1}$H-$^{1}$H NOESY spectra at 0.5 mM peptide concentration of GA8 peptides indicating the absence of aromatic side chain interactions at 7.5 ppm to 7.0 ppm;

FIG. 14. Structural statistics summary of 10 lowest energy structures of GV8 monomer and oligomer obtained from solution state NMR, and GV8 hydrogel by ssNMR;

FIG. 15A shows a 2D $^{1}$H-$^{1}$H TOCSY spectrum of 20 mM GV8 peptide delineating the individual spins of GV8 amino acid residues. FIG. 15B shows a bar diagram representation of residues that display sequential, medium range, and long-range NOEs detected at 20 mM concentration. FIG. 15C shows a 2D $^{1}$H-$^{1}$H NOESY spectra displaying long range cross-strand NOEs and ring proton interactions of Y3 and Y6 (marked with arrows and dotted lines). FIG. 15D shows the superimposition of ten lowest energy structures of GV8 peptide at oligomeric 20 mM concentration. FIG. 15E shows a representative structure of dimeric $3_{10}$ helix of GV8 oligomer showing side chain arrangement. Aliphatic residues (L2, V8, L2* and V8*) and aromatic residues (Y3, Y6, Y3* and Y6*) are labelled as shown;

FIG. 16A shows the H/D exchange protection factors for individual residues of GV8 peptide at 0.5 mM and 20 mM concentrations. FIG. 16B shows the amide proton temperature coefficients of individual amino acids of GV8 peptide at 0.5 mM and 20 mM concentrations;

FIG. 17A show strip plots of L2 and V8, 3D NCACX spectra of $^{13}$C-$^{15}$N labeled GV8 peptide hydrogel displaying long-range contact of residues. FIG. 17B shows the 2D $^{13}$C-$^{13}$C DARR spectra with contact time of 50 ms showing long-range dipolar contacts between L2 and V8 side chains (β, δ, γ). FIG. 17C shows the representative structure of dimeric extended conformation of GV8 hydrogel. FIG. 17D shows the side chain disposition representation of antiparallel β-sheets of GV8 hydrogel displaying inter-chain connectivity between L2 and V8 residues (L2/V8* and L2*/V8);

FIG. 18A shows the secondary structure distribution of each residue in dimer, tetramer, and octamer of GV8 at 300 K for 200 ns. FIG. 18B show the initial and final structures of a 40-mer model of the GV8 peptide with β-sheets structures shown. The inset in the bottom panel shows the representative structure in the model, whereby the π-π stacking and hydrophobic interactions mainly contribute to inter-sheet association;

FIG. 19A show that GV8+ hydrogels were demonstrated to have increased storage modulus (G'). FIG. 19B show that GV8+ hydrogels were demonstrated to have reduced degradation rates in solution;

FIG. 20A shows the gelation kinetics observed via optical density measurements at 550 nm of 30 mM GV8 and GV8+ peptide solutions with low (20 μg/mL) and high (200 μg/mL) secretome concentrations over a period of 8 h. FIG. 20B shows the time series CD spectra of 30 mM GV8 hydrogel with low (20 µg/mL) and high (200 µg/mL) secretome concentrations. FIG. 20C shows the time series CD spectra of 30 mM GV8+ hydrogel with low (20 µg/mL) and high (200 µg/mL) secretome concentrations;

FIG. 21A shows that the incorporation of secretome (i.e. GV8+ hydrogels) at 20 µg/mL concentration increases the storage modulus (G') of hydrogel, whereas incorporation of BSA at the same concentration reduces the GV8 hydrogel's storage modulus (G'). FIG. 21B shows that VEGF was encapsulated in a 30 mM GV8 hydrogel (GV8+ VEGF) at a concentration of 6 µg/mL in a one-pot formulation method similar to that of secretome encapsulation. An average G' value of 30.4 kPa was obtained for the (GV8+ VEGF) over triplicated measurements;

FIG. 23A shows that GV8 hydrogel is cytocompatible as demonstrated by cell attachment and proliferation studies with HaCaT keratinocytes, i.e. the spontaneously transformed aneuploid immortal keratinocyte cell line, and human dermal fibroblasts (HDF) cells. FIG. 23B shows the increased doubling rate of the HaCaT keratinocytes and HDF cells on the surface of GV8 hydrogel as compared to tissue culture plate (TCP). FIG. 23C shows the representative fluorescence images of HaCaT keratinocytes and HDF cell on the GV8 hydrogel, demonstrating healthy cell morphology after attachment;

FIG. 25A shows an increase in the overall blood vessel length and branch points in ex-ovo embryos was observed after 3 days. FIG. 25B shows that for the GV8+ VEGF hydrogels, the vessel density was determined by ImageJ analysis and vessel fold change was observed in ex-ovo embryos after 3 days. FIG. 25C shows representative selected images of the CAM assay for the GV8+ VEGF hydrogels and threshold analysis. An increase in the number of vessels and vessel diameter can be observed;

FIG. 27A shows a concentric GV8 hydrogel with a core gel indicated with bromophenol blue dye. FIG. 27B shows an optical microscope image of a representative weave patterned surface of the GV8 hydrogel. The inset shows that the entire surface of the disc-shaped GV8 hydrogel was patterned; FIG. 28A shows the hydrophobicity index of the GV8 peptide. FIG. 28B shows patterned GV8 hydrogel freshly prepared (before) and after 48 hours of immersion in solution.

DETAILED DESCRIPTION OF THE INVENTION

Figure 1:
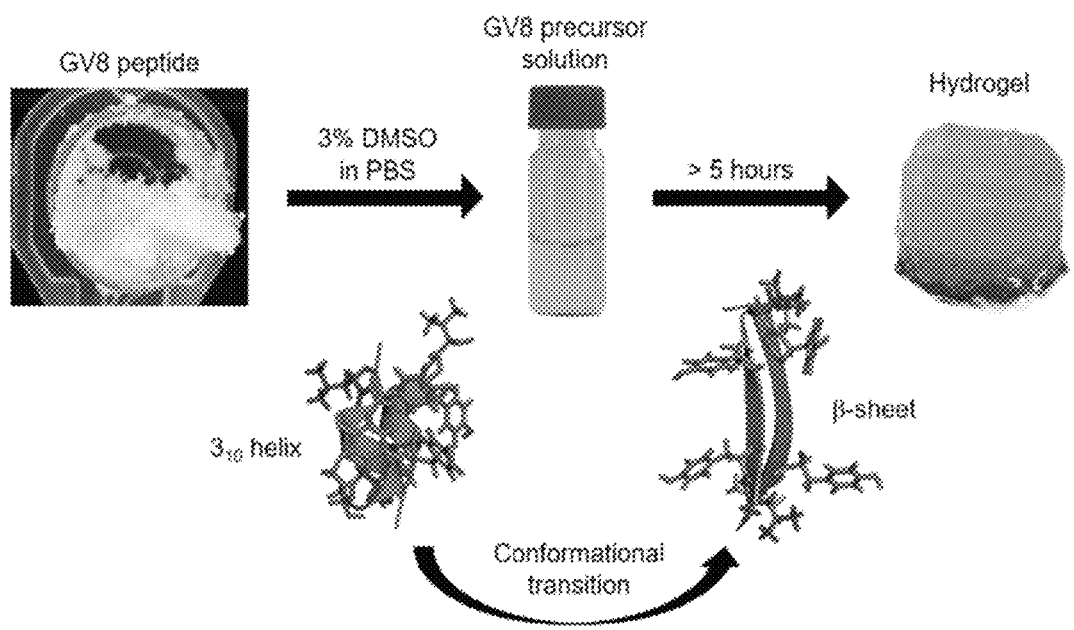
FIG. 1. Schematic of the GV8 hydrogel gelation. Lyophilized GV8 peptide powder is dissolved in de-ionized (DI) water or 3% v/v DMSO in PBS to form a GV8 precursor solution which gelates under ambient conditions via a unique secondary structure conformation transition.

The inventors found that engineered artificial peptides, inspired by sequence motifs from the suckerin protein, form monomeric $3_{10}$ helices in solution and undergo a novel and unique conformational change to form anti-parallel β-sheets that results in gelation and formation of hydrogels. Specifically, the inventors have found that the hydrogels formed from such engineered peptides are highly stable in water without any crosslinking agents, chemical modifications and/or UV exposure. The hydrogels described herein exhibit a tunable concentration-dependent mechanical response and allow encapsulation of active agent(s). Further, the hydrogels exhibit excellent biocompatibility in vitro and in vivo. In particular, it was observed that the controlled release of an encapsulated active agent from said hydrogels, namely secretome and/or VEGF, promoted wound healing.

The terms used herein have, unless explicitly stated otherwise, the meanings as commonly understood in the art.

In a first aspect, the present invention is thus directed to such peptides, preferably in isolated form, that comprise, consist essentially of or consist of the amino acid sequence: $(GX_1Z_1GGZ_2GB)_n(X_2)_m(GX_1Z_1GGZ_2GB)_o$ (SEQ ID NO: 3), preferably Ac-$(GX_1Z_1GGZ_2GB)_n(X_2)_m$ $(GX_1Z_1GGZ_2GB)_o$-$NH_2$(SEQ ID NO: 3), wherein each B is independently valine (V) or isoleucine (I);

each $X_1$ independently is an aliphatic amino acid, preferably leucine (L);

each $Z_1$, $Z_2$ is independently an aromatic amino acid, preferably tyrosine (Y);

$X_2$ is any amino acid;

m is 0 or an integer from 1 to 10;

n and o are independently 0 or an integer selected from 1, 2 or 3, provided that n+o is at least 1; and wherein the isolated peptide is up to 50 amino acids in length.

In various embodiments, m is 0, o is 0 or both are 0.

In various embodiments, the isolated peptide comprises or consists of the amino acid sequence $(GX_1Z_1GGZ_2GB)_n$ (SEQ ID NO: 4), preferably it comprises or consists of the amino acid sequence $(GLYGGYGV)_n$ (SEQ ID NO: 5) or GLYGGYGV (SEQ ID NO: 1). In various other embodiments, the isolated peptide comprises or consists of the amino acid sequence $(GLYGGYGI)_n$ (SEQ ID NO: 6) or GLYGGYGI (SEQ ID NO: 2).

Such peptides may be at least partially in a $3_{10}$ helix conformation. In such conformations, the side chains of aromatic amino acids $Z_1$, $Z_2$ and the aliphatic amino acids $X_1$ and B may be stacked along the $3_{10}$ helix. For instance, the side chains of aromatic amino acids $Z_1$, $Z_2$ are oriented perpendicular to the helical axis.

"Aromatic amino acids", as used herein, includes W, F and Y, with Y being preferred in the peptides of the invention.

"Aliphatic amino acids", as used herein, include A, V, L, and I, with a preference given to V, L and I in the peptides of the invention. In various embodiments, amino acid $X_1$ is preferably L, and B is either V or I.

In various embodiments, the isolated peptides comprise, consist essentially of or consist of the amino acid sequence: GLYGGYGV (SEQ ID NO: 1), preferably Ac-GLYG- GYGV-NH$_2$ (SEQ ID NO: 7), i.e. the Z$_1$ and Z$_2$ residues are Y residues, X$_1$ is a L residue, and B is a V residue. In various other embodiments, the isolated peptides comprise, consist essentially of or consists of the amino acid sequence: GLYGGYGI (SEQ ID NO: 2), preferably Ac-GLYGGYGI-NH$_2$ (SEQ ID NO: 8), i.e. the Z$_1$ and Z$_2$ residues are Y residues, X$_1$ is a L residue, and B is an I residue. Alternatively, only one of Z$_1$ and Z$_2$ may be Y and the other may be W or F. In such embodiments, X$_1$ may be V, L or I, preferably L. In such embodiments, acetylation at the C-terminus and amidation at the N-terminus is required for gelation of the hydrogel, as will be explained below.

The isolated peptides comprise a V residue (V8) or an I residue (I8) at the 8$^{th}$ (V8 or I8) position of the indicated consensus sequence. In preferred embodiments, the isolated peptides comprise a V residue at the 8$^{th}$ position, i.e. V8. It has been found that said residues are more or less invariable, since its substitution leads to a decrease in the desired hydrogel-forming properties of the peptides.

In the present invention, the isolated peptides at low concentrations, for example, at a concentration of 0.5 mM in water, are present in monomeric form, i.e. are free monomers in solution.

In the above sequence and all further sequences disclosed below, amino acids are identified by their one letter code. Thus, G stands for glycine, L stands for leucine, Y stands for tyrosine, V stands for valine, I stands for isoleucine, etc. The isolated peptides are also shown in the conventional manner, i.e. in the N- to C-terminal orientation. The individual amino acids are covalently coupled to each other by peptide bonds. If an amino acid is not defined or defined as being "any amino acid", this typically refers to the 20 naturally occurring proteinogenic amino acids G, A, V, L, I, F, W, Y, S, T, P, C, M, D, E, N, Q, K, H, and R.

The term "isolated", as used herein, relates to the fact that the referenced peptide is at least partially separated from other components it may (naturally or non-naturally) associate with, for example other molecules, cellular components and cellular debris. Said isolation may be achieved by purification protocols for proteins and peptides well known to those skilled in the art.

The term "peptide", as used herein, relates to polymers of amino acids, typically short strings of amino acids connected by covalent peptide bonds. In various non-limiting embodiments, the peptides may include only amino acids selected from the 20 proteinogenic amino acids encoded by the genetic code, namely, glycine, alanine, valine, leucine, isoleucine, phenylalanine, proline, serine, threonine, asparagine, glutamine, tyrosine, tryptophan, histidine, arginine, lysine, aspartic acid, glutamic acid, cysteine, and methionine. These amino acids are also designated herein by their three or one letter code (as above). The typical length for the peptides of the invention may range from 8 to 50 amino acids, preferably to 30, 25, 16 or 8 amino acids in length, for example, at least 8, 9, 10, 11, 12, 13, 14, 15, 16, 17, 18, 19, 20, 21, 22, 23, 24, 25, or 30 amino acids in length, the upper limit for example, being 50, 40 or 35 amino acids. Generally, it may be preferred to use peptides as short as possible without impairing their functionality, i.e. 8 amino acids in length. Accordingly, the term "peptide(s)", as used herein, refers to a unique polymer of amino acids, in accordance with various embodiments. It is understood that the term "isolated peptide", as used herein, is not intended to encompass the naturally occurring suckerin polypeptide. In various embodiments, the peptides of the invention are artificially created short sequence stretches of amino acids that have certain sequence identity to motifs within the suckerin sequence and may, in certain instances, be considered to be short (non-natural) fragments thereof.

The term "(amino acid) residue", as used herein, relates to one or more amino acids which are considered as part of the peptide.

The term "about", as used herein, in connection with a numerical value, means said value ±10%, for example, ±5%.

The term "at least partially in a 3$_{10}$ helix conformation", as used herein, refers to a peptide at least capable of adopting a conformation wherein each amino acid in the 3$_{10}$ helix corresponds to a 120° turn in the helix, i.e. the helix has three residues per turn, a transition of 2 Å along the helical axis, and forms a 10-membered ring by intramolecular hydrogen bonding. In particular, the N—H group of an amino acid forms a hydrogen bond with the C=O group of the amino acid three residues earlier, and the repeated i+3 to i hydrogen bonding thus defines the 3$_{10}$ helix. Such helical structures are commonly found in peptides and proteins, however not as main constituent secondary structures, and are well-known to those skilled in the art. Preferably, at least 20% or at least 40, 50, 60, 70, 80 or 90% of the peptide is able to adopt a 3$_{10}$ helix conformation.

In the above, the isolated peptide has a minimum length of 8 amino acids, and comprises, consists essentially of or consists of a single copy of the indicated amino acid sequence.

In various embodiments, the isolated peptides may consist of the given amino acid sequence. In such embodiments, there are no further N- and/or C-terminal flanking peptide sequences. Alternatively, the isolated peptides may essentially consist of the amino acid sequence given. In such embodiments, there may be N- and/or C-terminal peptide sequences that flank the core consensus sequence. These are in such embodiments 1 to 10 amino acids in length, for example 1, 2, 3, 4, 5, 6, 7, 8, 9 or 10 amino acids in length. In such embodiments, it may be preferred that the flanking sequences in sum are not longer than the core sequence defined by the above consensus sequence. In some embodiments, the flanking sequence may comprise glycine G residues, for example 5 or 10 G residues between repeats of the core consensus sequence, if desired. However, in various embodiments, it is preferred that the isolated peptides of the present invention comprise, consist of or consist essentially of the amino acid sequence given herein. It is generally advantageous to use a peptide that only includes the minimum sequence, i.e. 8 amino acids in length, necessary to fulfill its function, i.e. in the present case, to self-assemble and form stable hydrogels under the desired conditions.

In some embodiments, the upper limit in peptide length of the isolated peptides is 40 amino acids, for example, up to 35, up to 32, or up to 25 amino acids in length. In various embodiments, the isolated peptides may be up to 25 amino acids in length, for example, 24 amino acids in length, and include 2 or 3 repeat copies of the indicated amino acid sequence. In some embodiments, the isolated peptide may be up to 16 amino acids in length, and include 2 repeat copies of the indicated amino acid sequence. In preferred embodiments, the isolated peptide has a length of 8 amino acids and consists of a single copy of the indicated amino acid sequence.

The inventors found that the isolated peptides of the present invention, comprising the minimum sequence, i.e. 8 amino acids in length, exhibited a predominantly helical structure as indicated by negative $^1$H$^\alpha$ chemical shifts. In particular, the isolated peptides exhibited (i, i+3) H$^\alpha$-H$^N$ Nuclear Overhauser Effects (NOEs) in addition to the strong (i, i+1) H$^N$-H$^N$ NOEs, indicating the presence of a 3$_{10}$ helix conformation. Further analysis also revealed the presence of ring proton NOEs between the aromatic $Z_1$ and $Z_2$ residues, i.e. weak ring interactions between the Y3 and Y6 residues of the amino acid sequence, and NOEs between the aliphatic $X_1$ and B residues (where B is either I or V), i.e. between the L2, and V8 or I8 residues of the amino acid sequence. Specifically, the $Z_1$ and $Z_2$ residues were observed to exhibit π-π stacking interactions. In various embodiments, the G residues displayed a protection factor (calculated from H/D exchange and amide proton temperature coefficients at various temperatures) of 60-80, indicating significant H/D exchange protection inside the core of the $3_{10}$ helical structure. The amide proton temperature coefficients for all residues of the isolated peptides exhibited values more positive than −4.6 ppb/K, and the G residues also exhibited more positive values in line with their higher protection factor values. Collectively, these findings support the hypothesis that the isolated peptides of the present invention adopt a well-defined $3_{10}$ helix conformation.

In some embodiments, the isolated peptides may further include turns. The term "turns", as used herein, may include type I, II and III turns each containing a hydrogen bond between the carbonyl oxygen of the $i^{th}$ residue and the amide nitrogen of i+3. The turns may include or may be type III turns of the $3_{10}$ helix conformation, including a hydrogen bond between CO of the $i^{th}$ residue and the NH of the i+3 residue. The backbone dihedral Φ and Ψ angles are (−60°, −30°) and (−60°, −30°) of the i+1 and i+2 residues, respectively, of the classical type III turn. In preferred embodiments, the isolated peptides adopt the secondary structure comprising, predominantly, the $3_{10}$ helix and in some cases, turns.

In various embodiments, the isolated peptide is acetylated at the N-terminus, and amidated at the C-terminus. Thus, the isolated peptide contains an added acetyl (—CH) group at the N-terminus, i.e. at the G residue at the $1^{st}$ position of the amino acid sequence, and contains an added amine (—NH$_2$) group at the C-terminus, i.e. at the B residue (V8 or I8) at the $8^{th}$ position of the amino acid sequence. In other words, the amino acid sequence comprises, consists essentially of or consists of the amino acid sequence: Ac-(GX$_1$Z$_1$GGZ$_2$GB)$_n$-NH$_2$ (SEQ ID NO: 4) wherein n, $X_1$, $Z_1$, $Z_2$, B are as defined above. In preferred embodiments, the amino acid sequence comprises, consists essentially of or consists of the amino acid sequence: Ac-GLYGGYGV-NH$_2$ (SEQ ID NO: 7), or Ac-GLYGGYGI-NH$_2$ (SEQ ID NO: 8). The acetylation at the N-terminal and amidation at the C-terminal of the isolated peptide is required for gelation of the hydrogel, and further prevents end-to-end charge interactions between individual isolated peptides of the present invention, and/or interactions with various other peptides or proteins.

In another aspect, the present invention is directed to a composition or a material for delivery of an active agent, wherein the composition or material comprises a hydrogel. The hydrogel includes one or more isolated peptides of the present invention, and an active agent encapsulated in the hydrogel. In various embodiments, the one or more isolated peptides forming the hydrogel are at least partially in a β-sheet conformation, preferably, an anti-parallel β-sheet conformation.

The term "hydrogel", as used herein, refers to a network of crosslinked hydrophilic polymer chains that comprise a large amount of water. In various embodiments, the hydrogel may contain at least 80, 90, 95, or 99% water. The hydrogel of the present invention maintains its structural integrity due to (non-covalent) crosslinks between the one or more isolated peptides of the present invention, which form a fibrous network wherein the peptides of the invention adopt an anti-parallel β-sheet conformation. In various embodiments, the hydrogel, as described herein, refers to a porous hydrogel, where the porosity may be controlled through the various factors including, but not limited to, the degree of crosslinking within the fibrous network of the one or more isolated peptides and affinity of the hydrogel to the aqueous environment. In preferred embodiments, the porosity of the hydrogel is controlled through the concentration of the one or more isolated peptides which form the hydrogel as will be explained below. "Stable", as used herein, in relation to the hydrogel of the present invention, primarily relates to the resistance to degradation. Generally, factors that affect degradation behavior of hydrogels may also apply to the hydrogels of the present invention.

The term "encapsulate", as used herein, in relation to the active agent, means that the active agent is entrapped in the hydrogel, i.e. entrapped within the porous network of peptides which form the hydrogel. The entrapment is such that the active agent is completely entrapped, enmeshed or entangled by the network of peptides which form the hydrogel. Alternatively, the active agent may at least be partially exposed on the surface of the hydrogel, for instance, by being tethered to the hydrogel via a certain group or moiety, i.e. may form a coating on the hydrogel. In preferred embodiments, the active agent is however incorporated and physically absorbed into the peptide network of the hydrogel and is thus entrapped within said network.

The term "delivery", as used herein, in relation to the active agent, means that the active agent, which is encapsulated in the hydrogel, can be released under certain conditions. In various embodiments, release and delivery of the active agent are effected via diffusion where the encapsulated active agent diffuses, i.e. moves or migrates, through the porous network to escape from the hydrogel. In particular, the release and delivery of the active agent is via the net movement of the active agent from a region of higher concentration, i.e. within the hydrogel, to a region of lower concentration, for example, a dilute aqueous environment or a tissue injury site. In some embodiments, delivery of the active agent is facilitated by topically administering the hydrogel to a subject in need thereof, as will be explained below. In various embodiments, the rate of the release, i.e. release profile or kinetics, of the active agent can be controlled by controlling the porosity, i.e. degree of crosslinking within the network of isolated peptides of the hydrogel by adjusting the concentration of the one or more isolated peptides in the hydrogel. In various embodiments, the concentration of the one or more isolated peptides is inversely proportional to the degree of porosity in the hydrogel. For example, increasing the concentration of the one or more isolated peptides in the aqueous solution of hydrogel-forming peptides increases the degree of crosslinking in the network of peptides and decreases the porosity of the hydrogel, and vice versa.

The term "at least partially in a β-sheet conformation", as used herein, refers to the isolated peptides adopting a conformation where at least two backbones of 3 or more amino acids are connected laterally via hydrogen bonds. The peptides in the hydrogel may include other structural conformations provided at least part of the one or more isolated peptides within the hydrogel have at least two backbones of 3 or more amino acids which are connected laterally via hydrogen bonds. Preferably, at least 20% or at least 40, 50, 60, 70, 80 or 90% of the one or more isolated peptides are able to form into a β-sheet. In preferred embodiments, the one or more isolated peptides conform into anti-parallel β-sheets under hydrated or dehydrated conditions via localized hydrogen bonds that play a role in tuning the mechanical properties of the hydrogel. Such β-sheet conformation is commonly found in peptides and polypeptides and well-known to those skilled in the art.

The inventors found that the transformation from the liquid state of the aqueous solution of hydrogel-forming peptides of the present invention to the hydrogel involves a novel secondary structural transition from the $3_{10}$ helix conformation to the anti-parallel β-sheet conformation. The formed hydrogel exhibits tunable concentration-dependent mechanical properties and allows successfully encapsulating and delivering the active agent.

Prior to formation of the anti-parallel β-sheets, the at higher concentrations, i.e. at 20 mM, the peptides of the present invention form oligopeptides, involving a structural rearrangement for incorporation into the hydrogel, wherein the peptides dimerize into anti-parallel $3_{10}$ helices driven by π-π stacking aromatic interactions between the $Z_1$ and $Z_2$ residues of the one or more isolated peptides. For instance, the $Z_1$ residue of a first isolated peptide forms π-π stacking interactions with a $Z_2$ residue of the second isolated peptide of the one or more isolated peptides, i.e. the Y3 residue of the first isolated peptide forms π-π stacking interactions with the Y6 residue of the second isolated peptide. Further, it was observed that residues at the C-terminal, i.e. G7 and B (where B is either I or V, i.e. V8 or I8) of the first isolated peptide, display long range NOEs with residues at the N-terminal, i.e. $X_1$ and $Z_1$ (L2 and Y3) of the second isolated peptide, contributing to the oligomerization of the peptides after gelation. Using 5 G residues as linkers between the consensus core motifs, it was also observed that the $3_{10}$ helices form dimeric $3_{10}$ anti-parallel helical building blocks prior to forming anti-parallel β-sheets. Specifically, 3D structure calculation revealed that the hydrophobic face of the dimeric $3_{10}$ helices comprises π-stacking interactions between the $Z_1$ and $Z_2$ aromatic residues, i.e. Y3 and Y6, between individual isolated peptides of the one or more isolated peptides, while the exposed side of the dimeric helix comprises the $X_1$, i.e. L2 and B, i.e. the V8 or I8 aliphatic residues. In addition, the G residues also displayed a protection factor of 60-80 supporting significant H/D exchange protection inside the core of the dimeric $3_{10}$ helices. The protection factor of the $Z_1$ and $Z_2$ aromatic residues, i.e. Y3 and Y6 also increases with increasing concentrations of the one or more isolated peptides, indicating enhanced aromatic interactions in oligomers.

The inventors' further found that the formation of the 3D stable hydrogel comprises the self-assembly and structural rearrangement of the peptides of the invention to form anti-parallel β-sheets, i.e. from the $3_{10}$ helices to anti-parallel $3_{10}$ helical building blocks and subsequently, to the anti-parallel β-sheets. Specifically, gelation of the peptides of the present invention comprises the growth of short fibrillar clusters between the peptides, and conformational transitions. In particular, the peptides within the hydrogel exhibit long range dipolar contact between the $X_1$ and B, i.e. V or I aliphatic residues of the different peptides, i.e. the L2 residue of the first isolated peptide formed long range dipolar contacts between the V8 or I8 residues of the second isolated peptide, and vice versa. The ring packing interactions between the $Z_1$ and $Z_2$ aromatic residues, i.e. between the Y3 and Y6 residues, which were present in the monomeric phase, are then no longer present. Further, the residues at the C-terminus, i.e. G7 and V8 or I8 of the first isolated peptide, form long range NOEs with residues at the N-terminus, i.e. L2 and Y3 of the second isolated peptide. It can thus be assumed that during gelation, the $Z_1$ and $Z_2$ aromatic residues rearrange to be exposed to solvent and at the same time, stronger hydrophobic interactions between the $X_1$ and B, i.e. V or I aliphatic residues of different peptides of the one or more isolated peptides stabilize the anti-parallel β-sheet conformation of the hydrogel. This can be attributed to the presence of the V8 or the I8 residue at the C-terminal of the isolated peptide which plays a crucial role in stabilizing the $3_{10}$ helix structural intermediate through intrachain hydrophobic interactions, i.e. through structural hydrophobic interactions of π-π stacking of the $Z_1$ (Y3) and $Z_2$ (Y6) aromatic residues at the side chain of the one or more isolated peptides allowing them to engage in intersheet interactions. For example, mutating the B, i.e. V or I residue at the C-terminal, i.e. at the 8th position of the indicated consensus sequence, significantly impaired or abrogated the gelation capabilities of the isolated peptide.

Upon incorporation of the active agent into the hydrogel of the present invention, the inventors found that the active agent improved the physico-chemical properties of the hydrogel by enhancing the structural integrity and shear modulus of the hydrogel and concomitantly reducing the degradation kinetics of the hydrogel. Without wishing to be bound to this hypothesis, it is assumed that physical interactions, such as hydrophobic and π-π interactions, between the active agent, i.e. secretome components, e.g. growth factors and cytokines, and the peptides of the hydrogel improve the physico-chemical properties as observed. Further, the hydrogel exhibits excellent biocompatibility in vitro and in vivo, and releases the encapsulated active agent in a controlled manner.

In various embodiments, the active agent may, for example, be a pharmaceutical or diagnostic agent. Generally, it includes but is not limited to, complete cells, cellular components, such as cell organelles, proteins, (poly)peptides, carbohydrates, nucleic acids, lipids, (small) chemical compounds and nanoparticles. Suitable nanoparticles include those, such as but not limited to, metal nanoparticles, metal oxide nanoparticles and combinations thereof. The nanoparticles may be magnetic nanoparticles. "Nanoparticles", as used herein, refer to particles that have dimensions, such as the equivalent spherical diameter (ESD), referring to the diameter of a perfect sphere of equivalent volume as the potentially irregular shaped particle, in the nanometer range, typically up to 500 nm, for example up to 250 or up to 100 nm. The nanoparticles may be substantially spherical in shape in a non-limiting embodiment. "Chemical compounds", as used in this context, relates in particular to molecules, for example, molecules of varying molecular weights, for example, organic compounds with a molecular weight up to 500 kDa. "Small chemical compounds" refers to small molecules, i.e. typically organic molecules of a molecular weight of up to 1000 g/mol. Many drugs fall into this category of compounds.

In various other embodiments, the pharmaceutical or diagnostic agent may include or be, but is not limited to, RNA oligonucleotides or variants thereof, such as, plasmid DNAs, small interfering RNAs, microRNAs, messenger RNAs, long non-coding RNAs, and other RNA oligonucleotides such as those used in CRISPR/Cas9 or other genome-editing systems, antibodies or antibody-like molecules, enzymes, and the like. In some embodiments, the active agent may include or be, but is not limited to, agents which promote and accelerate the wound healing process, and includes growth factors, cytokines, chemokines, ions and vulnerary agents. "Growth factors", as used in this context, relates to molecules important for regulating a variety of cellular processors such as cell proliferation, migration, and angiogenesis. Examples of molecules in this group may comprise, but is not limited to, epidermal growth factor, fibroblast growth factor, VEGF and transforming growth factor-β. "Cytokines", as used in this context, relates to small proteins and peptides important for cell signaling, that are involved in autocrine, paracrine, endocrine signaling as immunomodulating agents. Examples may comprise, but are not limited to, interferons, interleukins, lymphokines and tumor necrosis factors.

In various embodiments, the pharmaceutical or diagnostic agent consists, comprises essentially of or comprises secretome, preferably derived from MSCs, for example, human adipose MSCs (ADMSCs). As discussed in the background section, MSCs are excellent therapeutic candidates for wound healing due to their excellent self-renewal and differential potential as well as good immune modulatory and pro-angiogenic functions beneficial for tissue regeneration. In particular, secretome, i.e. signaling molecules secreted by MSCs, contain a broad range of proteins which are beneficial for the wound healing process. "Secretome", as used herein, thus includes the set of proteins secreted by a given cell or type of cell, such as from MSCs (ADMSCs), into the extracellular space. Generally, this includes cytokines, growth factors, chemokines, cytokines, hormones, adhesion molecules, proteases, extracellular matrix proteins, i.e. matrisome, regulators and shed receptors. In addition to protein cargo, secretome may further include non-protein components such as lipids, micro-RNAs and exosomes. In the present invention, secretome derived from ADMSCs promotes the wound healing process by stimulating cell proliferation, migration and angiogenesis.

In various embodiments, the pharmaceutical or diagnostic agent consists, comprises essentially of or comprises VEGF, for example, recombinant VEGF. "VEGF", as used herein, refers to the signaling protein that promotes angiogenesis. In the present invention, VEGF promotes the wound healing process by stimulating the formation and growth of new blood vessels after tissue injury. As a result, oxygen supply (via the delivery of oxygenated blood) to the site of tissue injury is restored.

In various embodiments, the composition or material comprises a pharmaceutical or diagnostic formulation for administration to a subject. Such formulations may additionally comprise all the known and accepted additional components for such applications. These include auxiliaries, carriers and excipients that are pharmaceutically or diagnostically acceptable, for example various solvents, preservatives, dyes, stabilizers and the like. Such formulations may additionally comprise further active agents that are not encapsulated in the hydrogel. In some embodiments, such compositions or materials are liquid compositions or materials such as gels, including hydrogels as such, typically colloidal gels, and pastes. "Liquid", as used herein, particularly refers to compositions or materials that are liquid under standard conditions, i.e. 20° C. and 1013 mbar, and maintain their structural integrity by the fibrous network comprising the one or more isolated peptides of the invention. In various embodiments, such liquid compositions or materials are pourable and/or adopt the 3D shape conforming to shape of the mold they were formed in. Such compositions and materials may be Non-Newtonian fluids and may have a yield point. The compositions or materials may be in single dose or multi dose form. Suitable forms and packaging options are well known to those skilled in the art. In some embodiments, the composition or material of the present invention may also be incorporated into bandages, surgical and dental wound packing material, diapers and catamenial devices, and the like.

In various embodiments, the release and subsequent delivery of the active agent comprises controlled release where release occurs over a prolonged duration. Generally, the release occurs within several minutes upon administration of the hydrogel to a subject, and may continue to be released over several weeks or days. In some embodiments, the rate of release may be constant over the duration at which the active agent is released from the hydrogel. In some other embodiments, the rate of release may vary over the duration at which the active agent is released from the hydrogel. In various embodiments, the rate of release may be controlled through the porosity of the hydrogel, specifically, through the concentration of the one or more isolated peptides in the hydrogel. The release may be via diffusion where the active agent diffuses through the fibrous network of the hydrogel to the site of tissue injury, upon administration of the hydrogel to a subject in need thereof. The release may continue until all the encapsulated active agent diffuses from the hydrogel to the site of tissue injury.

In various embodiments, the composition or material can be adapted for administration to a mammalian subject, for example, a human being. In preferred embodiments, administration of the composition or material is topical. "Topical", as used herein, means the application of the hydrogel to the site of the desired action, typically a body surface, such as the skin or mucous membranes, for example to treat an ailment such as a tissue injury, i.e. wound. In some embodiments, topical administration may include absorption of the active agent to the application site to attain local effects. In other embodiments, administration of the hydrogel may be systemic by any suitable route.

Typically, topical administration of the composition or material is epicutaneous, in that the hydrogel is applied directly to the skin, or applied to surface of tissues other than the skin, such as the surface of a tooth or a mucous membrane, such as those of the eye or ear, including but not limited to, the conjunctiva of the eye, oral cavity, nasopharynx, vagina, colon, urethra. In various embodiments, administration of the hydrogel is transdermal, for example through the dermis or skin of the subject.

In various embodiments, the composition or material of the present invention is a hydrogel comprising one or more isolated peptides as described. Preferably, the peptides in the hydrogel are at least partially in the β-sheet conformation, most preferably, in the anti-parallel β-sheet conformation. In some embodiments, the composition may have the form of: a fibre, a filament, a film, a foam, a nano-fibre, or a colloidal solution. In a preferred embodiment, the hydrogel comprises a fibrous network of the peptides of the invention, which form a porous 3D structure by the formation of anti-parallel β-sheets. In particular, the hydrogel comprises long fibers less than 10 nm wide with consistent twisted morphologies and an average period of approximately 80 nm along the fibers. In such embodiments, the hydrogel comprises nanofibrils comprising the peptides of the present invention.

In various embodiments, the composition or material has a pH below 8.0, and in some embodiments, a pH greater than 4.0. For example, the pH of the hydrogel may be in the range of pH 4.0 to 6.0, or pH 5.5 to 7.5. At this pH range, the hydrogel remains stable and adopts the 3D structure comprising the porous fibrous network of the peptides of the present invention. Thus, the hydrogel, which is at least partially in the anti-parallel β-sheet conformation, remains stable under mildly acidic conditions, or at physiological pH.

An aspect of the present invention also relates to a multi-layered composition or material for delivery of an active agent, the multi-layered composition or material comprising a multi-layered hydrogel. In various embodiments, the multi-layered hydrogel includes one or more isolated peptides of the present invention, and the hydrogel is at least partially in the β-sheet conformation, preferably, the anti-parallel β-sheet conformation. Multi-layered hydrogels are formed in a concentric manner by forming additional gel layer(s) over a pre-formed hydrogel layer(s). Generally, the additional gel layer(s) are larger, i.e. having a larger length or diameter, than the pre-formed hydrogel layer. For example, a 2-layered composition or material comprises a second larger hydrogel layer formed over a first smaller pre-formed hydrogel layer. In preferred embodiments, the first pre-formed hydrogel layer forms the common center of the multi-layered composition or material, i.e. concentric.

The term, "multi-layer", as used herein, in relation to the hydrogel, means consisting of more than one, or several layers. In various embodiments, a multi-layered composition or material comprises 2, 3, 4, 5, 6, 7, 8, 9, 10 layers of the hydrogel. In some embodiments, the multi-layered composition or material comprises no more than 5 layers, i.e. the first center hydrogel layer and four additional hydrogel layers surrounding the center hydrogel layer. "Formation", as used herein, in relation to the additional hydrogel layer(s), means depositing or coating. For example, the second hydrogel layer is deposited or coated around the first pre-formed hydrogel layer, i.e. the center hydrogel layer. "Concentric", as used herein, in relation to the hydrogel, refers to arcs, circles or other shapes which share a common center, the larger hydrogel layer completely surrounding the smaller hydrogel layer, i.e. the larger second hydrogel layer completely surrounds the smaller first hydrogel layer and the common center may be the first hydrogel layer.

In some embodiments, the active agent in encapsulated in each of the individual hydrogel layers, i.e. all the layers which form the multi-layered composition or material. In some other embodiments, the active agent in encapsulated in the first, i.e. center hydrogel layer, but not in the additional hydrogel layer(s). Formation of the multi-layered composition or material comprising the one or more isolated peptides of the present invention provides greater control over the release profile of the encapsulated active agent from the hydrogel. For example, release of the encapsulated active agent is slower in multi-layered hydrogels as compared to hydrogels comprising a single layer, since the encapsulated active agent has to diffuse through more than one hydrogel layer.

Methods of manufacture of the above composition or material is also disclosed in a further aspect of the present invention. Methods for the encapsulation of an active agent in a hydrogel comprise: (1) providing an aqueous solution of hydrogel-forming peptides, said hydrogel-forming peptides comprising or being the peptides of the present invention, (2) combining the aqueous solution of the hydrogel-forming peptides with a solution of an active agent, and (3) inducing hydrogel formation. In various embodiments, the hydrogel-forming peptides are at least partially in the $3_{10}$ helix conformation in the aqueous solution. In various embodiments, the peptides in the hydrogel encapsulating the active agent are at least partially in the β-sheet conformation, preferably anti-parallel β-sheet conformation. In various embodiments, inducing hydrogel formation thus includes the novel secondary structural transition from the $3_{10}$ helix conformation to the anti-parallel β-sheet conformation.

The inventors found that the isolated peptides of the present invention self-assemble under mild conditions without the need for crosslinking agents, to form stable hydrogels with tunable concentration-dependent mechanical properties through a novel and unique secondary structural transition, and at the same time, encapsulating the active agent. Said hydrogels were further found to exhibit excellent biocompatibility in vitro and in vivo and releases the encapsulated active agent in a controlled manner. In various embodiments, stable solutions of the isolated peptides were prepared at physiological pH in solvents comprising mainly water and trace amounts of organic components, for example, dimethyl sulfoxide below 3% v/v in the aqueous solution of hydrogel-forming peptides. In various embodiments, stock solutions of the isolated peptides may be stored under weak acidic conditions or at physiological pH, for example at a range of pH 4.0 or 8.0, for example, in water or sodium acetate buffered solutions with a pH ranging from 4.0 to 8.0.

In various embodiments, the method of manufacture of the above composition or material further includes forming multi-layered hydrogels. Methods for the encapsulation of an active agent in a multi-layered hydrogel comprise: (1) forming the first layer of the hydrogel comprising: (a) providing an aqueous solution of hydrogel-forming peptides, said hydrogel-forming peptides comprising or being the peptides of the present invention, (b) combining the aqueous solution of the hydrogel-forming peptides with a solution of an active agent, and (c) inducing hydrogel formation, (2) forming the additional layer(s) of the multi-layered hydrogels comprising at least: (a) providing an aqueous solution of hydrogel-forming peptides, said hydrogel-forming peptides comprising or being the peptides of the present invention, and (b) inducing hydrogel formation of the additional layer(s). In some embodiments, the forming the additional layer(s) of the multi-layered hydrogels may further comprise combining the aqueous solution of the hydrogel-forming peptides with a solution of an active agent. In preferred embodiments, the additional hydrogel layer(s) of the multi-layered composition or material does not comprise said encapsulated active agent.

The term "aqueous solution", as used herein, means that the dilute phase is mainly water, i.e. comprises at least 50 vol. % water. In various embodiments, the aqueous solution of the hydrogel-forming peptides may use water as the only solvent, i.e. no additional organic solvents, such as alcohols, are present. In other embodiments, the aqueous solution of the hydrogel-forming peptides is an aqueous composition that additionally contains one or more solvents other than water, with water however being the major constituent, i.e. being present in an amount of at least 50, at least 60, at least 70, at least 80, at least 90, at least 95 or 99 vol. %. For example, the solvent may include, organic compounds, inorganic salts and amino acids in addition to water, with water being the major constituent.

In various embodiments, for forming the hydrogel and at the same time encapsulating the active agent, the aqueous solution of the hydrogel-forming peptides is combined with an aqueous solution of the active agent or alternative a dispersion of the active agent in an aqueous medium, and hydrogel formation is induced. In various embodiments, combining the aqueous solution/dispersion of the active agent with the aqueous solution of the hydrogel-forming peptides may be performed with gentle and consistent agitation, i.e. mixing or stirring. In various embodiments, combining the aforementioned aqueous solutions includes buffering the aqueous solution/dispersion of the active agent such that the combination of the aqueous solution of the active agent and the hydrogel-forming peptides, as well as optionally, the additional components and/or auxiliaries, is at a pH of about 4.0 or more, or at about pH 6.0 or more. It was found that the optimal pH for the combination of the aforementioned aqueous solutions/dispersions is at pH of about 7.0 and more, and in various embodiments, not higher than pH 8.0. To maintain such pH, the active agent is dissolved or diluted or dispersed in a suitable buffering agent, for example, a buffering agent with a pH between 6.0 to 7.5, for example, phosphate buffers with a pH of 7.0 to about 7.5, such that the combined aqueous solution of the hydrogel-forming peptides and the active agent retains a pH of about 6.0 to 8.0, at about pH 7.0, or at about pH 7.5.

In various embodiments, inducing the formation of the hydrogel comprises leaving the combined aqueous solution of the hydrogel-forming peptides and the active agent in a sealed environment, for example, an enclosed receptacle or vessel, to gelate. The receptacle provides a mold for the hydrogel to form, and the enclosed environment may provide the humid conditions required for the hydrogel to gel, and prevent external contaminants from entering the combined aqueous solution of the hydrogel-forming peptides and the active agent. In various embodiments, the formed hydrogel adopts the shape and dimensions, i.e. 3D dimensions, of the receptacle. For example, the hydrogel encapsulating the active agent adopts the circumference, diameter, height and shape of the (circular) container that contained the combined aqueous solution of the hydrogel-forming peptides and the active agent prior to gel formation. In various embodiments, the hydrogel may be patterned, for example, by placing the combined aqueous solution of the hydrogel-forming peptides and the active agent in a receptacle that includes a patterned surface, and inducing the formation of the hydrogel. The patterned hydrogels do not swell and deform since the isolated peptides of the present invention are hydrophobic.

In various embodiments, the formation of the hydrogel comprises incubating the combined aqueous solution of the hydrogel-forming peptides and the active agent at a temperature at about 15° C. or more, or at about 20° C. or more. It was found that the optimal temperature for the formation of the hydrogel is at about 22° C. or more, and in various embodiments, not higher than 30° C., for example, at about 23° C., or at about 25° C.

In various embodiments, the formation of the hydrogel comprises incubating the combined aqueous solution of the hydrogel-forming peptides and the active agent in the enclosed environment and at the indicated temperature for about 1 h or more, or 2 h or more, or 5 h or more, or 7 h or more, or 9 h or more. In various embodiments, where the B residue is an I residue, i.e. Ac-(GX$_1$Z$_1$GGZ$_2$GI)_NH$_2$(SEQ ID NO: 9), formation of the hydrogel at the indicated conditions requires about 2 h or more. In various other embodiments, where the B residue is a V residue, i.e. Ac-(GX$_1$Z$_1$GGZ$_2$GV)_NH$_2$(SEQ ID NO: 10), formation of the hydrogel at the indicated conditions requires 5 h or more. In some embodiments, the set hydrogel was left to further incubate in the enclosed environment and at the indicated temperature for a further 7 h or more, or 10 h or more, to ensure that the hydrogel obtains maximal stiffness prior to handling and application. Thus, the total duration required to induce the formation of the hydrogel is at about 2 h or more, at about 5 h or more, or at about 15 h or more, and in various embodiments, not higher than 50 h. It was found that the optimal duration for inducing the formation of the hydrogel and successfully encapsulating the active agent is at about 9 h or more, or at about 12 h or more, and in various embodiments, not higher than 30 h.

In various embodiments, the aqueous solution of hydrogel-forming peptides is buffered such that the concentration of the one or more isolated peptides in the aqueous solution of hydrogel-forming peptides in the combined aqueous solution of hydrogel-forming peptides and the active agent is at about 10 mM or more, or at about 15 mM or more. It was observed that the minimum concentration required for hydrogel formation is at about 10 mM. In preferred embodiments, the optimal concentration of the one or more isolated peptides in the combined aqueous solution of hydrogel-forming peptides and the active agent is at about 15 mM or more, but not more than 80 mM, for example, at about 20 mM or at about 30 mM. To prepare the combined aqueous solution, the stock solution is buffered, i.e. diluted in the suitable buffering agent, for example, phosphate buffers, such that the concentration of the one or more isolated peptides in the combined aqueous solution of the hydrogel-forming peptides and the active agent is at about 20 mM or at about 30 mM. In general, a higher concentration of the one or more isolated peptides in the aqueous solution of hydrogel-forming peptides is associated with shorter formation time, i.e. that hydrogel formation time is reduced with increasing concentrations of the isolated peptide in the combined aqueous solution of the hydrogel-forming peptides and the active agent.

In various embodiments, the aqueous solution/dispersion of the active agent is buffered such that the concentration of the active agent in the combined aqueous solution of hydrogel-forming peptides and active agent is at about 5 μg/mL or more, or at about 20 μg/mL or more, or at about 50 μg/mL or more. It was found that the optimal concentration of the active agent in the combined aqueous solution of hydrogel-forming peptides and active agent is at about 5 μg/mL or more for VEGF, at about 20 μg/mL or more for secretome, and in various embodiments, not higher than 500 μg/mL, for example, at about 6 μg/mL, 20 μg/mL, or at about 200 μg/mL. To prepare the combined aqueous solution of hydrogel-forming peptides and active agent, the active agent in a concentrated form is mixed with the aqueous solution of the hydrogel-forming peptides, such that the concentration of the active agent in the combined aqueous solution of the hydrogel-forming peptides and the active agent reaches its desired concentration, i.e. at about 6 μg/mL for VEGF, or at about 20 μg/mL, or at about 200 μg/mL for secretome.

While the indicated conditions in the method of manufacture is described in relation to the formation of a single-layered hydrogel, said conditions similarly apply for the formation of the individual hydrogel layers of the multi-layered composition or material, i.e. forming the addition layer(s) at the indicated conditions described above.

After hydrogel formation, the composition or material is a stable formulation, i.e. a composition or material comprising: (1) a hydrogel comprising the one or more isolated peptides of the present invention, and (2) the active agent encapsulated in the hydrogel. In various embodiments, the peptides forming the hydrogel are at least partially in the β-sheet conformation, preferably the anti-parallel β-sheet conformation. In some embodiments, the composition or material is a stable multi-layered hydrogel. Said composition or material may be packaged and the suitable forms and packaging options are well known to those skilled in the art.

As mentioned above, the inventors found that said composition or material, i.e. hydrogel comprising the encapsulated active agent exhibited enhanced structural integrity, enhanced shear modulus and reduced hydrogel degradation rates, suggesting that the incorporation of the active agent did not interfere with the gelation process and instead, enhanced the physio-chemical stability of the composition or material comprising the one or more isolated peptides of the present invention. The inventors further found that the encapsulated active agent exhibited a similar release profile regardless of the loading concentration of the active agent in the hydrogel, i.e. similar release kinetics was observed at the concentrations of about 6 µg/mL, at about 20 µg/mL, and at about 200 µg/mL of the active agent. In fact, the rate of release of the encapsulated active agent may be tailored by adjusting the concentration of the one or more isolated peptides in the composition or material, i.e. adjusting the degree of crosslinking and porosity of the hydrogel.

Methods for treating or diagnosing a condition or disease in a subject in need thereof are also disclosed, wherein the compositions or materials described above are used in treatment, prevention and/or diagnosis of a disease or condition. Such methods of treatment also include methods where a disease, condition or disorder is managed, for example, in that the symptoms or effects may be alleviated. Alternatively, the treatment may be prophylactic and aim at preventing a disease or condition from occurring. In various embodiments, the treatment methods also include methods for active wound management, for example, in (diabetic) chronic and non-healing wounds, where timely treatment and early intervention of wound healing is necessary to avoid infections or in extreme cases, lower the necessity for extremity amputations. It is further envisioned that the treatment method may include the encapsulation of active agents, i.e. vaccines, for the prevention of specific diseases.

In the above method, the composition or material described herein is a hydrogel comprising: (1) hydrogel-forming peptides comprising or consisting of one or more isolated peptides of the present invention, and (2) a pharmaceutical or diagnostic agent, wherein the pharmaceutical or diagnostic agent is encapsulated in the hydrogel, and wherein the peptides in the hydrogel are typically at least partially in a β-sheet conformation, preferably anti-parallel β-sheet conformation. In various embodiments, the hydrogel is administered to said subject. In various embodiments, the administration can be systemic or localized, i.e. topically or systemic, as described above. In some embodiments, the hydrogel is applied as a transdermal patch onto superficial and/or chronic wounds.

In the above method, said pharmaceutical or diagnostic agent is released in a controlled manner, wherein release occurs over a prolonged duration. Generally, the release occurs immediately upon the application of the hydrogel to the subject in need thereof, i.e. on the site of tissue injury. In preferred embodiments, release of the encapsulated active agent may be sustained for several hours, days or weeks. In various embodiments, the release kinetics of the encapsulated active agent can be controlled by adjusting the porosity of the hydrogel, i.e. adjusting the concentration of the one or more isolated peptides in the hydrogel.

In various embodiments, the subject may be a mammal, for example a human being. The administration and release mechanism of the encapsulated active agent are generally discussed above. In particular, the release of the encapsulated pharmaceutical or diagnostic agent is via diffusion where the encapsulated pharmaceutical or diagnostic agent diffuses in a controlled manner, through the hydrogel into the tissue injury site.

In a non-limiting embodiment of these methods for the treatment of a disease, condition or disorder, the subject is a human afflicted by a tissue injury, and the pharmaceutical agent is secretome derived from MSCs (ADMSCs). Administration of the hydrogel comprising one or more isolated peptides of the present invention is topical, i.e. transdermal, and release of secretome from the hydrogel is via diffusion, where secretome diffuses from the hydrogel to the tissue injury site. In such embodiments, the composition or material remains stable after hydrogel formation, for example, in a bandage or surgical wound packing material. Upon administration, encapsulated secretome is released in a controlled manner via diffusion, where secretome migrates through the fibrous network of isolated peptides of the hydrogel and into the tissue injury or wound site, i.e. from the region of high concentration to a region of low concentration. In particular, the rate of release of the encapsulated active agent can be controlled via the concentration of the one or more isolated peptides of the present invention.

In another non-limiting embodiment of these methods for the treatment of a disease, condition or disorder, the subject is a human afflicted by a tissue injury, and the pharmaceutical agent is VEGF. Administration of the hydrogel comprising one or more isolated peptides of the present invention is topical, i.e. transdermal, and release of VEGF from the hydrogel is via diffusion, where VEGF diffuses from the hydrogel to the tissue injury site to promote angiogenesis. In such embodiments, the composition or material remains stable after hydrogel formation, for example, in a bandage or surgical wound packing material. Upon administration, encapsulated VEGF is released in a controlled manner via diffusion, where VEGF migrates through the fibrous network of isolated peptides of the hydrogel and into the tissue injury or wound site, i.e. from the region of high concentration to a region of low concentration. In particular, the rate of release of the encapsulated active agent can be controlled via the concentration of the one or more isolated peptides of the present invention.

Additional applications of the compositions and methods will be identifiable by the person skilled in the art. The composition or material and methods herein disclosed are further illustrated in the following examples, which are provided by way of illustration and are not intended to be limiting the scope of the present disclosure.

EXAMPLES

Materials and Methods

Materials: Ac-GLYGGYGV-NH$_2$ (SEQ ID NO: 7) (GV8) peptide, Ac-GLYGGYGI-NH$_2$ (SEQ ID NO: 8) (GI8) peptide and Ac-GLYGGYGX-NH$_2$ (SEQ ID NO: 11) peptides (where X=V, L, A, F, S, and K) were purchased from GL Biochem (Shanghai) Ltd. Peptides were checked to be >98% purity via trace HPLC and LC/MS prior to use. All of the peptides were acetylated at the N-terminal and amidated at the C-terminal to prevent end-to-end charge interactions. $^{13}$C-$^{15}$N uniformly labeled GV8 crude peptide purchased from Cambridge Isotopes was purified to >95% purity via HPLC and checked with LC/MS prior to use.

Figure 2A:
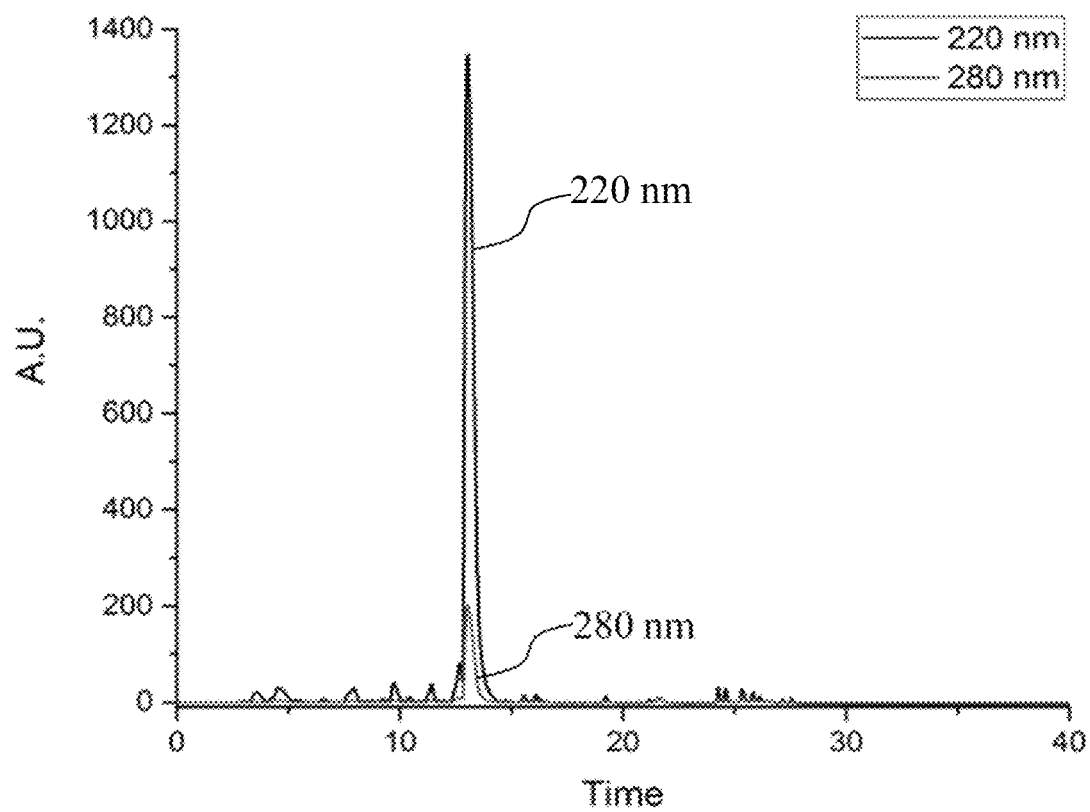
FIG. 2A. shows trace HPLC of the purified GV8 peptide at >95% purity.
Figure 2B:
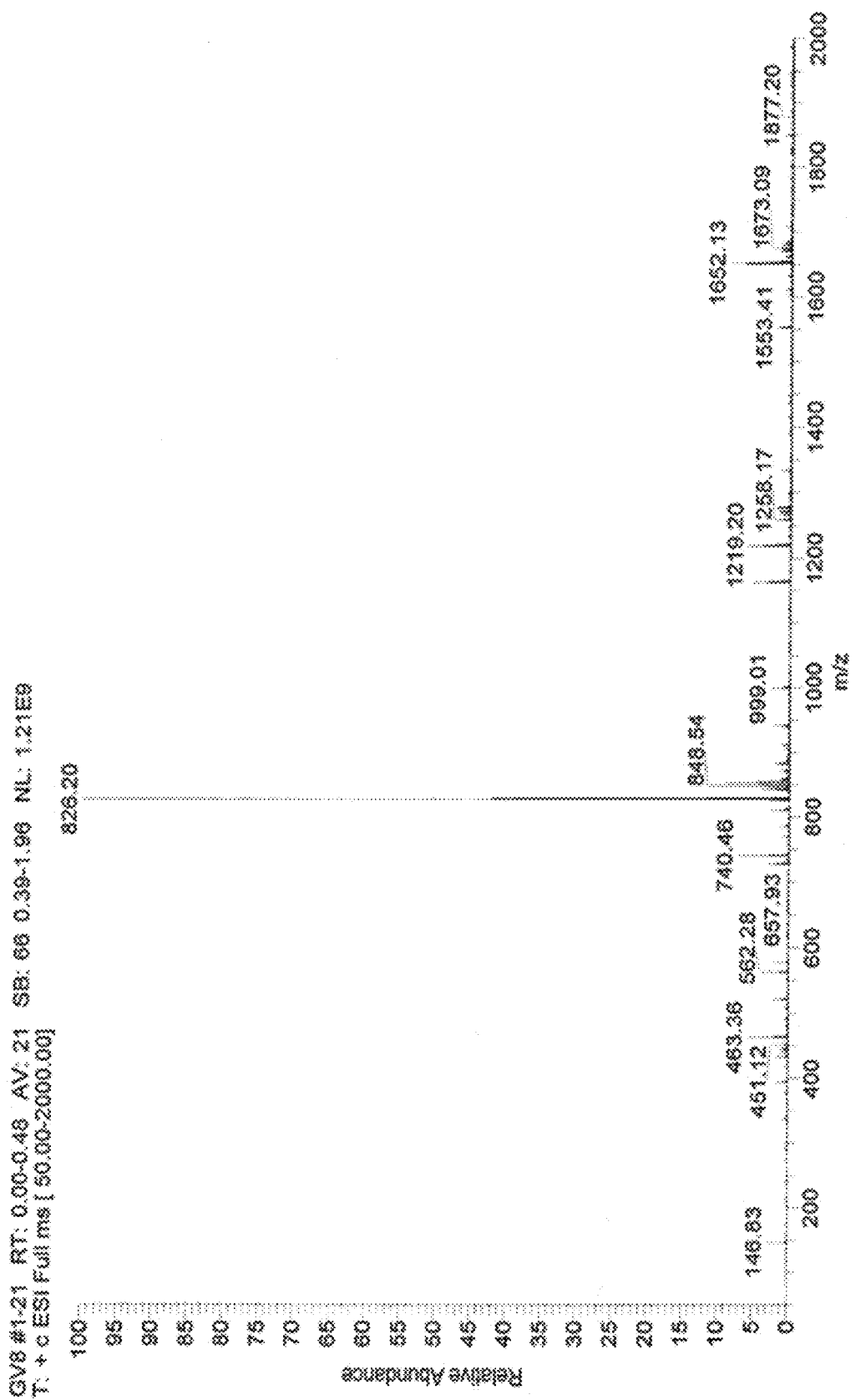
FIG. 2B. shows its respective mass spectra.

In some embodiments, the Ac-GLYGGYGV-NH$_2$ (SEQ ID NO: 7) (referred to as GV8 thereafter, i.e.) peptide was synthesized by solid phase peptide synthesis on rink amide solid support resins via Fmoc chemistry and cleaved in a 95% trifluoroacetic acid cocktail prior to precipitating in cold diethyl ether. The obtained peptide was purified to >98% purity with a C18 reversed phase preparative column prior to lyophilization in ACN/water mixture (<2 mg/mL) and stored at −20° C. until further usage. GV8 peptide purity and molecular weight confirmation was verified by HPLC trace analysis (FIG. 2A) and mass spectrometry (FIG. 2B), respectively.

UV-Vis spectroscopy: The peptides were dissolved in DI water at the respective concentrations and 100 µL was aliquoted into each well of a 96-well microtiter plate, with a minimum of 3 wells per condition. UV-Vis absorbance measurements at 550 nm were recorded on a Tecan infinite M200 Pro microplate reader at intervals of 30 min for the first 16 hours and subsequently at increased time intervals.

Peptide hydrogel (GV8): GV8 peptide was dissolved in DI water at the desired concentration (between 10 and 20 mM) and incubated at ambient temperature of 23° C. to 25° C. for at least 12 hours. For active agent encapsulation, GV8 hydrogels were prepared at concentrations of 20 mM to 50 mM with 1% Dimethylsulfoxide (DMSO) added per 10 mM of peptide in PBS with a pH range of 7.2 to 7.4 to form GV8 precursors, which gelate in a sealed environment under ambient temperature of 23° C. to 25° C. with a typical gelation time ranging from 5 h to 9 h (FIG. 1), depending on the concentration of the GV8 precursor. The GV8 precursors were prepared in various types of buffer solutions—such as DI water, Dulbecco's Modified Eagle's medium (DMEM), sodium acetate buffered solution with a pH range of 4 to 5, and/or buffered solutions with a pH ranging from pH 4 to 7.4.

Peptide hydrogel (GI8): GI8 peptide was dissolved in DI water at the desired concentration (between 10 and 20 mM) and incubated at ambient temperature of 23° C. to 25° C. for at least 12 hours. GI8 hydrogels were prepared at concentrations of 20 mM to 50 mM with or without 1% Dimethylsulfoxide (DMSO) added per 10 mM of peptide in PBS with a pH range of 7.2 to 7.4 to form GI8 precursors, which gelate in a sealed environment under ambient temperature of 23° C. to 25° C. with a typical gelation time ranging from 2 h to 7 h (FIG. 1), depending on the concentration of the GI8 precursor. The GI8 precursors were prepared in various types of buffer solutions—such as DI water, Dulbecco's Modified Eagle's medium (DMEM), sodium acetate buffered solution with a pH range of 4 to 5, and/or buffered solutions with a pH ranging from pH 4 to 7.4.

Figure 3:
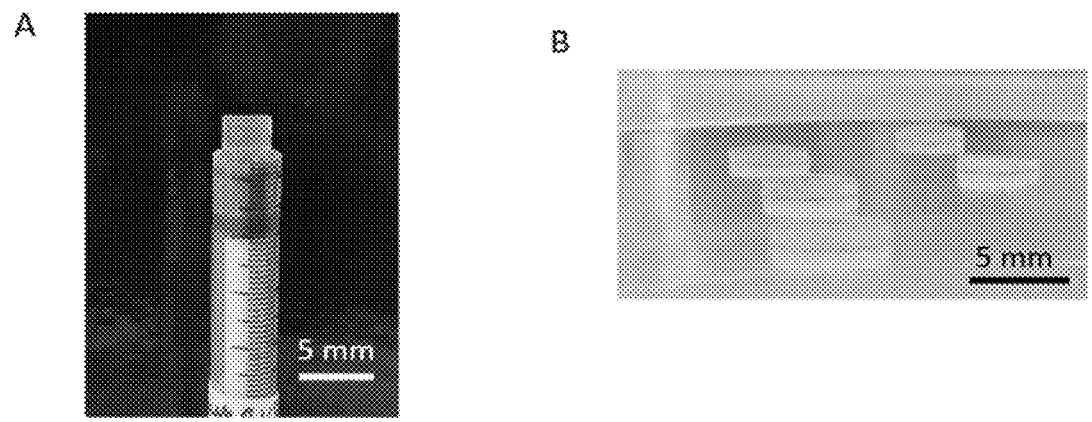
FIG. 3. GV8+ hydrogels preparation. (A) GV8+ hydrogels were prepared in a pre-cut 1 mL syringe and (B) disc-shaped hydrogels with flat surface prepared on transparency films.

Secretome-loaded GV8 hydrogels (GV8+): Secretome-loaded GV8 hydrogels (GV8+) were formed by pre-mixing secretome in the GV8 precursor prior to gelation process. Secretome was derived from adipose MSCs (ADMSC). To incorporate secretome (or various active agents) in the GV8 peptide hydrogel, the following steps were employed—(i) the GV8 peptide was first dissolved in a small volume of 99.9% DMSO (to make up a 3% v/v final volume); (ii) PBS (pH 7.2) and secretome were gently added to the mixture with consistent gentle agitation, with a final GV8 peptide concentration ranging between 20 mM to 50 mM, and secretome concentration ranging between 20 µg/mL to 200 µg/mL; (iii) the mixture prepared at step (ii) was left to gelate in a sealed environment under ambient temperature of 23° C. to 25° C. For example, a 3% v/v DMSO-GV8-peptide-secretome mixture with a final peptide concentration of 30 mM and final secretome concentration of 200 µg/mL will gelate within 5 h; and (iv) the GV8+ hydrogels were further incubated for a minimum of 12 h in total to ensure that the GV8+ hydrogels reach a maximum gel stiffness (or storage modulus, G') prior to handling and application (FIG. 3).

VEGF-loaded GV8 hydrogels (GV8+ VEGF): VEGF-loaded GV8 hydrogels (GV8+ VEGF) were formed by pre-mixing VEGF in the GV8 precursor prior to gelation process. To incorporate VEGF (or various active agents) in the GV8 peptide hydrogel, the following steps were employed—(i) the GV8 peptide was first dissolved in a small volume of 99.9% DMSO (to make up a 3% v/v final volume); (ii) PBS (pH 7.2) and VEGF were gently added to the mixture with consistent gentle agitation, with a final GV8 peptide concentration at 30 mM, and VEGF concentration at 6 µg/mL (iii) the mixture prepared at step (ii) was left to gelate in a sealed environment under ambient temperature of 23° C. to 25° C. For example, a 3% v/v DMSO-GV8-peptide-VEGF mixture with the final peptide concentration of 30 mM and final VEGF concentration of 6 µg/mL will gelate within 2 h; and (iv) the GV8+ VEGF hydrogels were further incubated for a minimum of 12 h in total to ensure that the GV8+ VEGF hydrogels reach a maximum gel stiffness (or storage modulus, G') prior to handling and application (FIG. 3).

CD spectroscopy: GV8 and GI8 peptides were dissolved at 20 mM concentration in DI water and spectra were collected using a 0.2 mm path length quartz cuvette. Data acquisition was performed using AVIV 420 Circular Dichroism (New Jersey, USA) spectrometer. A quartz sandwich cuvette with optical path length of 0.2 mm was used for all data collection and the edges of the cuvette was sealed with parafilm to prevent loss of liquid. Data were acquired over a wavelength range of 190 nm to 260 nm and acquisition parameters were 0.5 nm wavelength steps with an averaging time of 0.1 s, 1.00 nm bandwidth, and readings were averaged over 3 scans. Obtained spectra were smoothed at 12 pts via adjacent-averaging method (ensuring that no visible existing peaks were removed or artefacts introduced) and plotted via OriginPro 9.1.

For characterization of GV8 and GV8+ hydrogels, GV8 and GV8+ hydrogels were dissolved at 30 mM concentration in DI water with secretome concentrations of 20 µg/mL and 200 µg/mL and similar CD spectroscopy measurements were performed.

FTIR spectroscopy: Attenuated total reflection fourier-transform infrared (ATR-FTIR) spectroscopy of lyophilized GV8 and GI8 samples were performed on a Bruker Vertex 70 (Massachusetts, USA) equipped with a PIKE Technologies MIRacle attenuated total reflection (ATR) ZnSe-Diamond 3-reflection accessory and a $LN_2$ cooled MCT detector. Scans were obtained at ambient temperature over the range of 4000 to 750 $cm^{-1}$ with a resolution of 2 $cm^{-1}$, averaged over 128 scans. GV8 and GI8 peptide solutions were prepared at 20 mM concentration in separate vials of 20 µL and snap freezed by dipping the vials in liquid $N_2$ for 5 minutes at the stipulated time points and lyophilized immediately. All spectra processing were performed on OPUS 6.5, and processed in the sequence of water vapor subtraction, baseline correction, then normalized using amide I band. Amide I band was deconvoluted by secondary derivation, with peak fitting performed using 100% Gaussian curves with individual FWHM kept relatively consistent. The deconvoluted peaks were assigned to β-sheet, unordered, helix and turns or $3_{10}$ structures (H. Y. Yang et al. *Nat. Protoc.* 2015, 10, 382; D. Wilson et al. *Biophys. J.* 2000, 78, 2690; E. Vass et al. *Chem. Rev.* 2003, 103, 1917; J. Kong et al. *Acta. Bioch. Bioph. Sin.* 2007, 39, 549).

Cryo-EM: GV8 peptide was dissolved at a concentration of 20 mM and incubated for 3 hours. Copper grids with Ultrathin C Film on Lacey Carbon support film was plasma-treated with JEOL DATUM HDT-400 for 300 s to increase hydrophilicity of grid surfaces to allow aqueous samples to adhere and spread. Vitrified samples were prepared using Gatan Cryoplunge™3 (Cp3). 4 µL of sample was pipetted onto each plasma-treated copper grid and blotted for 5 seconds followed by vitrification in liquid ethane at −180° C. All micrographs were taken in bright-field mode with objective aperture inserted. Imaging was carried out with energy filtered Carl Zeiss TEM. LIBRA® 120 with in-column Omega spectrometer and operated an acceleration voltage of 120 kV and the sample temperature was maintained below −180° C. during imaging.

SEM: Peptide hydrogel was snap freezed by dipping into liquid $N_2$ for at least 5 minutes. The frozen hydrogel was then cryo-fractured with tweezers to expose the porous cross-section and the fractured surfaces were placed face-up on carbon tape and lyophilized immediately. Samples were Platinum-coated below 5 Pa, at 20 mA for 30 s and imaging was performed using JEOL JSM-FESEM 7600F (Massachusetts, USA), at SEI-mode, 5 kV, and 92 µA emission current.

AFM: 10 µL of GV8 peptide at 20 mM concentration was deposited onto freshly cleaved mica and air-dried overnight. AFM images were obtained on Asylum Cypher S AFM (Oxfordshire, UK) in tapping mode using Nanoworld NCSTR silicon nitride soft-tip cantilevers (Rf=160 kHz, k=7.4 N/m). All images were flattened to remove background curvature using Igor Pro software and no further image processing was carried out.

Rheology: Rheological measurements were performed at ambient temperature on Anton Paar MCR501 rheometer with a parallel plate PP10 geometry. 5 different concentrations (10 mM, 12 mM, 15 mM, 18 mM and 20 mM) of GV8 hydrogels were prepared in DI water, each pipetted into 1 mL syringes with nozzles removed, then left overnight to gelate. The hydrogel was extruded from the syringes and cut to 1 mm to 2 mm thick slices with a sterile blade and placed on the rheometer plate for measurements. Strain sweeps were first conducted at constant frequency of 1 Hz, from 0.1% to 10% strain to identify the LVE and 0.25% strain was selected for subsequent frequency sweeps that were conducted from 0.01-100 Hz.

Rheological characterizations of GV8 hydrogels, GV8+ hydrogels and GV8+ VEGF hydrogels (prepared in pre-cut 1 mL syringes) were conducted at ambient temperature on Anton Paar MCR501 rheometer with a parallel plate PP10 geometry. Strain sweeps were performed at constant frequency (1 Hz) to identify their LVE region, followed by frequency sweeps from 0.01 to 100 Hz to obtain the storage (G') and loss (G") modulus for the GV8, GV8+ hydrogels, GV8+ VEGF hydrogels at a constant strain value from the LVE.

NMR: All solution state NMR experiments were carried out on a Bruker 700 MHz spectrometer equipped with a cryoprobe. NMR data were processed with TOPSPIN (Bruker), then analysed using Sparky (W. Lee et al. *Bioinfo.* 2015, 31, 1325) programs. 0.5 mM or 20 mM GV8 peptides were dissolved in water, pH 6.8 with 10% $D_2O$ for deuterium lock and DSS for signal reference. Two dimensional (2D) $^1H$-$^1H$ TOCSY and NOESY spectra were acquired with 80 ms and 200 ms mixing times, respectively. In order to monitor hydrogel formation, 1D $^1H$ spectrum and a series of 2D $^1H$-$^1H$ NOESY spectra were recorded every four hours for 20 hours using the 20 mM peptide solution. For H/D exchange experiments, 0.5 mM and 20 mM peptide samples were dissolved in 100% $D_2O$ and 2D $^1H$-$^1H$ TOCSY spectra were recorded at 30 min intervals. The extrinsic exchange rates were obtained by fitting the peak intensity vs. time to a single-exponential decay equation. The protection factor were calculated as the ratio of intrinsic exchange rates (calculated from SPHERE (Bai et al. *Proteins.* 1993, 17, 75)) to the extrinsic exchange rates. A protection factor above 30 is indicative of stable hydrogen bonds, while values between 10 to 30 indicate an intermediate range of hydrogen bond strength (T. M. K. Kuwata et al. *PNAS. USA.* 2003, 100, 14790). Amide temperature coefficients were also determined by recording 1D $^1H$ spectra of 0.5 mM and 20 mM GV8 peptide at 298 K, 303 K, 308 K and 313 K. Amide proton chemical shift deviations were fitted linearly against temperature and the temperature coefficients were calculated as σδHN/ΔT (ppb $K^{-1}$).

Solid state NMR experiments were carried out on a Bruker 600 MHz spectrometer equipped with a 1.7 mm Magic Angle Spinning (MAS) probe. The MAS spinning frequency was 13,333 Hz. 20 mM of $^{13}C$-$^{15}N$ labeled GV8 peptide was dissolved in water, pH 6.8 and allowed to incubate overnight for hydrogel formation. Sample was loaded in a 1.7 mm thin wall zirconia rotor (Bruker) manually and the rotor was spun at 70000 rpm for 30 min by ultracentrifugation (Beckman Proteomelab XL, IN, USA). 2D $^{13}C$-$^{13}C$ DARR spectra were recorded over contact times ranging from 50 to 400 ms. 3D NCACX, NCOCX and CANcoCX experiments were also recorded with 50 ms contact time.

NMR structure calculation: The structure calculations were carried out using the CYANA 2.1 program. The monomeric conformation of GV8 was calculated using the intensities of $^1H$-$^1H$ NOE cross peaks that were classified as strong, medium, and weak and translated to upper bound distance limits of 2.5, 3.5, and 5.0 Å. The dihedral Φ and Ψ angles were constrained between −120° to −30° and −120° to 120° as suggested in the CYANA program files. Out of the 100 structures generated, the 10 lowest energy structures were used for more analysis. The dimer structures of GV8 was also calculated using the same constraints as monomeric structure calculation. The two monomeric units were linked by five glycine linkers. The structure of hydrogel was calculated using $^{13}C$-$^{13}C$ dipolar contacts derived from solid state NMR spectra. All of the conformations were validated using PROCHECK (R. A. Laskowski et al. *J. Appl. Crystallography.* 1993, 26, 283). For structure calculation from ssNMR, a total of 47 intra-residue and sequential dipolar constraints were used. The long-range dipolar contacts included in the structure calculation were cross-strand contacts used to generate a dimeric conformation.

SAXS and WAXS: Small- and wide-angle X-ray scattering (SAXS and WAXS) experiments were performed using Rigaku MicroMax-002+ equipped with a microfocused beam (40 W, 45 kV, 0.88 mA) with the $\lambda_{Cu\ K\alpha}$=0.15418 nm radiation collimated by three pinhole collimators (0.4, 0.3, and 0.8 mm). The SAXS and WAXS intensities were collected by a two-dimensional Triton-200 gas-filled X-ray detector (20 cm diameter, 200 µm resolution) and a two-dimensional Fujifilm BAS-MS 2025 imaging plate system (15.2×15.2 $cm^2$, 50 µm resolution), respectively. An effective scattering vector range of 0.05 $nm^{-1}$<q<25 $nm^{-1}$ was obtained, where q is the scattering wave vector defined as q=4π sin θ/$\lambda_{Cu\ K\alpha}$ with a scattering angle of 2θ.

H-REMD simulations: Hamiltonian replica exchange molecular dynamics (H-REMD) simulations (G. Bussi. *Mol. Phys.* 2014, 112, 379) was performed for the dimer, tetramer and octamer of the Ac-GLYGGYGV-NH$_2$ (SEQ ID NO: 7) (GV8) peptide for 200 ns each. The CHARMM 36 mm force field parameters (J. Huang et al. *J. Comput. Chem.* 2013, 34, 2135) were applied to peptides, and the dimer, tetramer and octamer were put in a cubic box with TIP3P waters (W. Jorgensen et al. *J. Chem. Phys.* 1983, 79, 926) and 0.15 M NaCl. The minimum distance between the peptides and the box edge was larger than 1.5 nm. The dimer, tetramer and octamer systems have 8, 12 and 16 replicas from 300 K to 600 K, respectively, and each was simulated for 200 ns. The trajectories were saved every 2 ps.

Conventional MD simulations: Conventional MD simulations were performed for the 40-mer two-layer anti-parallel β-sheet model for 100 ns using the AMBER 16 software (D. A. Case et al. *J. Comput. Chem.* 2005, 26, 1668) together with the AMBER14SB force field. SHAKE algorithm (J. P. Ryckaert et al. *J. Comput. Phys.* 1977, 23, 327) was used to constrain all bonds involving hydrogens and electrostatic interactions were treated by the particle mesh Ewald sum method (U. Essmann et al. *J. Chem. Phys.* 1995, 103, 8577) with a 8 Å cutoff for non-bonded interactions in direct space. The model was solvated in a rectangular box filled with TIP3P waters (W. Jorgensen et al. *J. Chem. Phys.* 1983, 79, 926), with an at least 1.0-nm distance between the peptides and the box edge. The whole system was first energy-minimized, with a series of position restraints on the solute (all heavy atoms, backbone atoms, and Cα atoms). The simulation was continued for 100 ns at 1 bar and 298.15 K.

Release profile of dextran and secretome: Hydrogels were pre-mixed with known concentrations of FITC-tagged dextran and FITC-tagged secretome in the GV8 precursor prior to gelation to measure their release profiles. Precursor mixtures were pipetted into 96-well microplates at 90 μL/well for gelation, and incubated with 100 μL PBS solution to allow FITC-tagged molecules to be released into solution. 100 μL of the PBS solution was collected and measured for FITC fluorescence intensity at different time points, and replaced with an equal volume of fresh PBS solution.

Degradation of GV8 and GV8+ hydrogels: Hydrogel degradation was characterized with two methods, namely, the decrease in (i) storage modulus (G'); and ii) wet weight. GV8 and GV8+ hydrogels were incubated in PBS solution and their storage modulus (G') and wet weight was measured at various time points at ambient temperature on Anton Paar MCR501 rheometer with a parallel plate PP10 geometry and a weighing balance, respectively.

Cytocompatibility assay: GV8 hydrogels of 30 mM GV8 peptide concentration were tested for their cytocompatibility with HaCaT keratinocytes and HDF. HaCaT keratinocytes and HDF were seeded separately onto GV8 hydrogels which were pre-formed in tissue culture plate (TCP) wells and allowed to attach overnight. Cell viability was monitored for a further 24 h and 72 h.

Cell migration and angiogenesis assay: For the HaCaT keratinocytes cell migration assays, GV8+ hydrogels were prepared in pre-cut 1 mL syringe (FIG. 3A), extruded and cut for use. For the HaCaT keratinocyte cell migration assays, GV8+ hydrogels were prepared in pre-cut 1 mL syringe (FIG. 3A), extruded and cut for use. HaCaT were grown to confluence in 24-well microplates, followed by serum-free starvation for 18 h prior to scratching using a pipette tip to create a wound. After wounding, cells were washed twice with serum-free media to remove cell debris. The prepared GV8+ hydrogel was then placed in a transwell before introducing to the wounded HaCaT keratinocytes, in which the effect of secretome on keratinocytes migration was evaluated. At different pre-determined time points (8, 24 and 48 h), the wound gap was imaged using a Zeiss PrimoVert microscope, and the percentages of the open wound area were analyzed using ImageJ. For the CAM angiogenesis assays, 20 μL of GV8+ and GV8+ VEGF precursors were sandwiched between two punched-out transparency films (5 mm diameter) to form a disc-shaped hydrogel with a flat surface (FIG. 3B). In addition, standard CAM assays were performed using fertilized chicken eggs to test for angiogenic activity. Hydrogel samples comprising secretome and/or VEGF were placed on the top of the CAM after 11 d of ex-ovo embryo survival and left to incubate at 37° C. for 3 d. Blood vessels proximal to hydrogel samples were imaged and analyzed using ImageJ.

Cell proliferation assay: HaCaT keratinocyte cells between passage 10 to 12 were used to determine the effect of ADMSCs secretome concentration on cell proliferation. Secretome of different concentrations were added to uniformly-seeded and 24 h serum-starved HaCaT keratinocyte cells for 2 d to stimulate proliferation. HaCaT proliferation was measured with an alamarBlue™ assay (R7017, Sigma). HaCaT keratinocyte cells were incubated with alamarBlue™ solution for 4 h prior to transferring said solution into a 96-well opaque black microplate (07-200-590, Corning) to measure fluorescence readout at Ex/Em of 530 nm/575 nm.

In vivo assay: To investigate the wound healing property of the hydrogels, 30 μL GV8 and GV8+ hydrogels loaded with 200 μg/mL ADMSC secretome were applied to topical puncture wounds on non-diabetic mice models, and monitored for a period of 2 d, 5 d and 7 d at various points in time.

All measurements were triplicated (n=3) with repeated measurements performed on fresh samples.

Figure 4A:
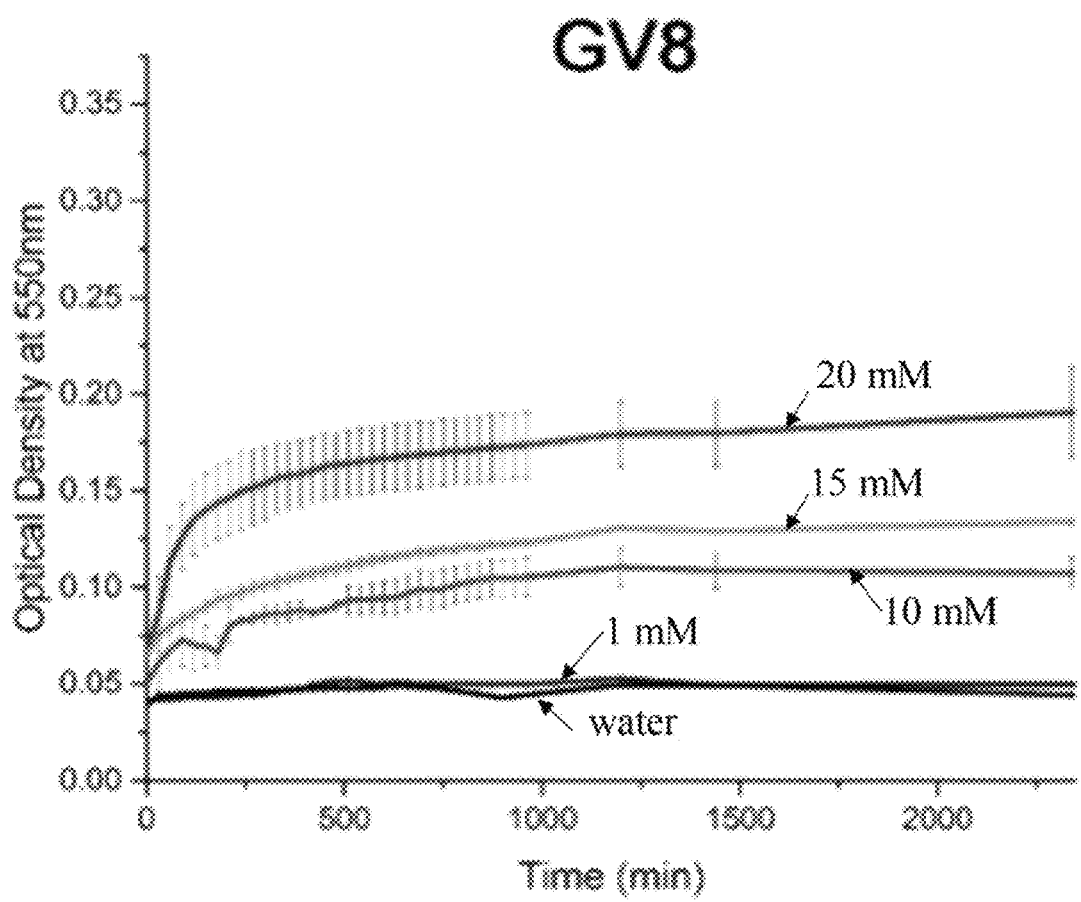
FIGS. 4A-4L. Gelation properties of peptides investigated.
Figure 4B:
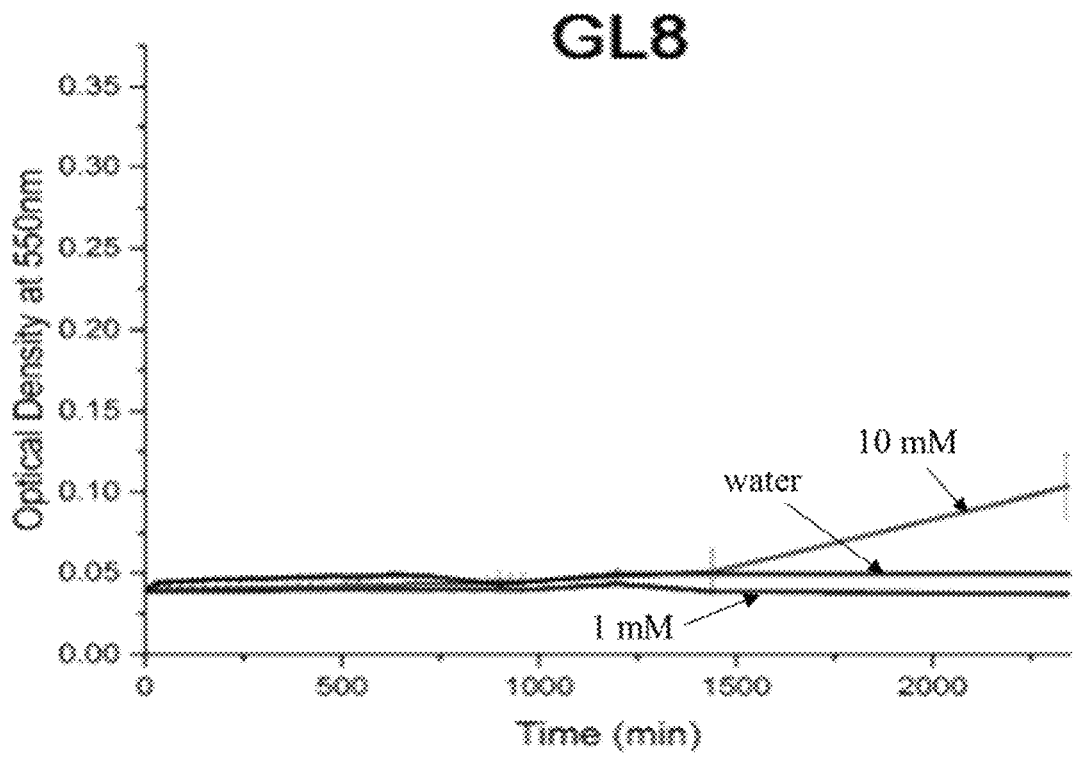
Figure 4C:
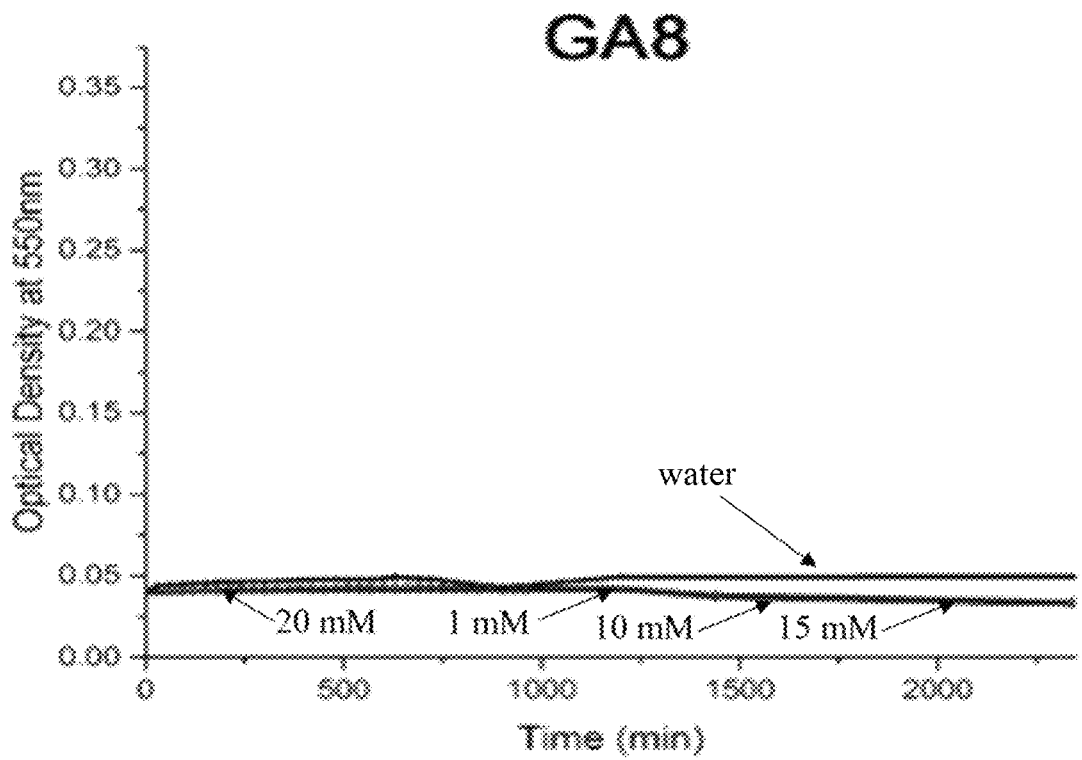
Figure 4D:
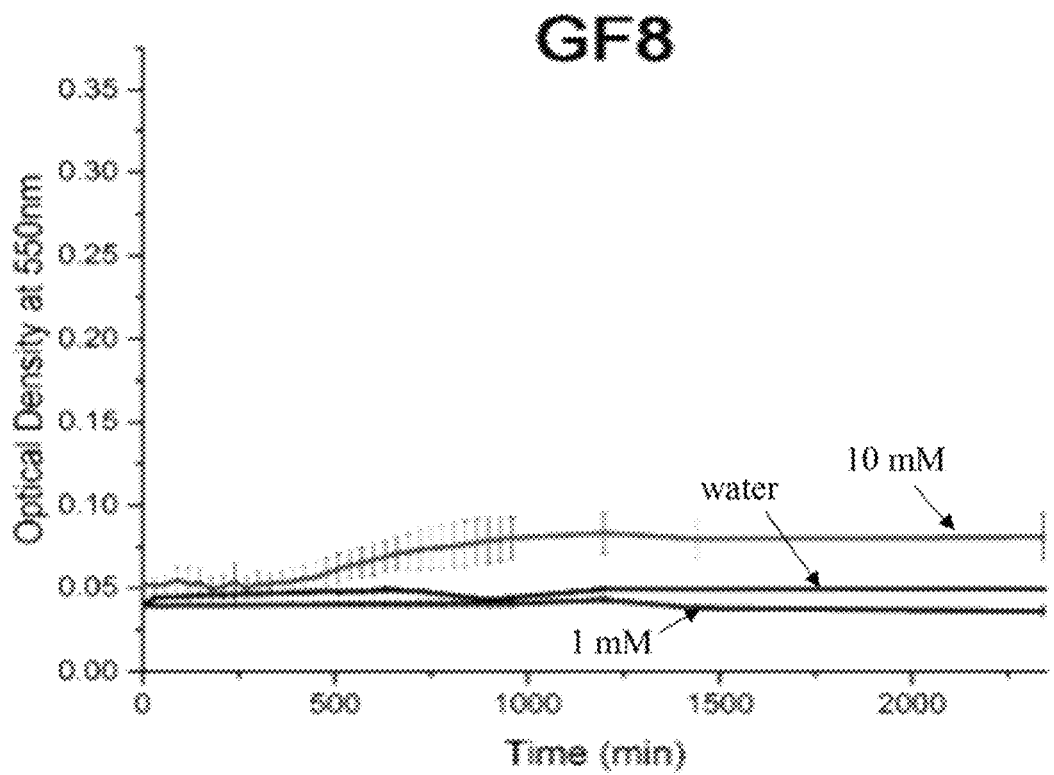
Figure 4E:
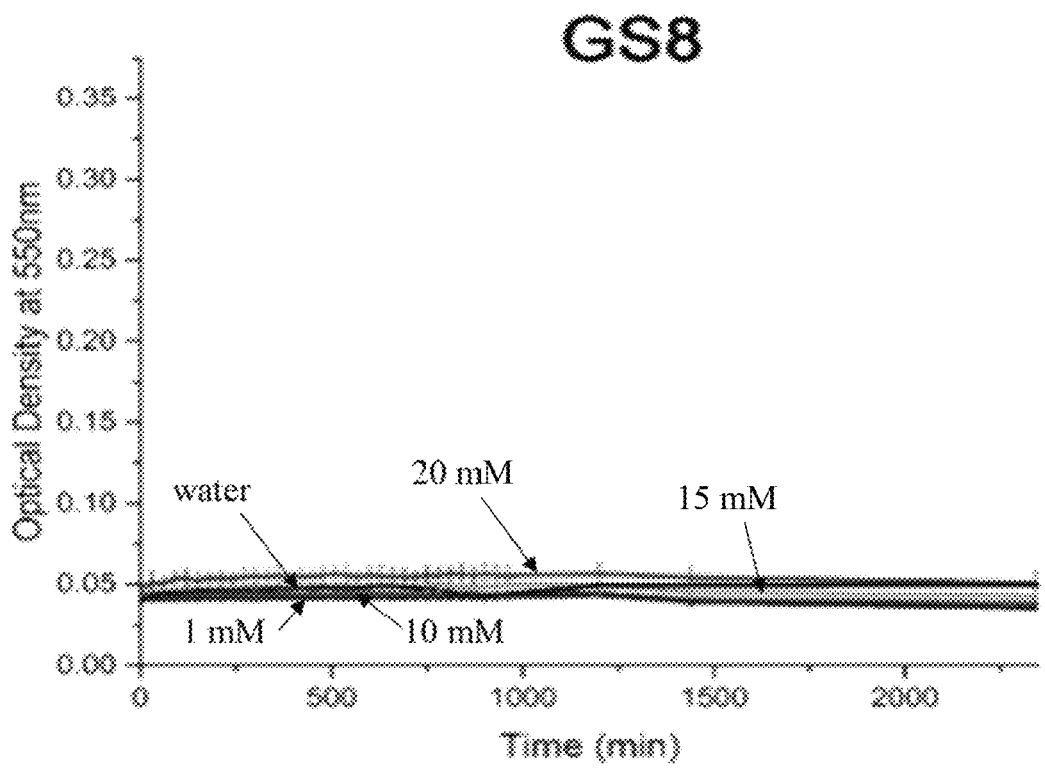
Figure 4F:
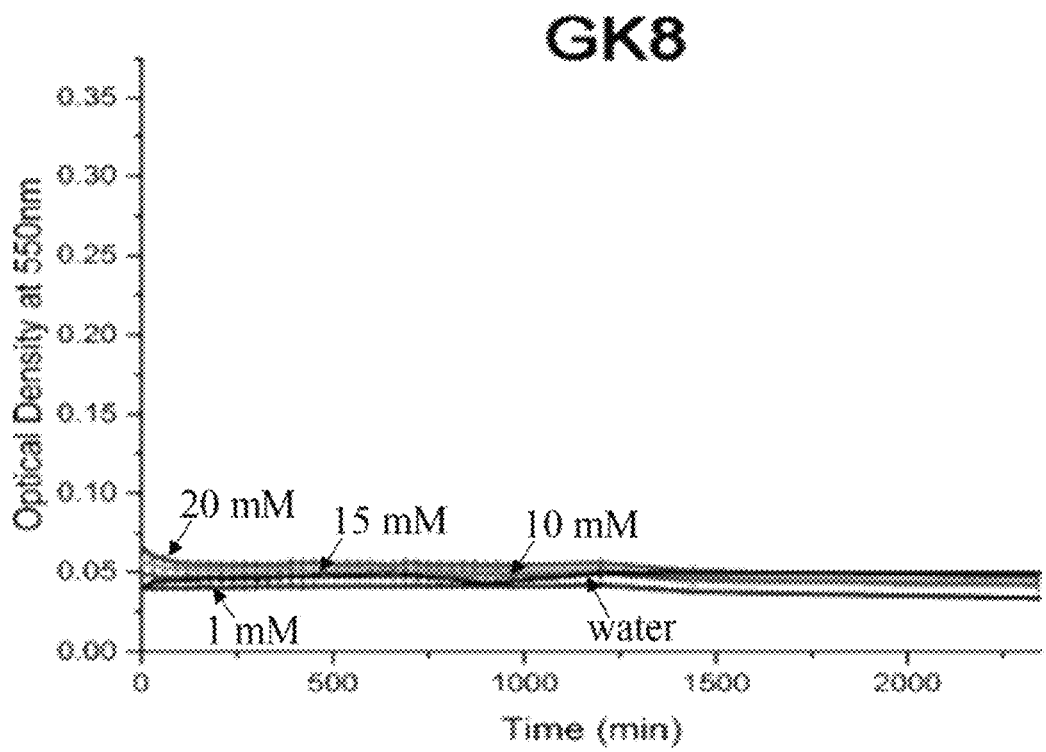
Figure 4G:
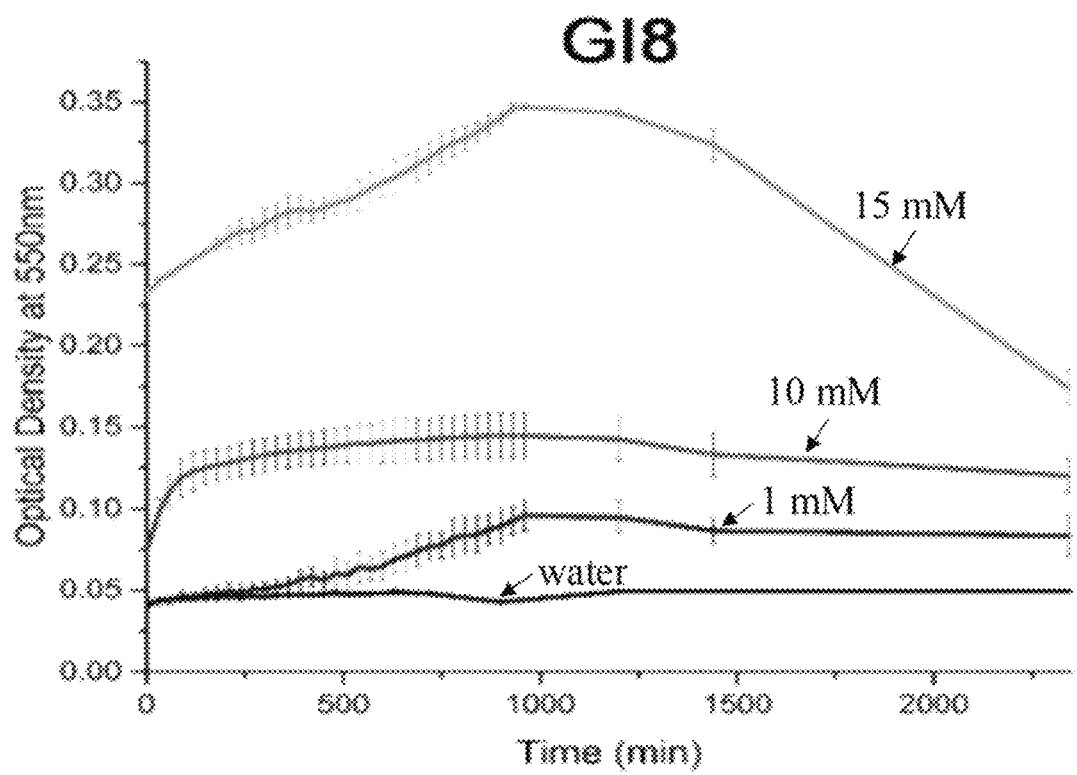
Figure 4H:
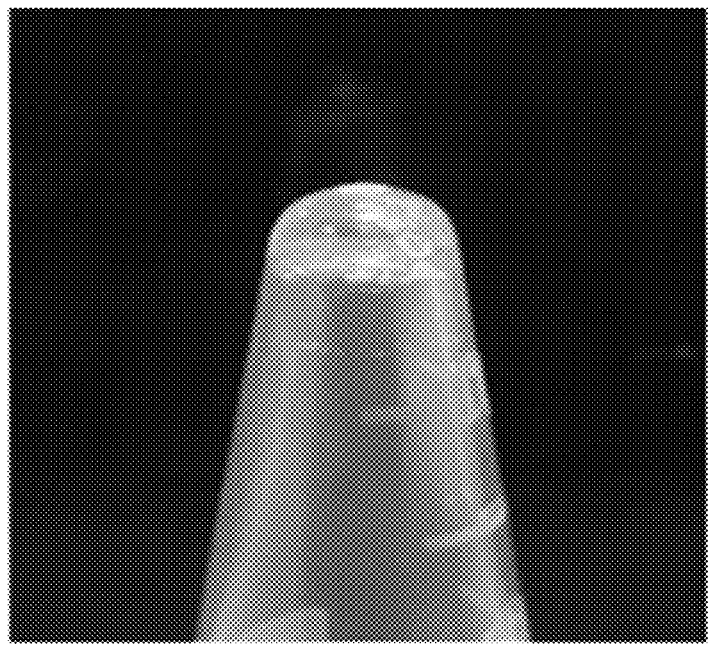
Figure 5A:
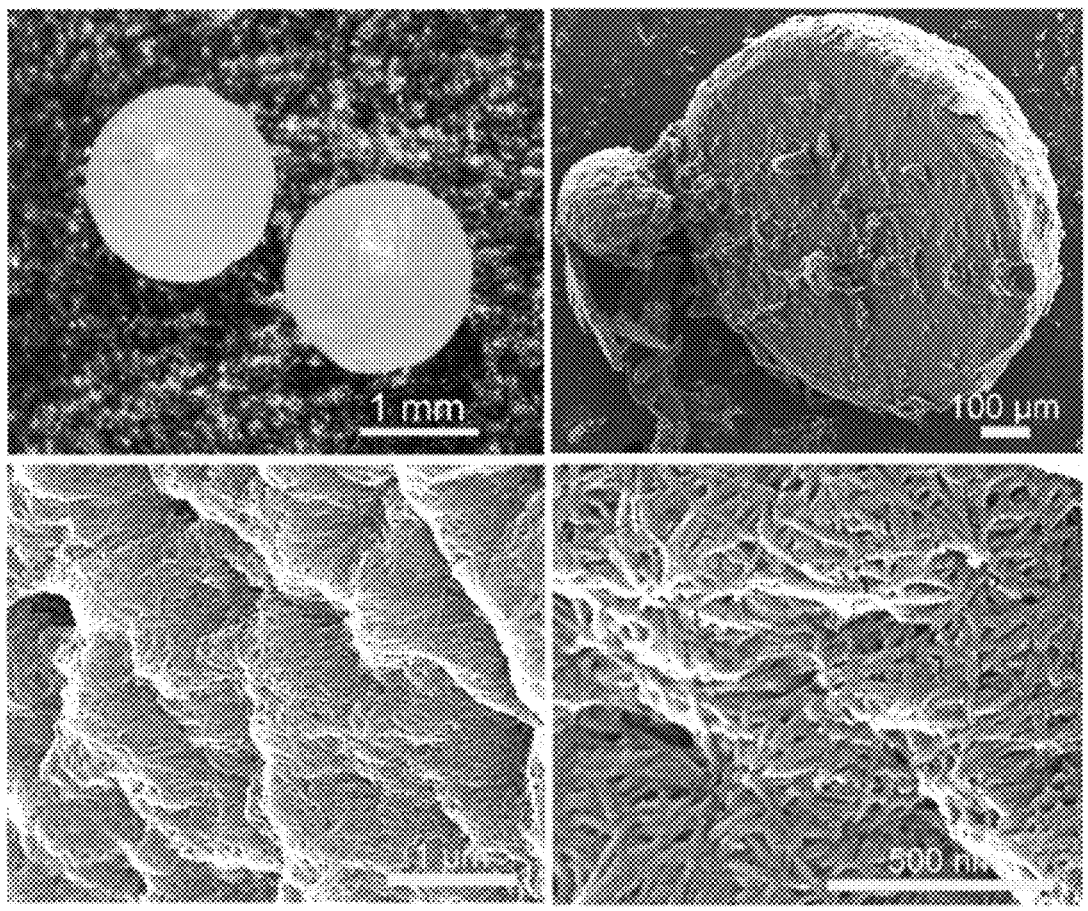
FIG. 5A-5B. Bead-like structures formed by GL8 peptide via self-assembly in DI water.
Figure 5B:
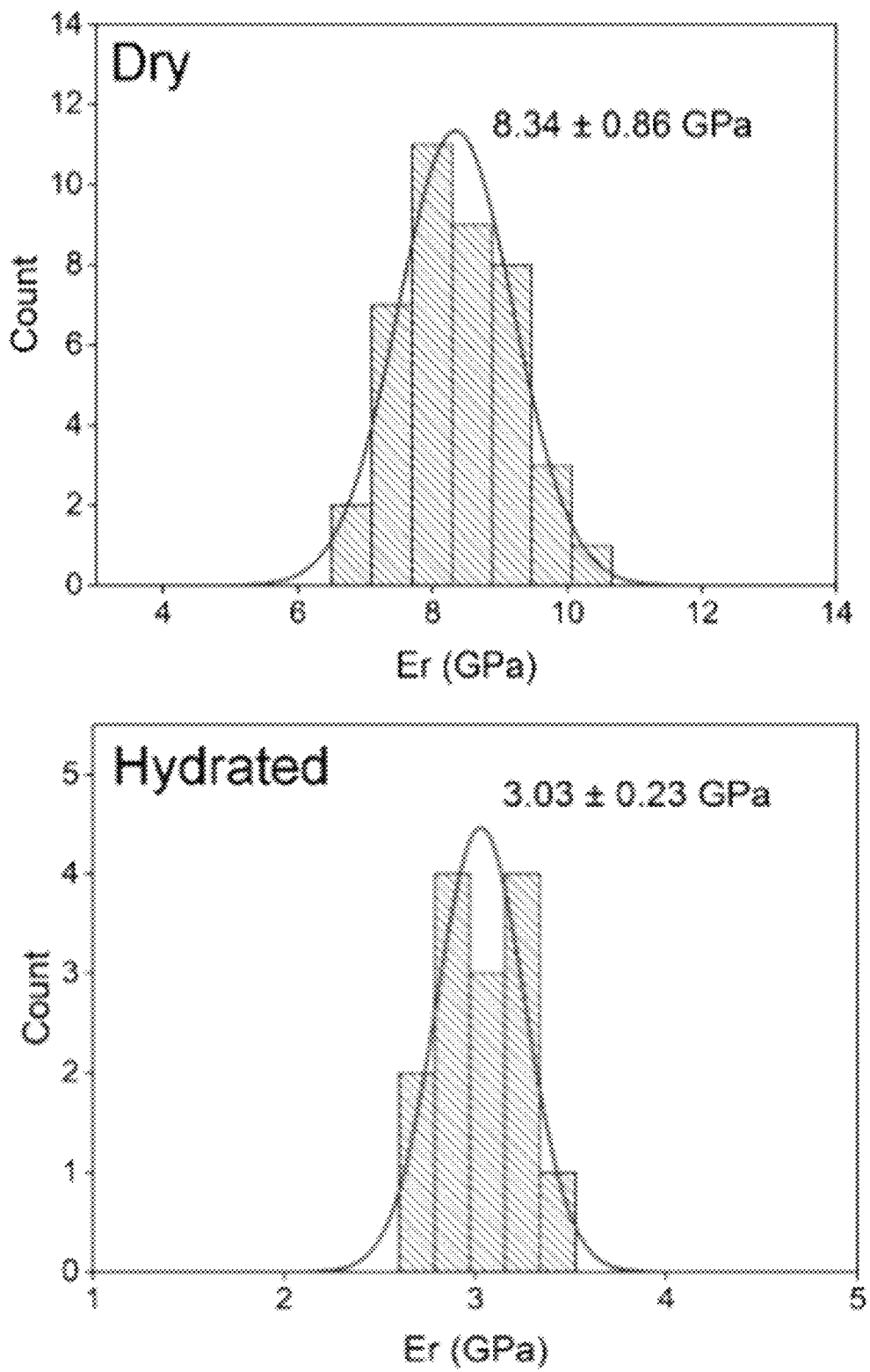

1. Example 1: Characterization of the GV8 vs. GX8 Peptides and the GV8 Hydrogel, and of the GI8 vs. GI8 Peptides and the GI8 Hydrogel 1.1 Peptide Gelation The GV8 peptide hydrogel was obtained by simple incubation of the peptide in DI water, with gelation occurring at peptide concentrations ranging from 10 to 20 mM and a concentration-dependent gelation time between 5 to 9 hours. The minimal critical gelation concentration ($c_{gc}$) in water was 10 mM, below which we did not observe gelation. We monitored the gelation kinetics by measuring the absorbance ($OD_{550\ nm}$) of the peptide solutions at 550 nm (FIG. 4A-G) whereby $OD_{550\ nm}$ increased during the gelation process and plateaued once gelation was complete (H. G. Zhao et al. *Biomed. Mater.* 2008, 3, 015001). We also attempted to mutate the C-terminus Val residue with Leu (GL8), Ala (GA8), Phe (GF8), Ser (GS8) or Lys (GK8) but these peptides were not able to form gels in water, illustrating the key role of terminal Val in gelation as corroborated by NMR studies. GF8 and GI8 peptides (FIGS. 4D and 4G) remained in solution with some gel-like formation observed overtime, whereas GL8 self-assembled into large (mm-size) and stiff beads (FIG. 5). Specifically, GI8 peptides were observed to self-assemble in water and formed hydrogels after 1 h incubation time (FIG. 4H).

1.2 Macro and Micro-Gel Structure

Figure 6A:
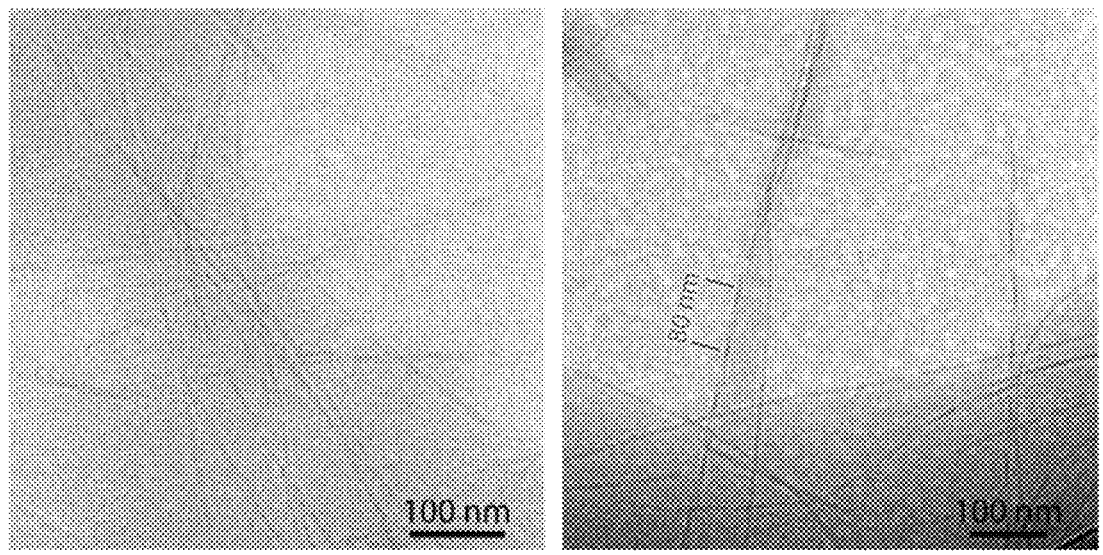
FIG. 6A-6F. Structural features and physico-chemical properties of GV8 peptide hydrogel observed with time-series spectroscopy measurements during gelation.
Figure 6B:
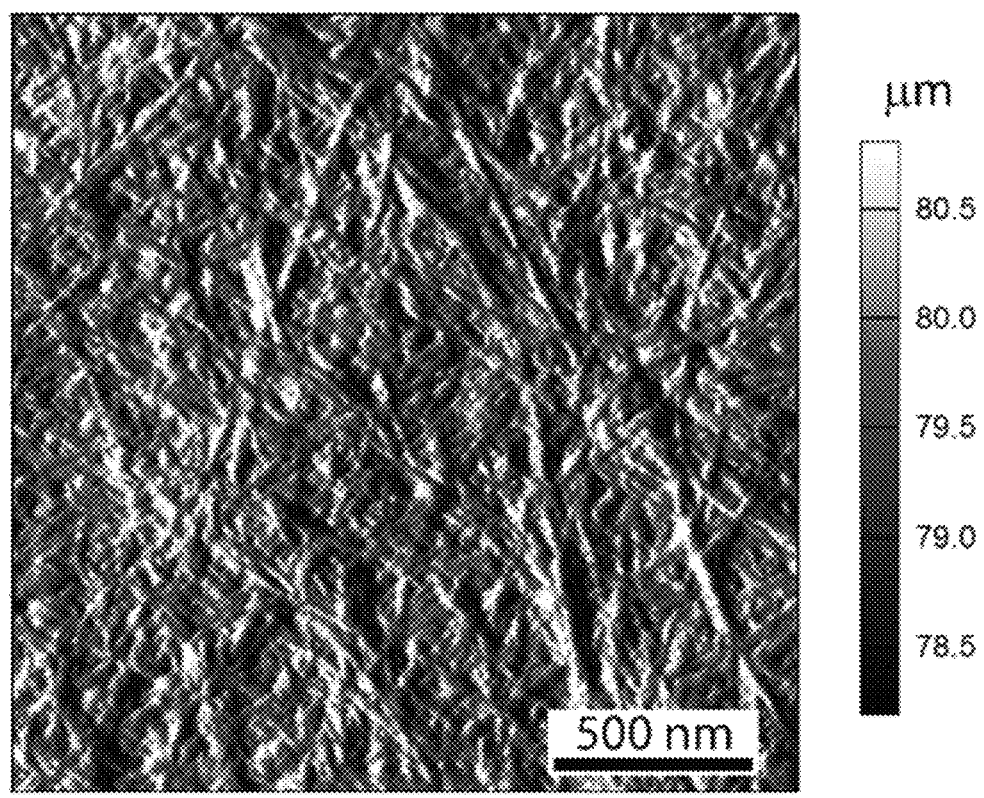
Figure 6C:
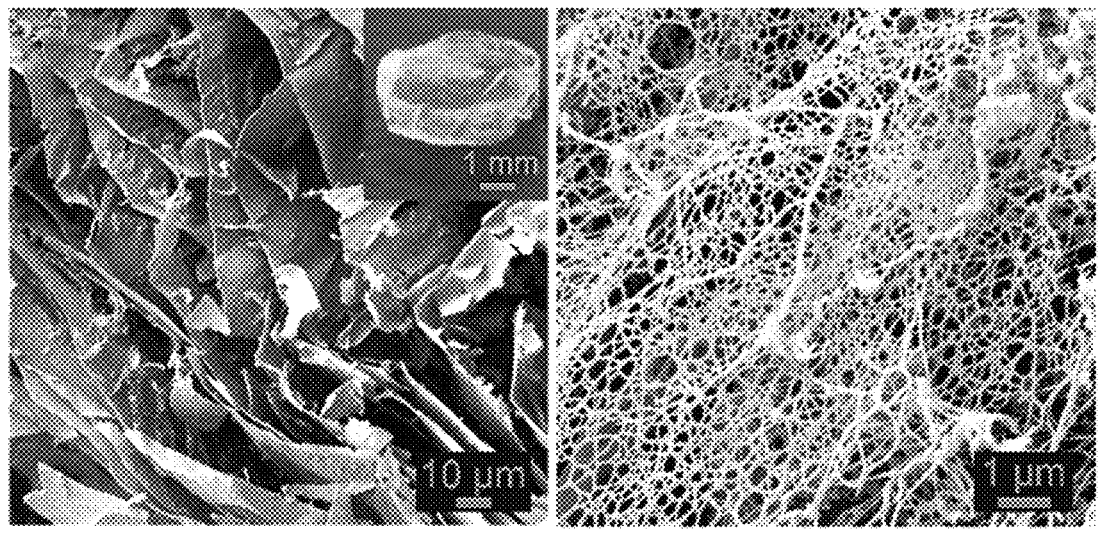
Figure 7:
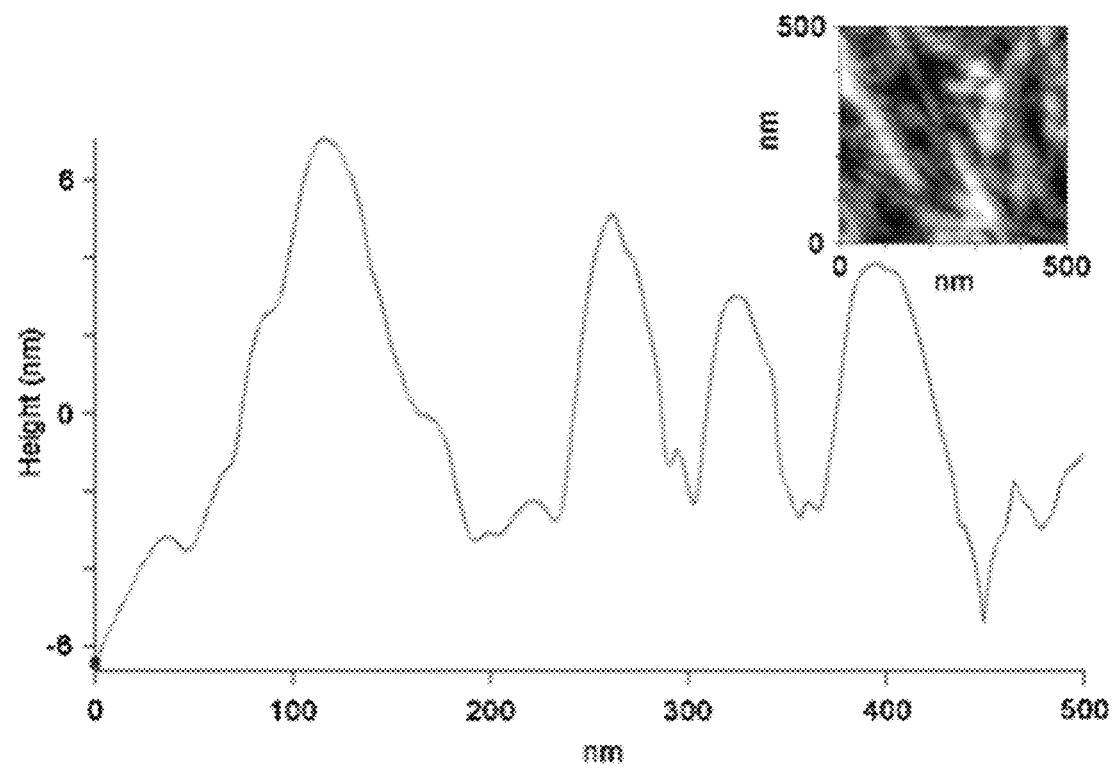
FIG. 7. Topology of GV8 hydrogel. Surface roughness plot across height profiles of dried GV8 hydrogel samples measured via AFM revealed fibers of about 5 nm to 10 nm height.

We then examined the morphology and topology of GV8 hydrogel by Cryo-Electron Microscopy (Cryo-EM), Atomic Force Microscopy (AFM), and Scanning Electron Microscopy (SEM). 20 mM GV8 peptide solution was incubated for 3 h prior to blotting and vitrification to preserve the natural nanostructure of the sample in hydrated conditions (C. J. Newcomb et al. *Curr. Opin. Colloid. In.* 2012, 17, 350)

for Cryo-EM imaging. Long fibers less than 10 nm wide were observed (FIG. 6A) with consistent twisted morphologies and average periods of about 80 nm along the fibers. AFM imaging was performed on a thin layer of dried gel, revealing a surface topology of a network of fibers (FIG. 6B), and the height profile (FIG. 7) revealed fibers of about 5 nm to 10 nm in height thereby matching the Cryo-EM observations. Since drying and conventional lyophilization causes the hydrogel structure to collapse, samples for SEM were prepared by snap-freezing GV8 hydrogel in liquid $N_2$ for at least 5 minutes followed by cryo-fracture and immediate lyophilization to obtain representative cross-sections. SEM imaging revealed a porous structure (FIG. 6C, left) constructed by sheet-like structures and closer examination indicated that the sheets were formed by a fibrous network of peptides (FIG. 6C, right).

Figure 4I:
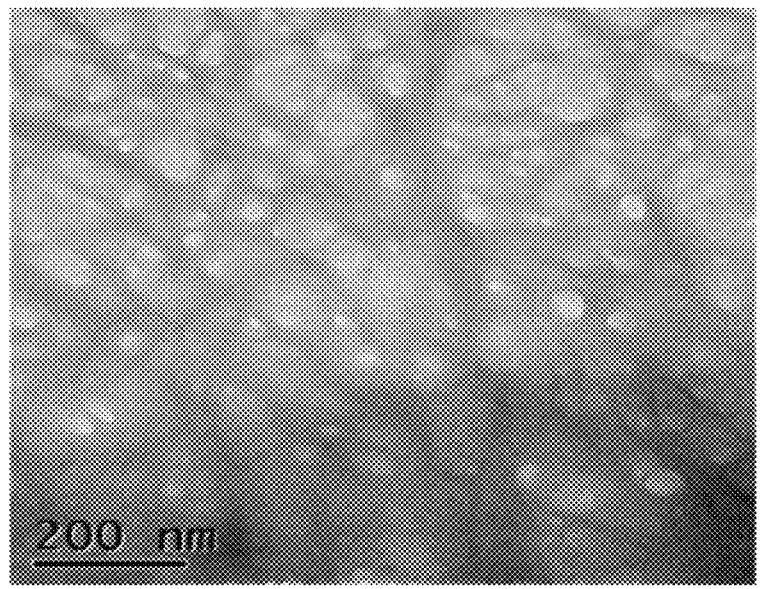
Figure 4J:
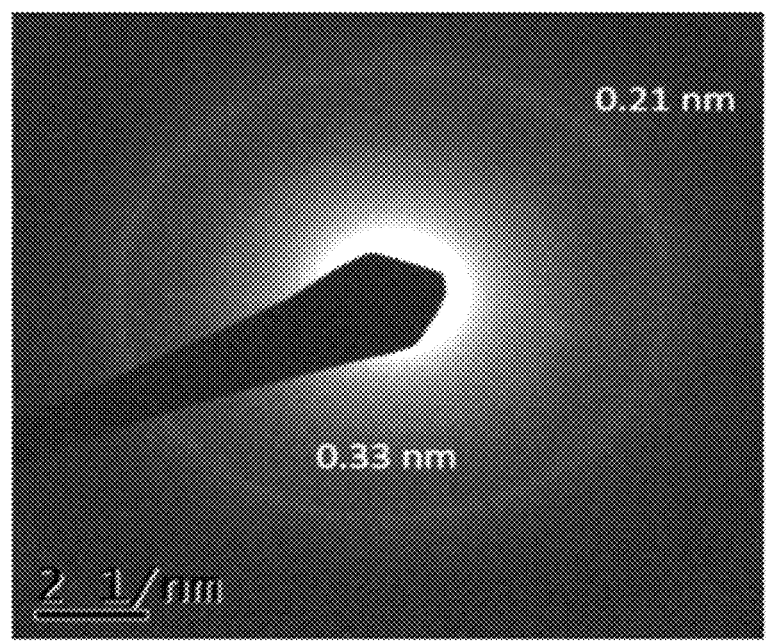

We then examined the morphology and topology of GI8 hydrogels by HR-TEM and SAED. HR-TEM examination of the GI8 peptide fibrils were observed to self-assembled after 40 minutes of incubation in water (FIG. 4I), and as revealed by SAED, the patterns of the GI8 fibrils indicate higher order assemblies with 0.33 nm periodicity observed (FIG. 4J). This may plausibly be attributed to interplanar spacing of the G-G side chain.

1.3 Rheology Characterization

Figure 6D:
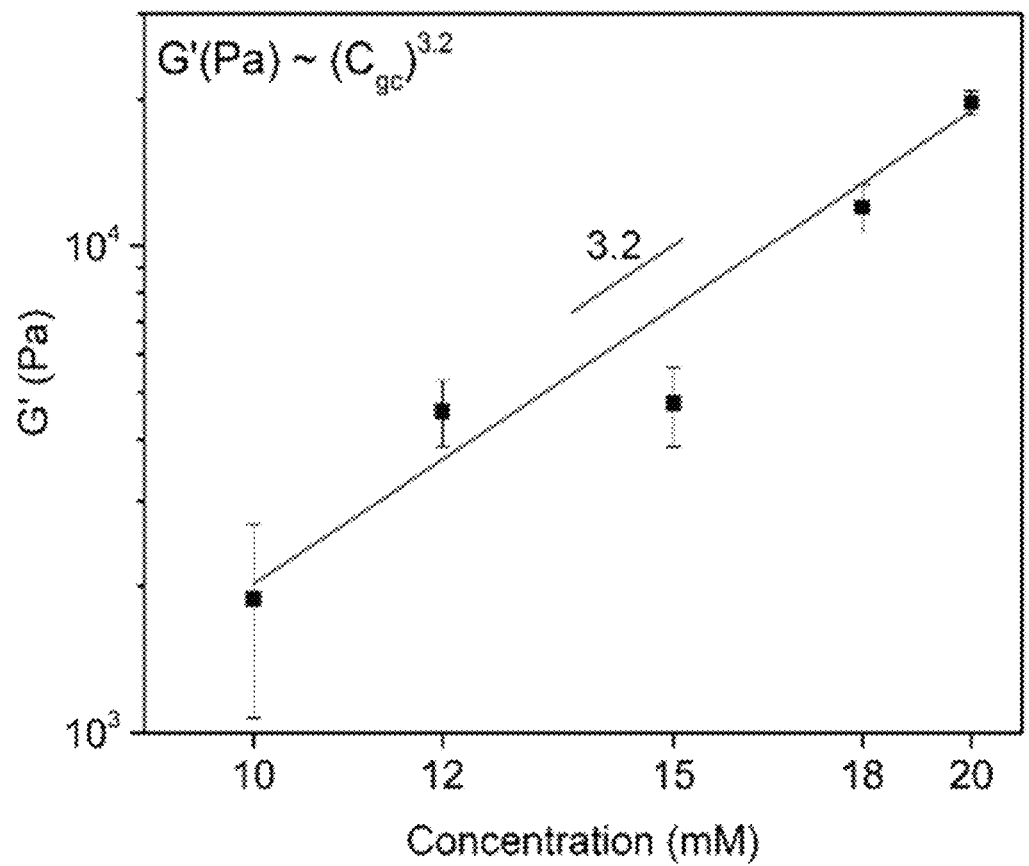
Figure 8A:
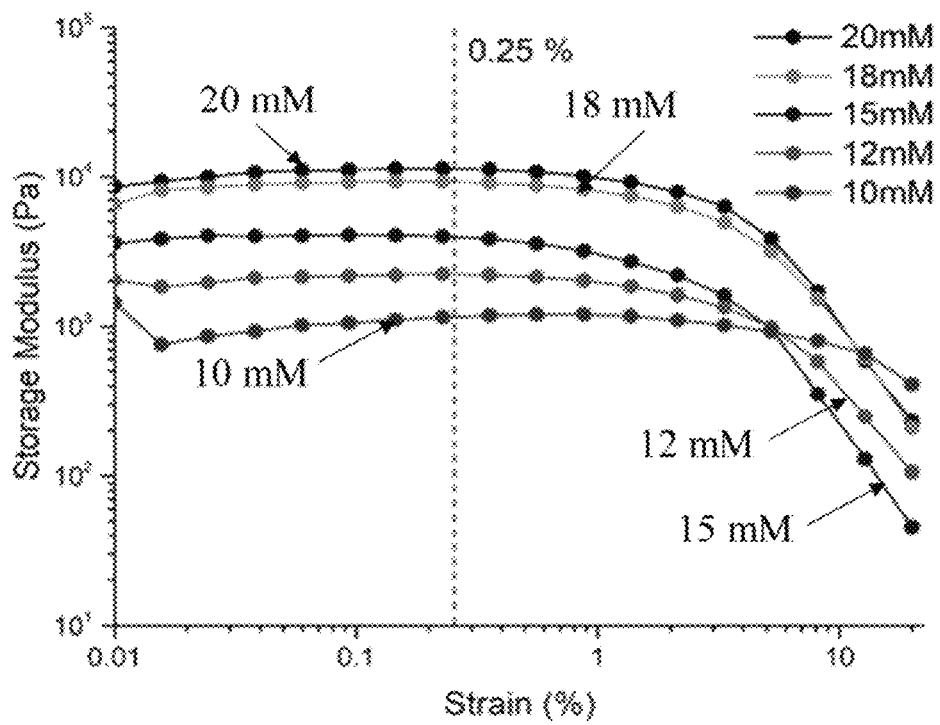
FIG. 8A-8C. Rheological measurements of GV8 hydrogels.
Figure 8B:
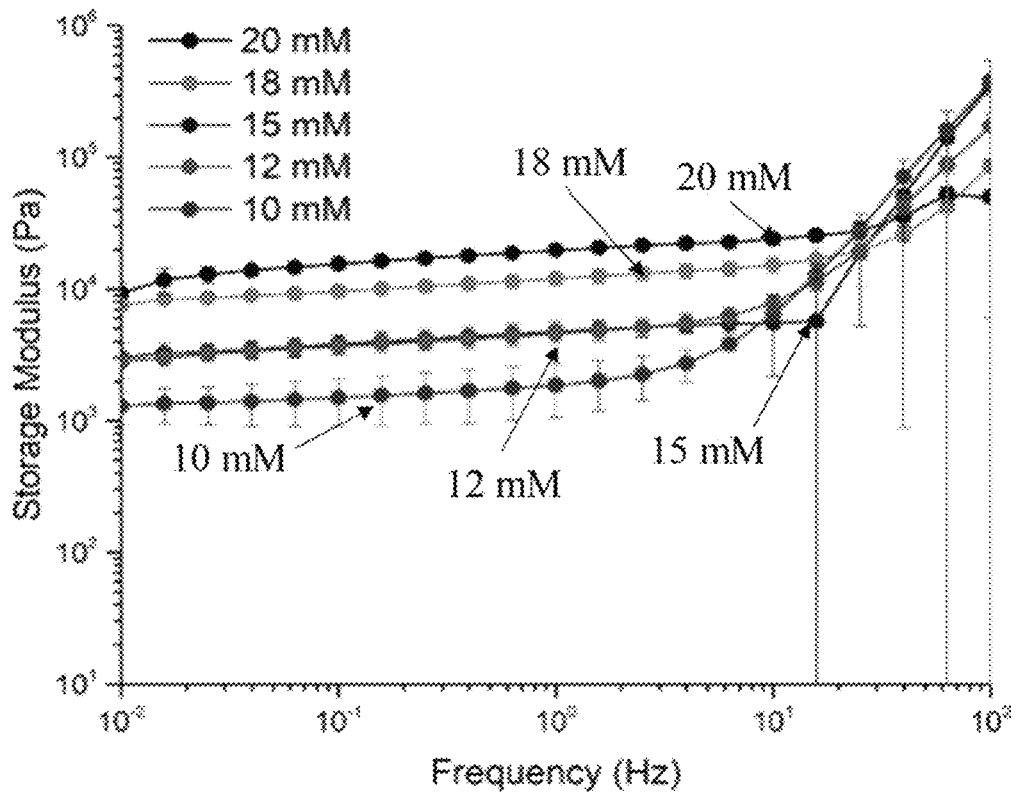
Figure 8C:
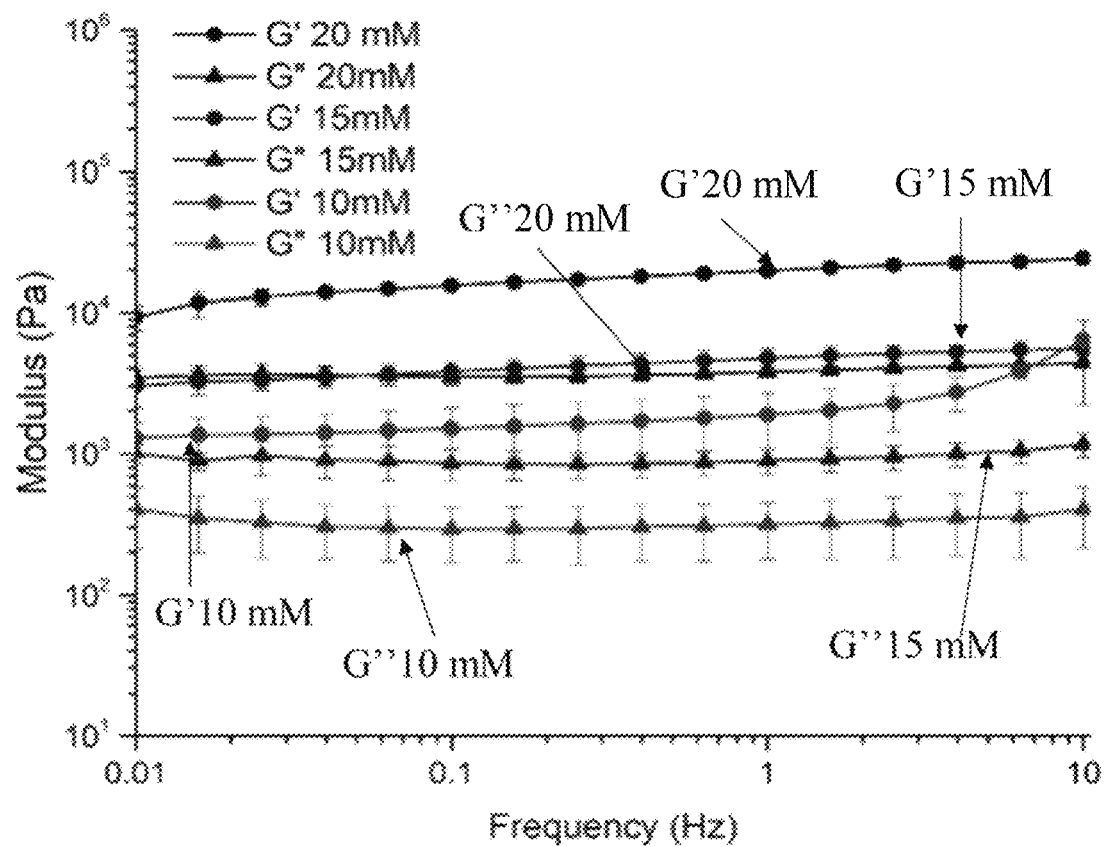
Figure 9A:
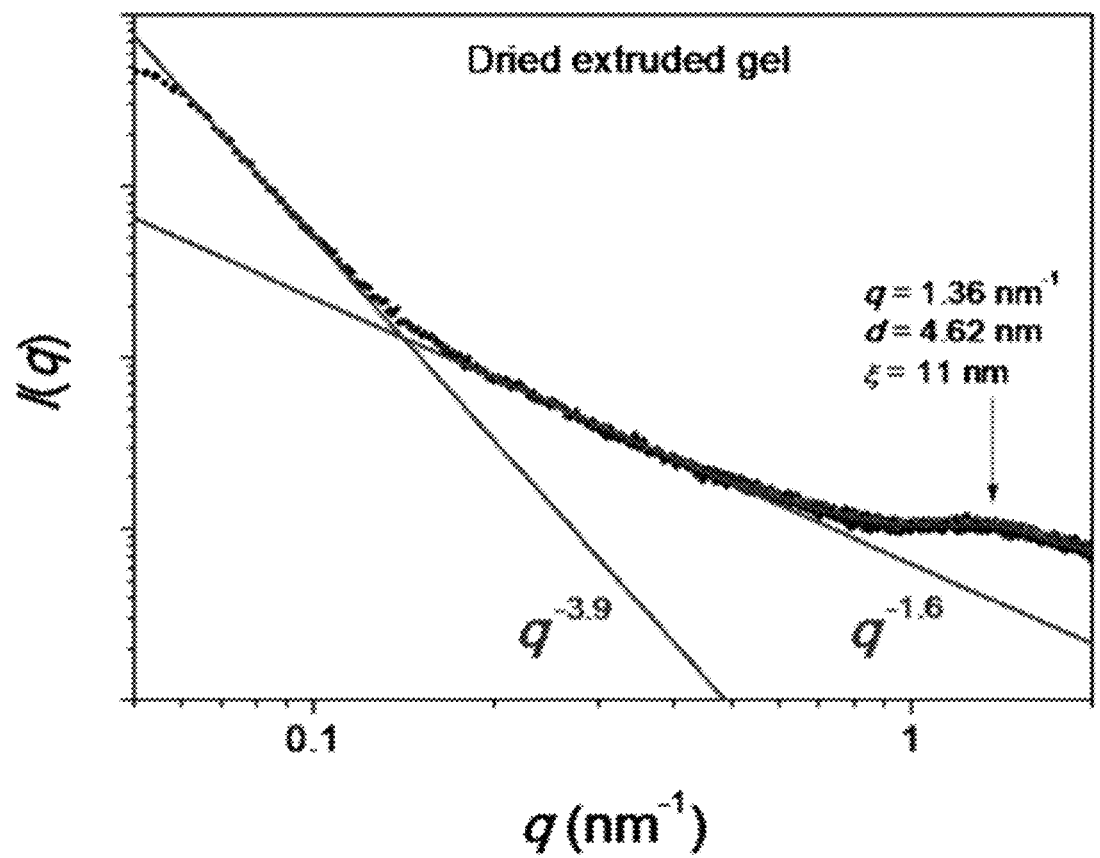
FIG. 9A-9C. SAXS and WAXS patterns for the GV8 peptide extruded gel together with the fitting curve and peaks assignment.

The hydrogel exhibited robust mechanical properties and could readily be manipulated and sectioned into thin slices. In order to characterize the gel's mechanical properties, we prepared GV8 hydrogels with peptide concentrations $C_{gc}$ ranging from 10 mM to 20 mM and conducted oscillation frequency sweeps at 0.25% shear strain (FIG. 8). The shear storage modulus (G') exhibited a scaling power law as a function of peptide concentration (G' vs. $C_{gc}$) with a power law index of 3.2 (FIG. 6D), allowing us to tune the storage modulus (G') of about 25-fold over a narrow range of peptide concentration. We note that this power law index is significantly higher than the "universal" scaling law determined for protein-based semi-flexible networks (F. C. Mackintosh et al. *Phys. Rev. Lett.* 1995, 75, 4425; C. Storm et al. *Nat.* 2005, 435, 191; Y. P. Cao et al. *Phys. Rev. Lett.* 2018, 120, 158103) where G' scales as $C^{11/5}$ or for crosslinked gels that exhibit a G'$\propto C^{2.5}$ scaling law (M. L. Gardel et al. *Science* 2004, 304, 1301). Instead, this behavior is well captured by the fractal gel model, $G' \propto C_{gc}^{((3+d_b)/(3-d_f))}$, where $d_b$ is the fractal dimension of the connecting chain and $d_f$ is the dimensionality of the repeating fractal cluster. Taking $d_f=1.6$ for the fractal dimension as obtained by Small Angle X-ray Scattering (SAXS, FIG. 9A) yields $d_b=1.5$, which is a typical value of heat set protein gels (R. Mezzenga et al. *Rep. Prog. Phys.* 2013, 76, 046601). This behavior suggests that gelation does not proceed by entanglement of long fibrils, but rather by growth of shorter fibrillar clusters and conformational transition as evidenced by NMR and WARS measurements described later. In line with this picture, GV8 did not strain-stiffen, likely because the chain length is shorter than in conventional biological gels. In quantitative terms, the maximum shear modulus of GV8 of 35.5 kPa is on par with the stiffest, non-crosslinked short peptide-based hydrogel containing only natural amino acid residues (Y. H. Loo et al. *Nano Lett.* 2015, 15, 6919). A wide range of moduli have been reported for short peptide hydrogels (C. Q. Yan et al. *Chem. Soc. Rev.* 2010, 39, 3528; M. A. Greenfield et al. *Langmuir* 2010, 26, 3641; B. Ozba et al. *Macromol.* 2004, 37, 7331; A. Bertolani et al. *Nat. Comms.* 2015, 6, 7574) with stiffest gels reached in gels containing modified amino acids, synthetic functional groups, or which have been crosslinked (D. J. Adams et al. *Soft Matter* 2009, 5, 1856; W. Y. Seow et al. *Sci. Rep. UK* 2016, 6, 32670). The ability to tune the stiffness from 1.3 to 35.5 kPa is particularly appealing for stem cell differentiation studies since gel stiffness has been well-documented to govern cell adhesion and regulation based on the substrate's mechanical feedback (B. Trappmann et al. *Nat. Mater.* 2012, 11, 642; D. E. Discher et al. *Sci.* 2005, 310, 1139; A. J. Engler et al. *Cell* 2006, 126, 677; M. Ahearne. *Interface Focus* 2014, 4, 20130038), with stiffness values in the range 0.1 kPa to 1 kPa, 8 kPa to 17 kPa and 25 kPa to 40 kPa sought after for neurogenic, myogenic, and osteogenic differentiation, respectively. The advantage of our GV8 hydrogel for such applications is that its stiffness can be modulated solely by varying the peptide concentration without any additional chemical modifications.

1.4 Circular Dichroism and FTIR Spectroscopy

Figure 6E:
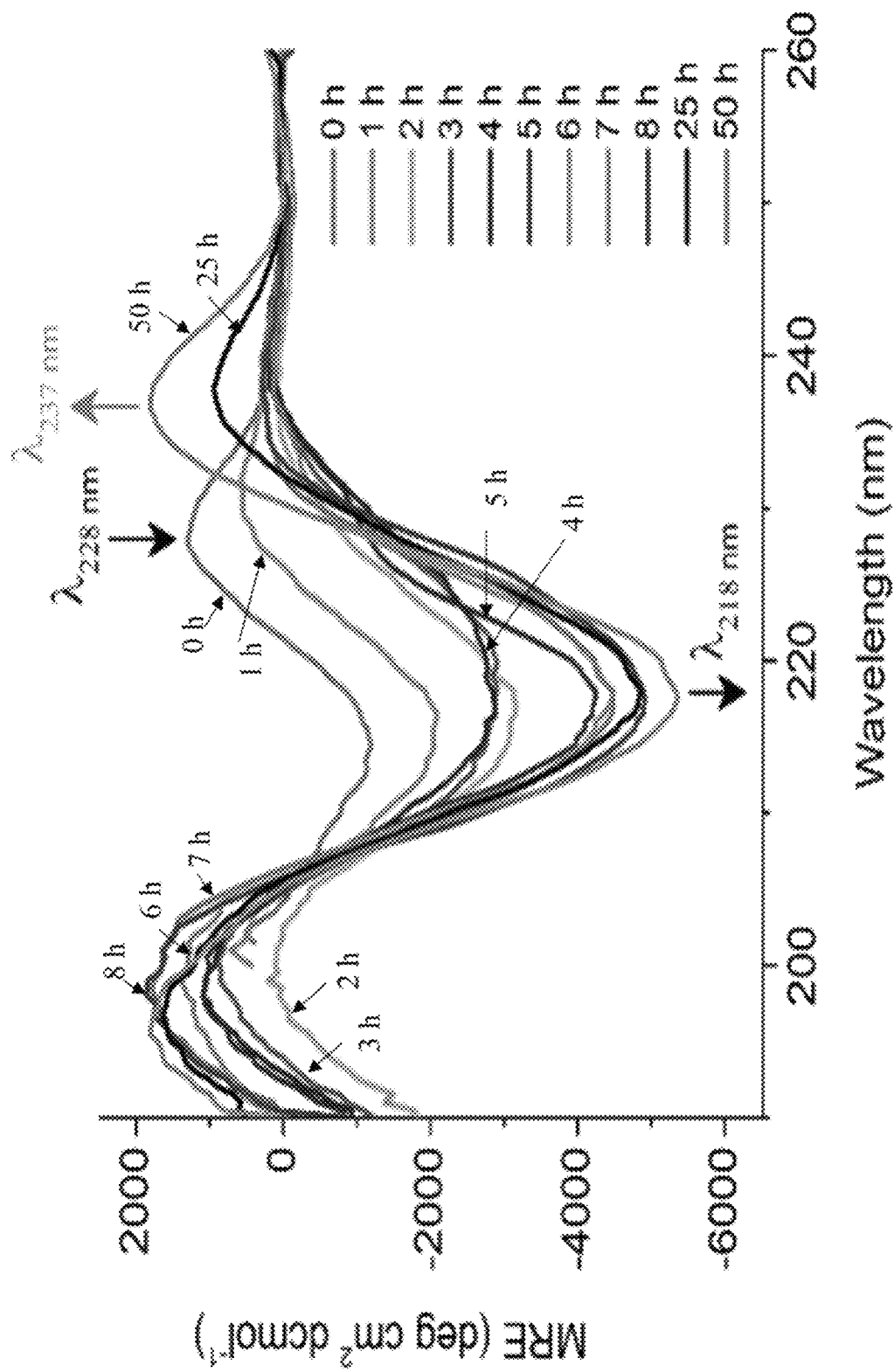
Figure 6F:
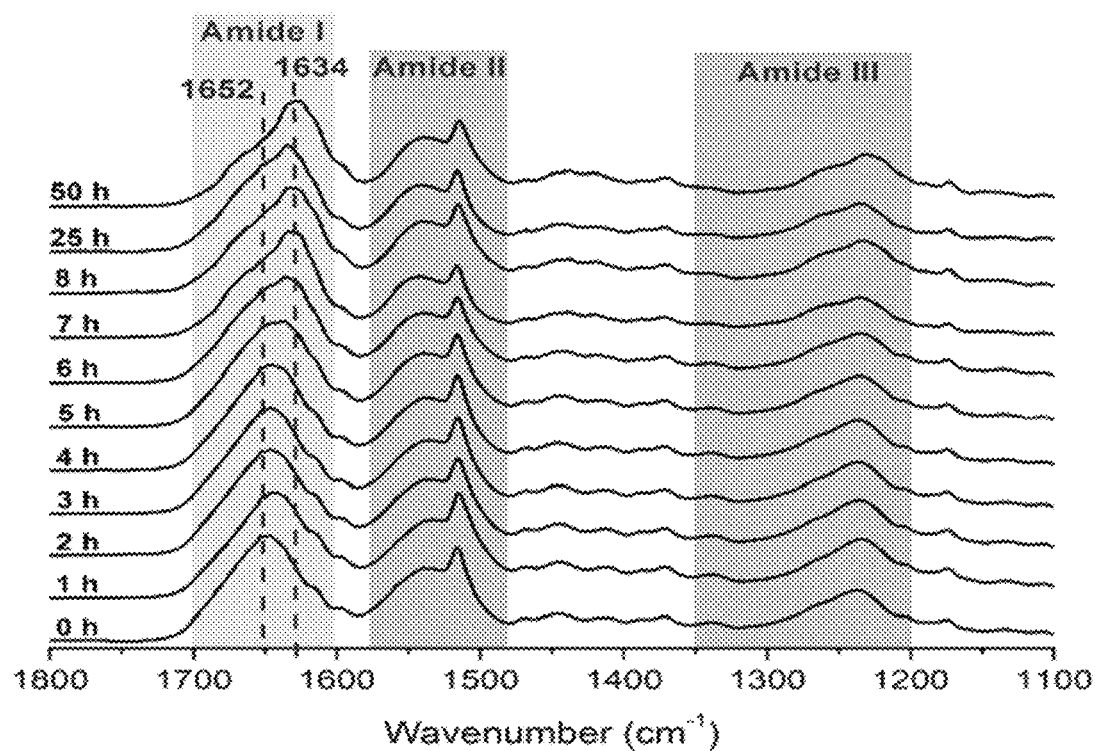

Next, we conducted time-dependent Circular Dichroism (CD) and Attenuated Total Reflection Fourier Transform Infrared Spectroscopy (ATR-FTIR) measurements on 20 mM GV8 from its initial solution state until its post-gelation state in order to reveal secondary structural changes during self-assembly (FIGS. 6E and 6F). At time 0 h, the CD spectrum consisted of a minimum at 215 nm and two maxima at 200 nm and 228 nm (FIG. 6E). The bands at 215 nm and 228 nm are attributed to the resultant exciton couplet of Tyr-Tyr exciton interaction of their $\pi \rightarrow \pi^*$ transitions, also known as CD Cotton effect (I. B. Grishina et al. *Faraday Discuss.* 1994, 99, 245; M. A. Khan et al. *Biochem. US.* 2007, 46, 4565) indicating interaction between the Tyr aromatic chromophores (A. G. Cochran et al. *PNAS. USA.* 2001, 98, 5578; L. Wu et al. *Biochem. US.* 2010, 49, 4705), as also corroborated by our 2D NMR data. Over the course of gelation (1 h to 5 h), the minimum shifted to 218 nm with a significant increase in intensity, and the maximum at 228 nm diminished, thereby transitioning to β-sheet secondary structure. The CD spectra remained constant after 5 h in agreement with our $OD_{550\ nm}$ measurements of 20 mM GV8 peptide (FIG. 4A), whereby the absorbance plateau onset at 5 h indicated that gelation was complete without any significant structural changes after 5 h. Upon further incubation post-gelation (25 h and 50 h), a new maximum appeared at 237 nm and can be assigned to aromatic transitions of the Tyr residues (R. W. Woody. *Biopoly.* 1978, 17, 1451), which we postulate is related to the conformational transition of GV8 peptide during gelation.

Figure 4K:
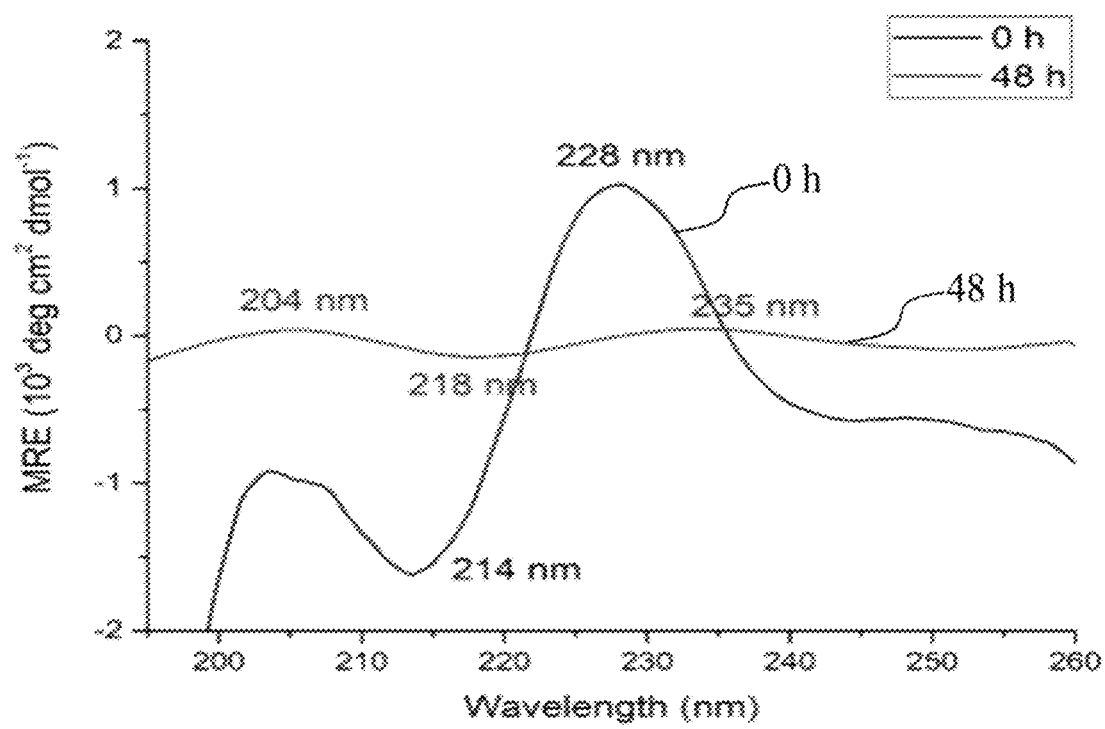

For the GI8 peptide, the CD spectra obtained on 10 mM GI8 peptide in water at 0 h and 48 h indicated a strong Y-Y cotton effect (228 nm) and 214 nm minima similar to that of GV8 peptide. This is plausibly due to the turns and $3_{10}$ helix conformation that was observed at 0 h. The post-gelation spectra for GI8 obtained in solution at 48 h show a β-sheet signature with low intensity as most peptides are involved in hydrogel formation, i.e. out of the solution (FIG. 4K).

Figure 10A:
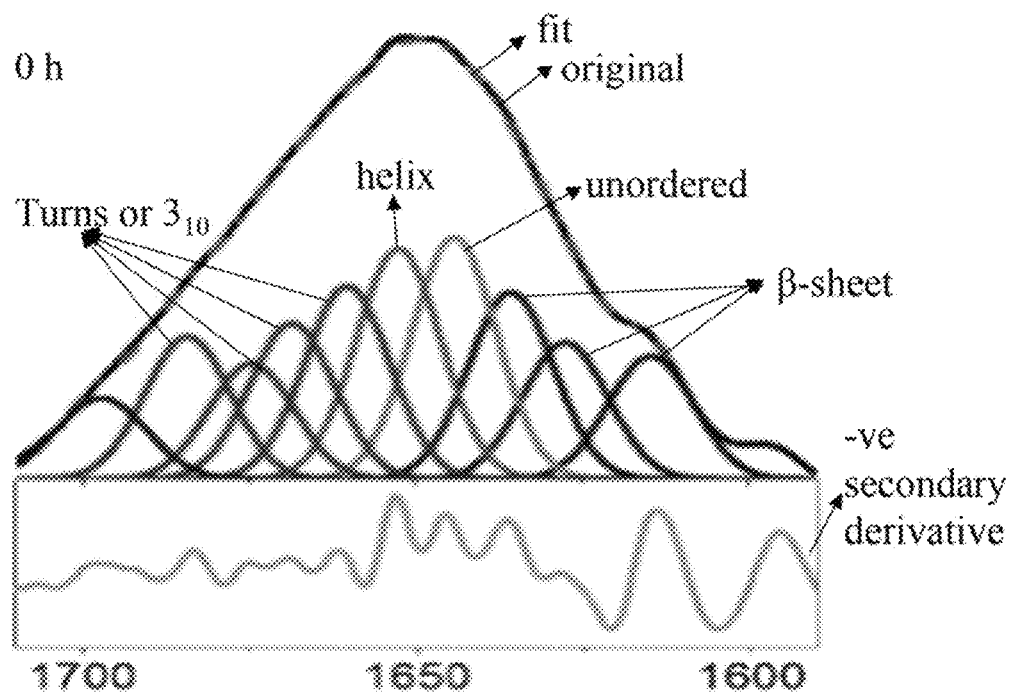
FIG. 10A-10K. Deconvolution of ATR-FTIR spectra of GV8 self-assembly over a time period of 50 h. Secondary derivates were obtained to deconvolute the amide I bands of each spectra. FWHM of each fitted peak were kept consistent and position of peaks were assigned accordingly.
Figure 10B:
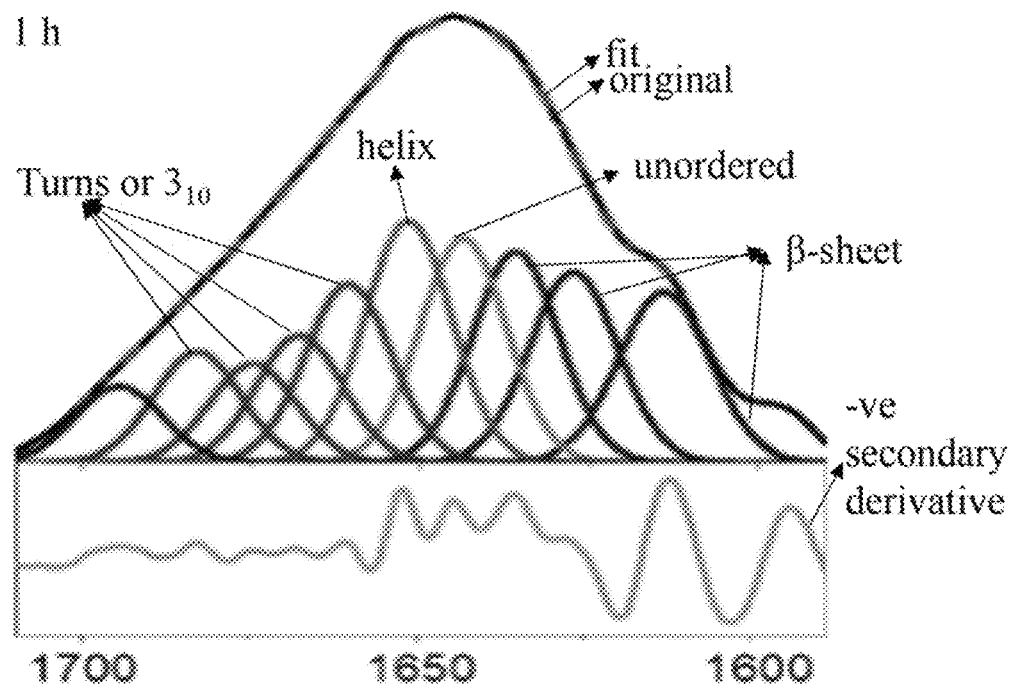
Figure 10C:
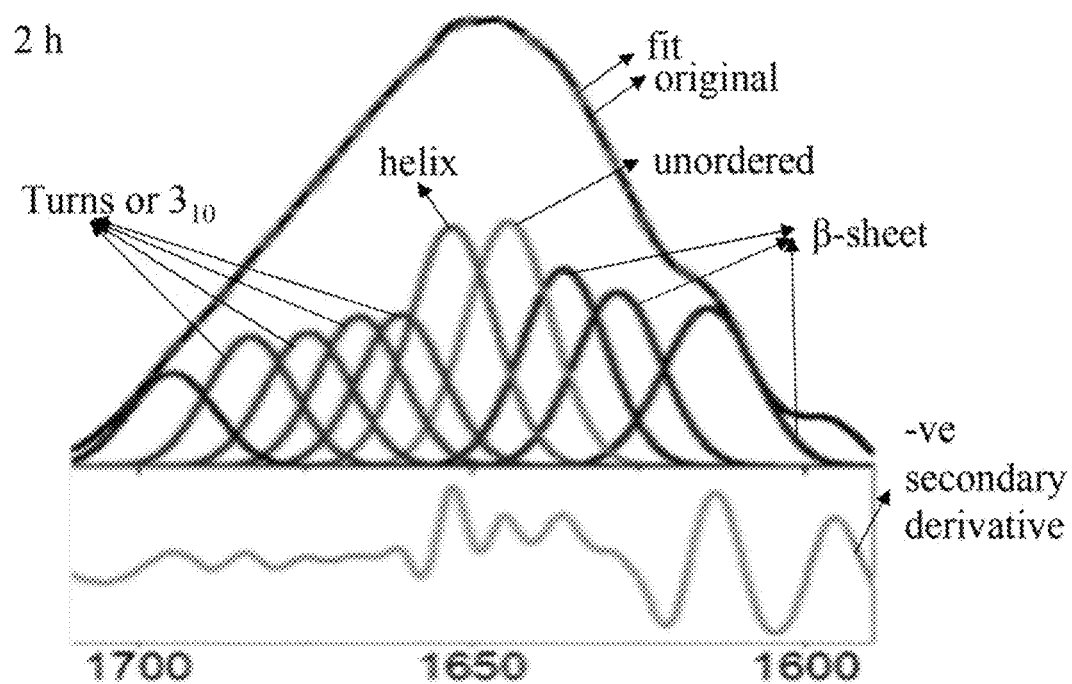
Figure 10D:
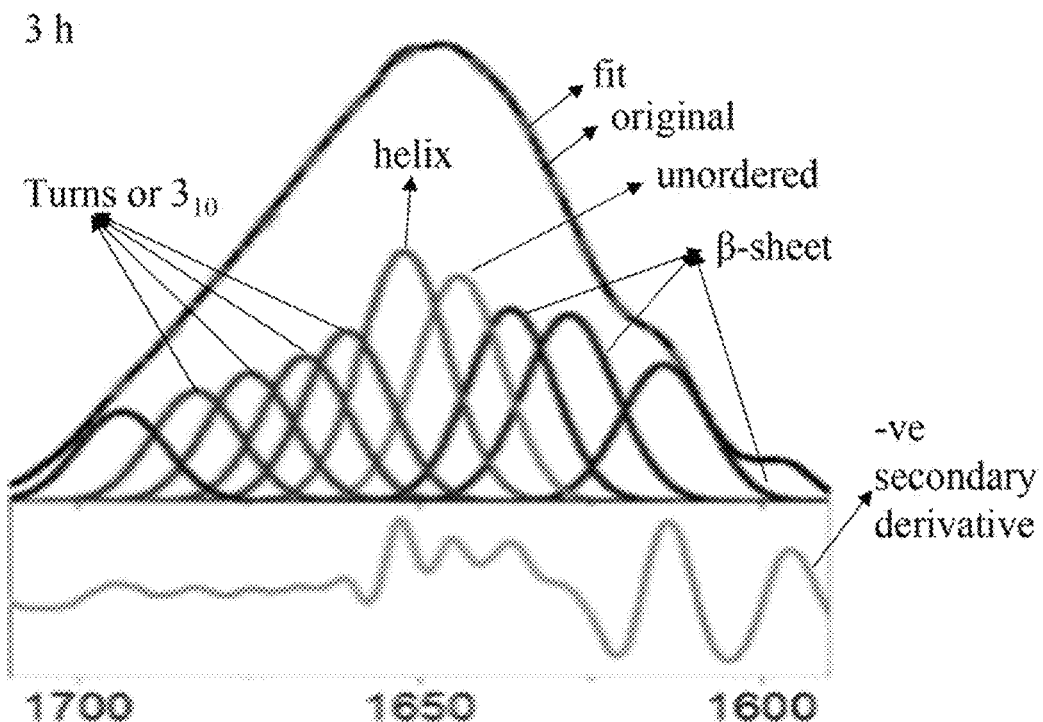
Figure 10E:
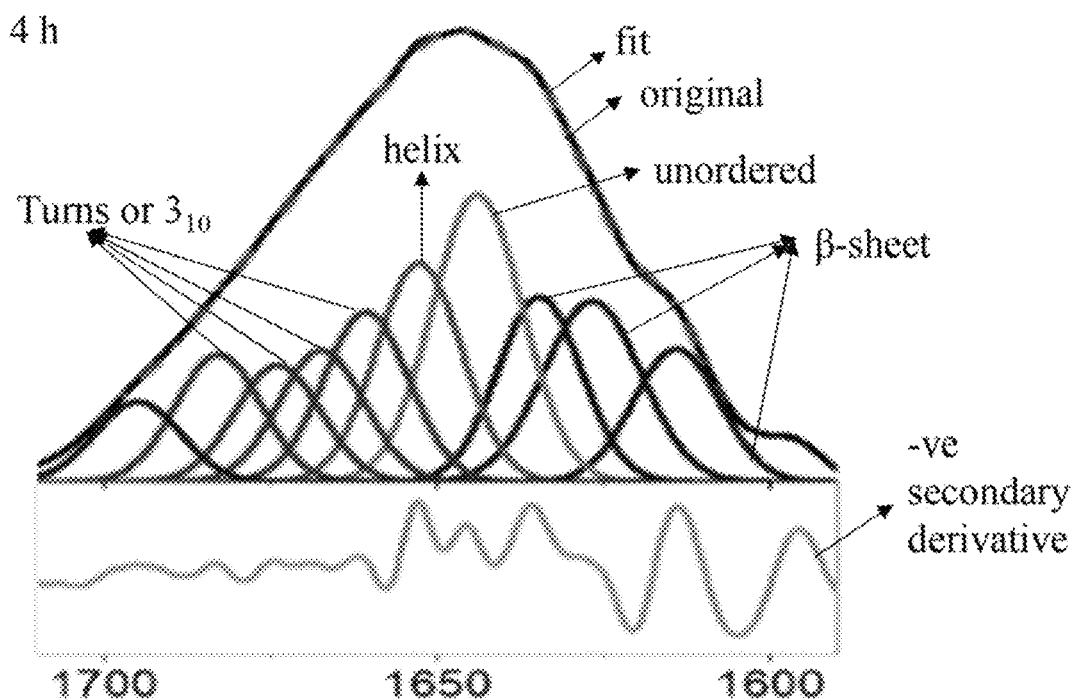
Figure 10F:
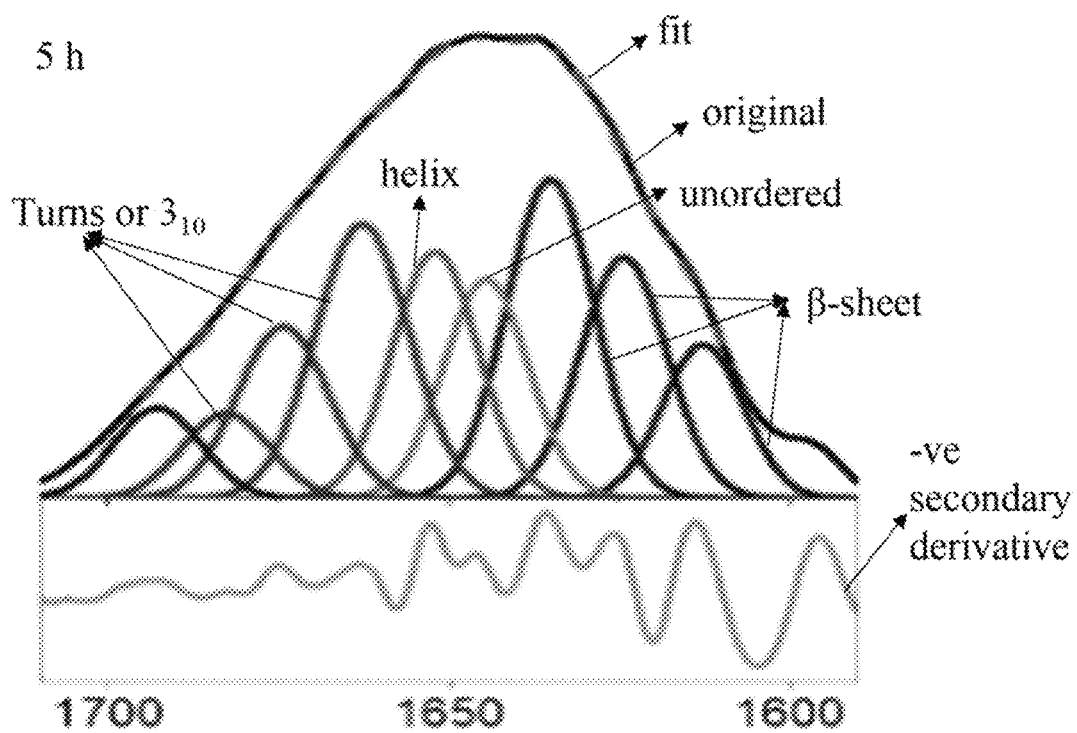
Figure 10G:
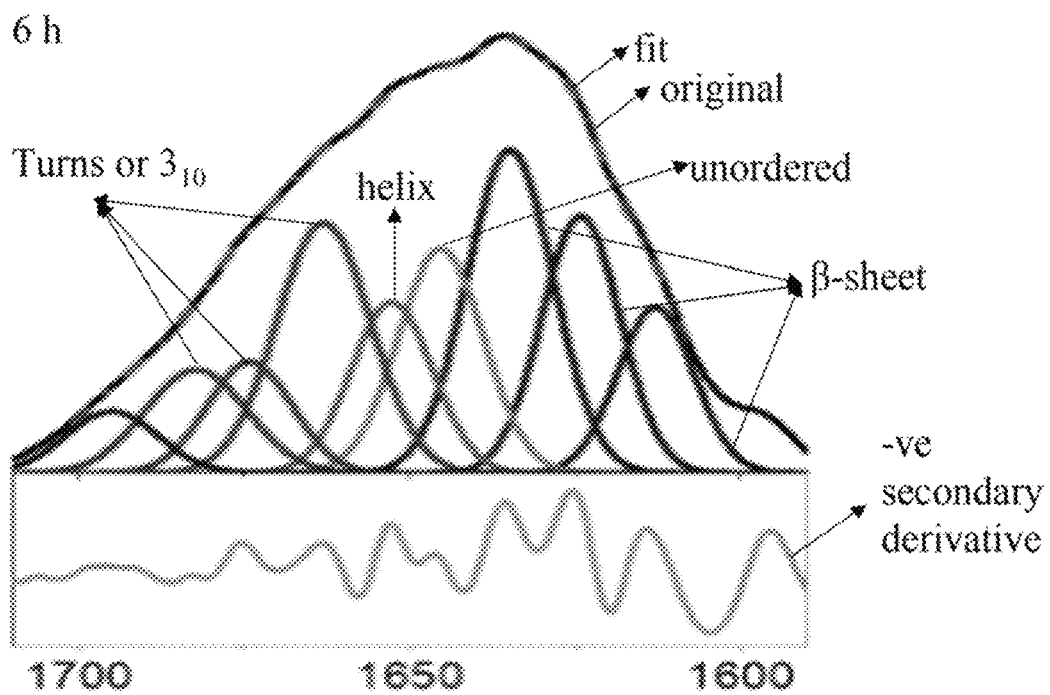
Figure 10H:
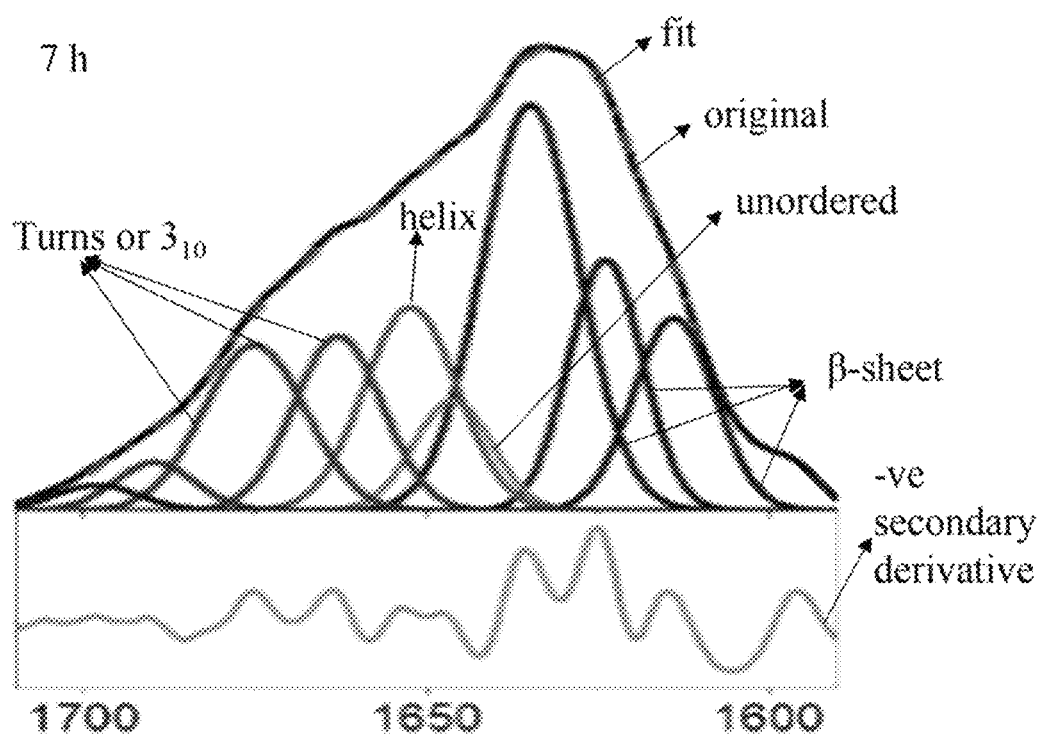
Figure 10I:
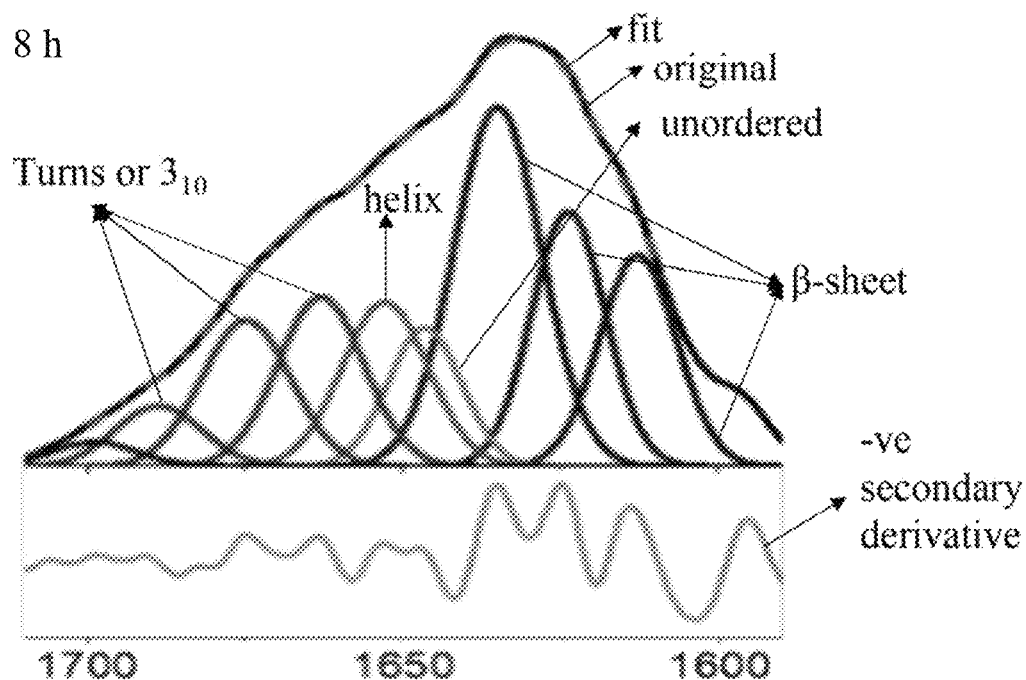
Figure 10J:
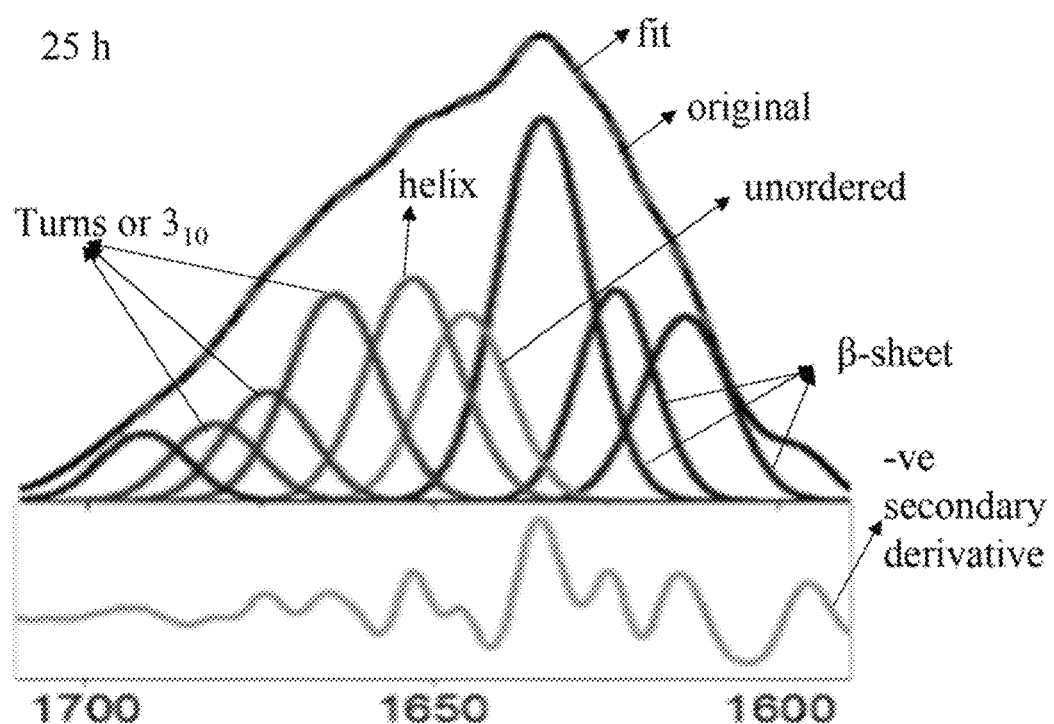
Figures 10K, 11:
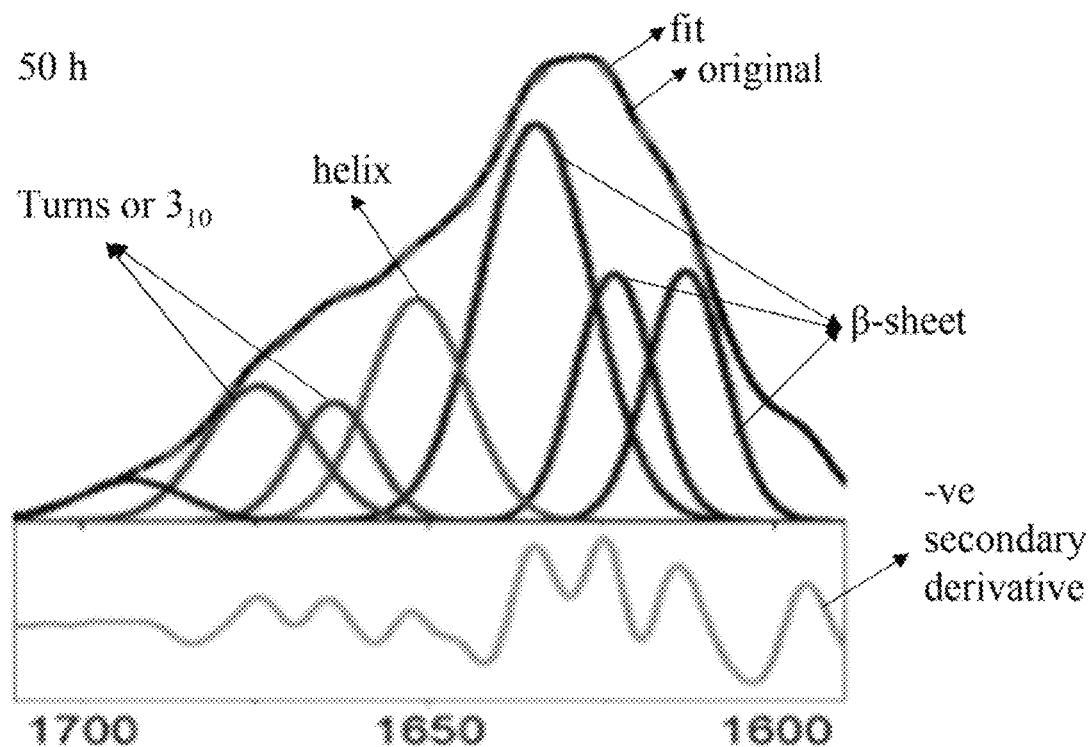
FIG. 11. Heat-map summary of secondary structure assignments and their percentage of secondary structural composition from the deconvolution of Amide I peaks of GV8 peptide over 50 h of incubation.

ATR-FTIR was performed on dried 20 mM GV8 hydrogels incubated over the same time points as in CD studies. The samples were snap-freezed in liquid $N_2$ to arrest the structural assembly of the peptides at stipulated time points. Amide I bands were deconvoluted and peaks assigned to β-sheets, unordered regions, helices and turns, or $3_{10}$ helices (FIG. 10; J. Kong et al. *Acta Bioch. Bioph. Sin.* 2007, 39, 549; H. Y. Yang et al. *Nat. Protoc.* 2015, 10, 382). β-turns and $3_{10}$ helices were grouped together in our assignments as they are structurally alike (R. Armen et al. *Prot. Sci.* 2003, 12, 1145; A. G. de Brevern. *Sci. Rep.* 2016, 6, 33191) with similar hydrogen bond strengths, and hence close frequency positions within the Amide I band. Over the course of gelation, the Amide I band maximum at $\tilde{v}_{max}$=1652 cm$^{-1}$ shifted to 1634 cm$^{-1}$ (FIG. 6F), confirming secondary structural change towards β-structures. Semi-quantitative analysis by deconvolution of Amide I band (FIG. 11) indicated that the initial dominating secondary structures of GV8 peptide were turns and/or $3_{10}$, whereas in the gel state β-sheet structures were the most abundant (of about 65% at 50 h).

Figure 4L:
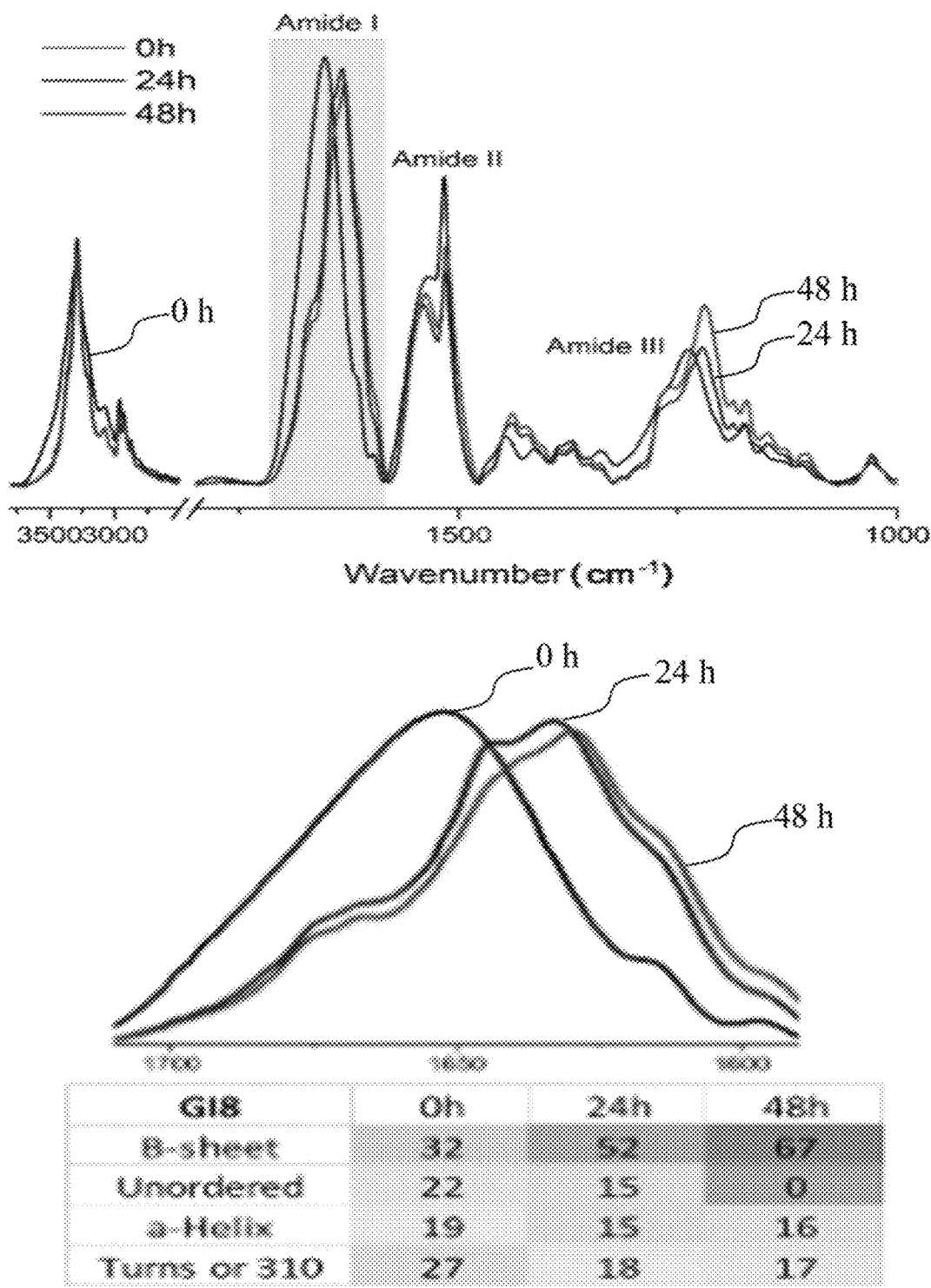

For the GI8 peptide, ATR-FTIR spectra obtained on 10 mM GI8 peptide in water at 0, 24 and 48 h show a significant shift of Amide I band from mixed secondary structures to a β-sheet dominated composition (FIG. 4L). The inset as shown in FIG. 4L shows magnified Amide I band and a deconvoluted secondary structure composition of GI8 at different time points.

1.5 Solution NMR

Figure 12A:
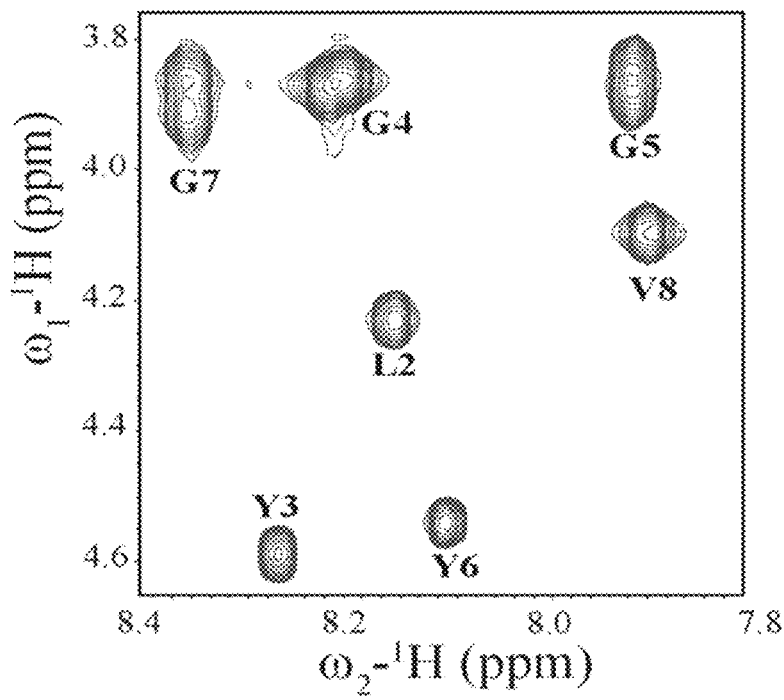
FIG. 12A-12E. Solution NMR characterization of GV8 at monomeric concentration (0.5 mM).
Figure 12B:
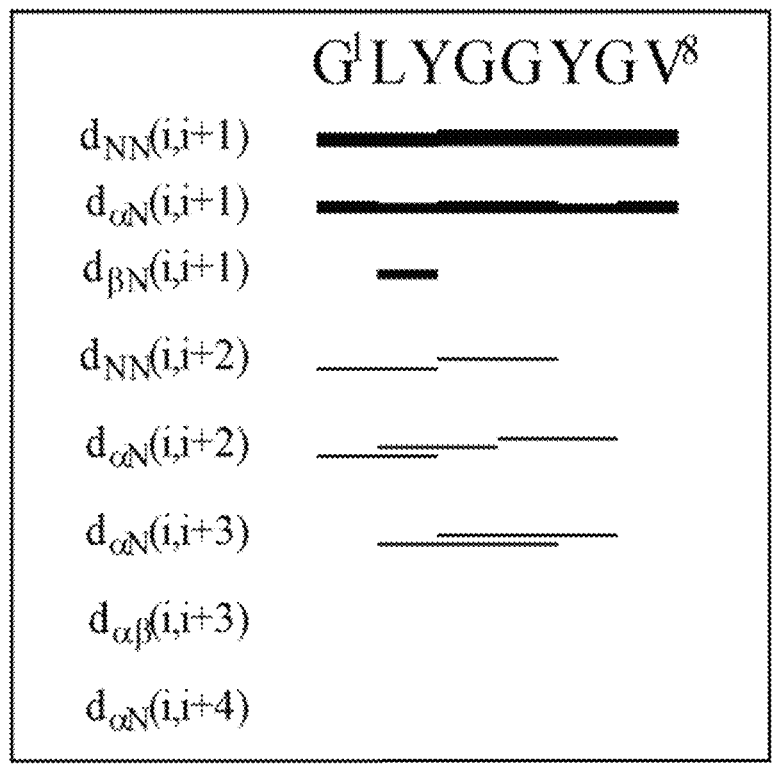
Figure 12C:
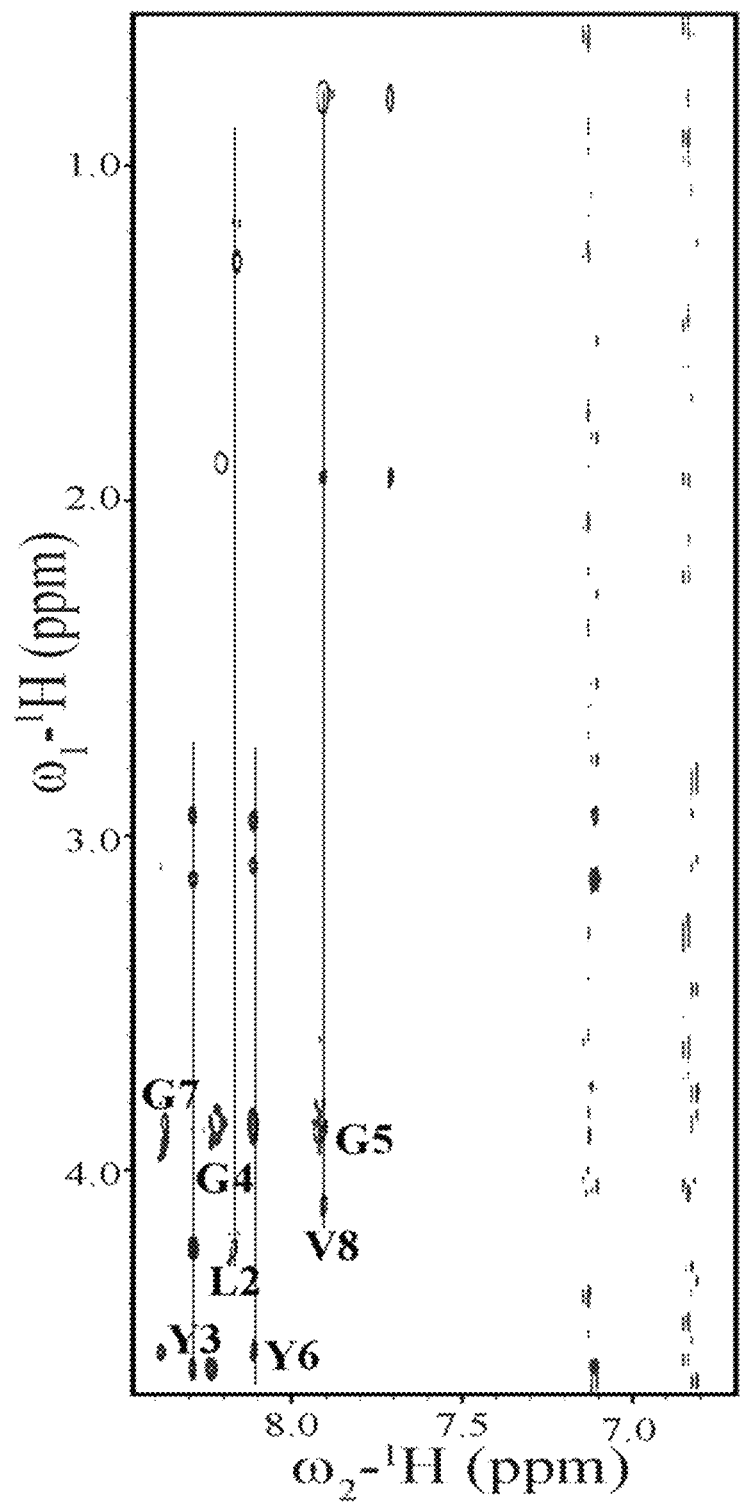
Figure 12D:
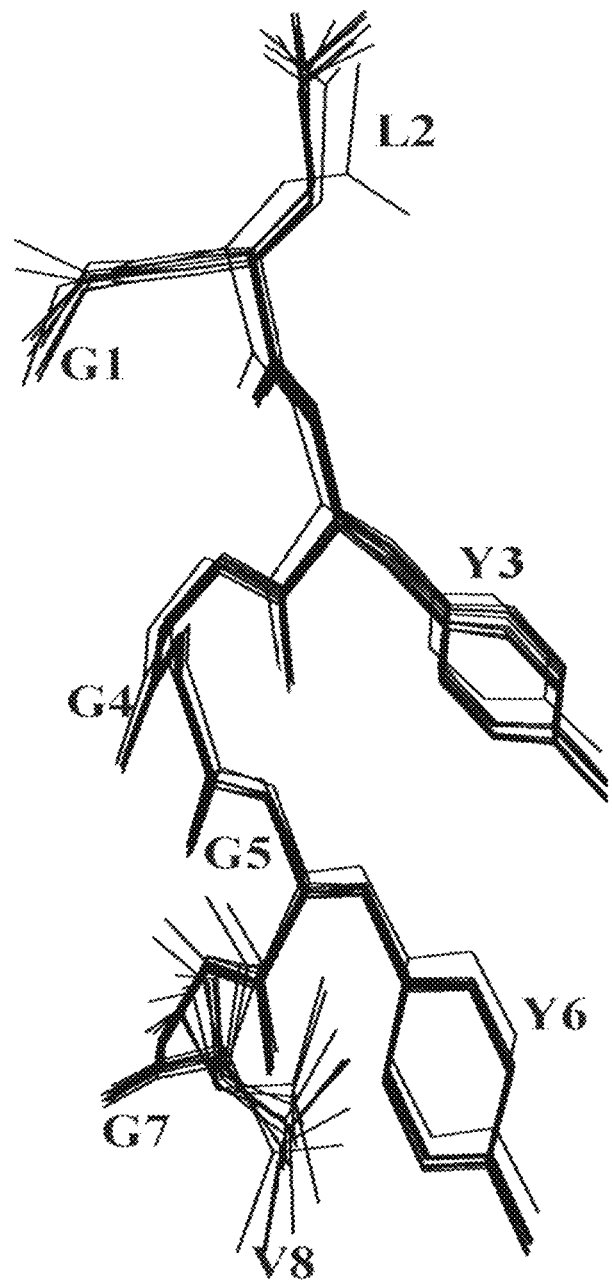
Figure 12E:
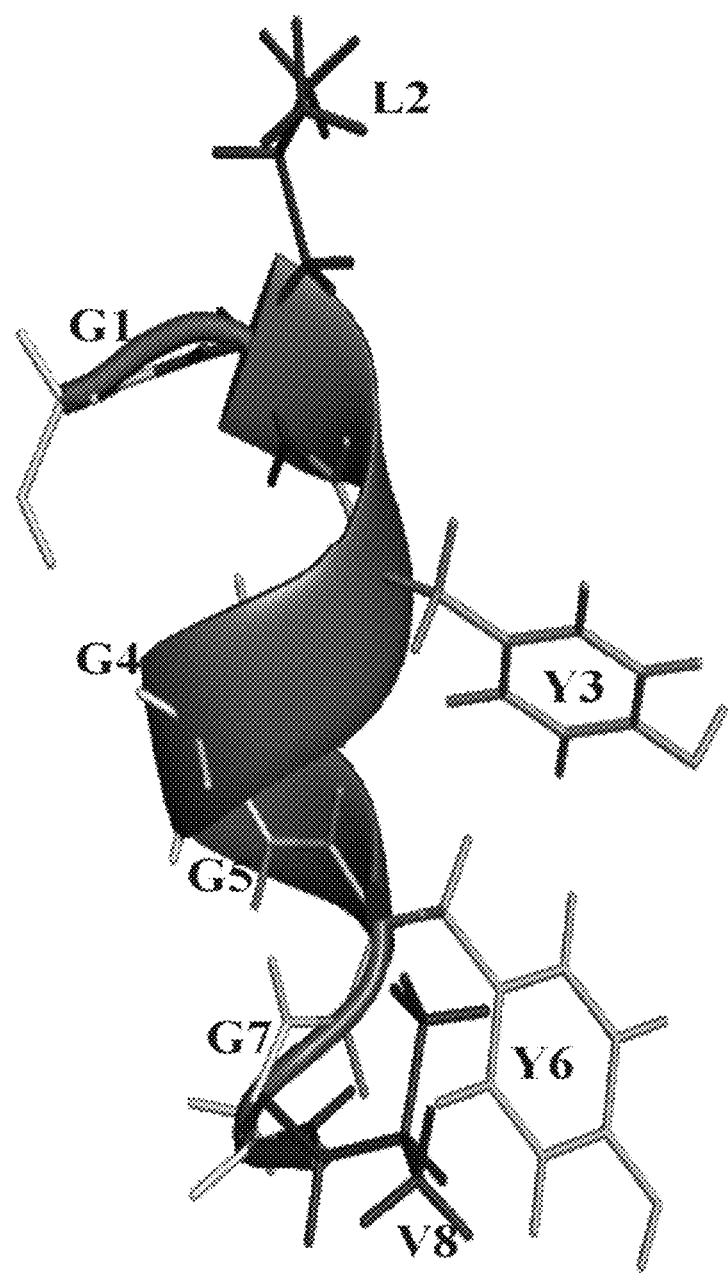
Figure 13A:
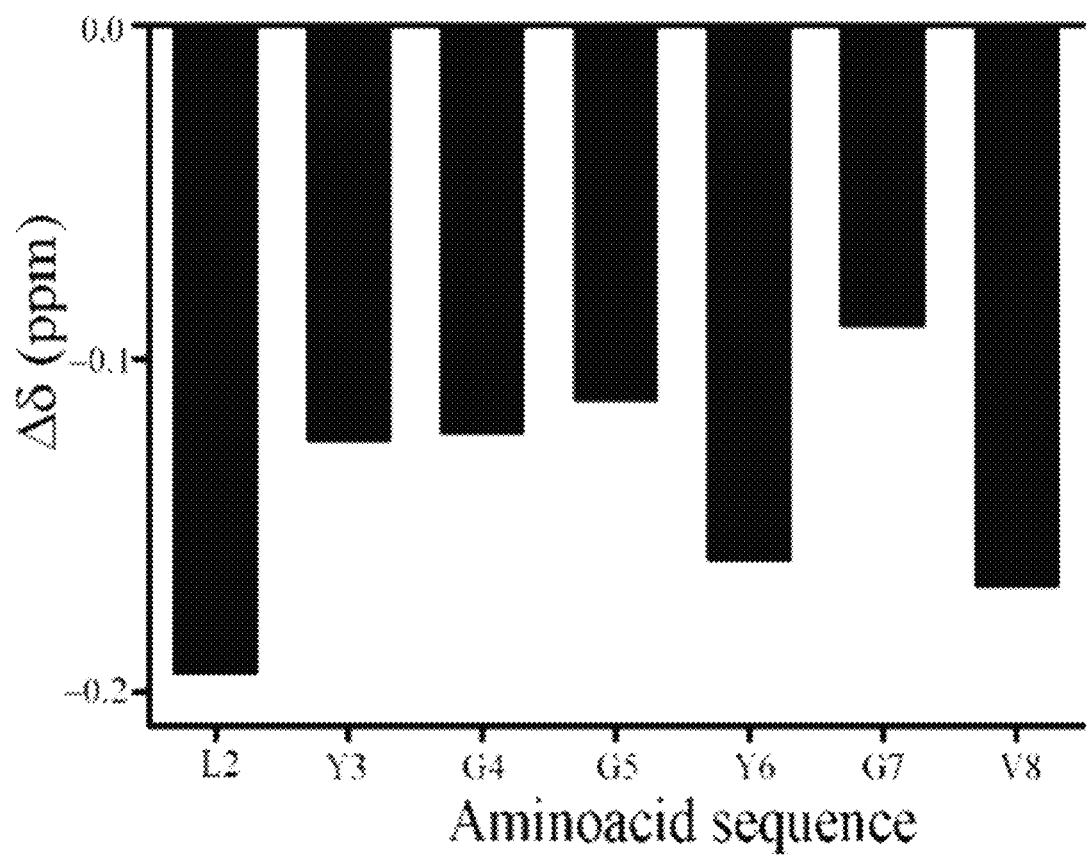
FIG. 13A-13D. Chemical shift deviations (CSD) and gelation of GV8 and 2D $^{1}$H-$^{1}$H NOESY spectra of terminal mutated analogs of GV8.
Figure 13B:
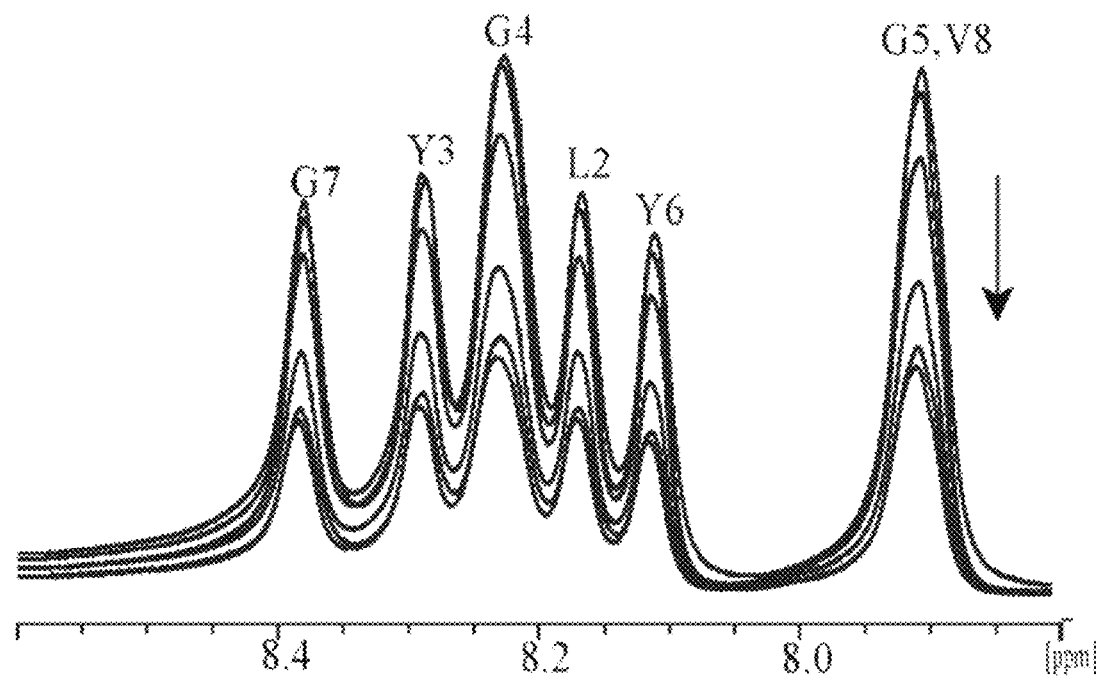
Figure 13C:
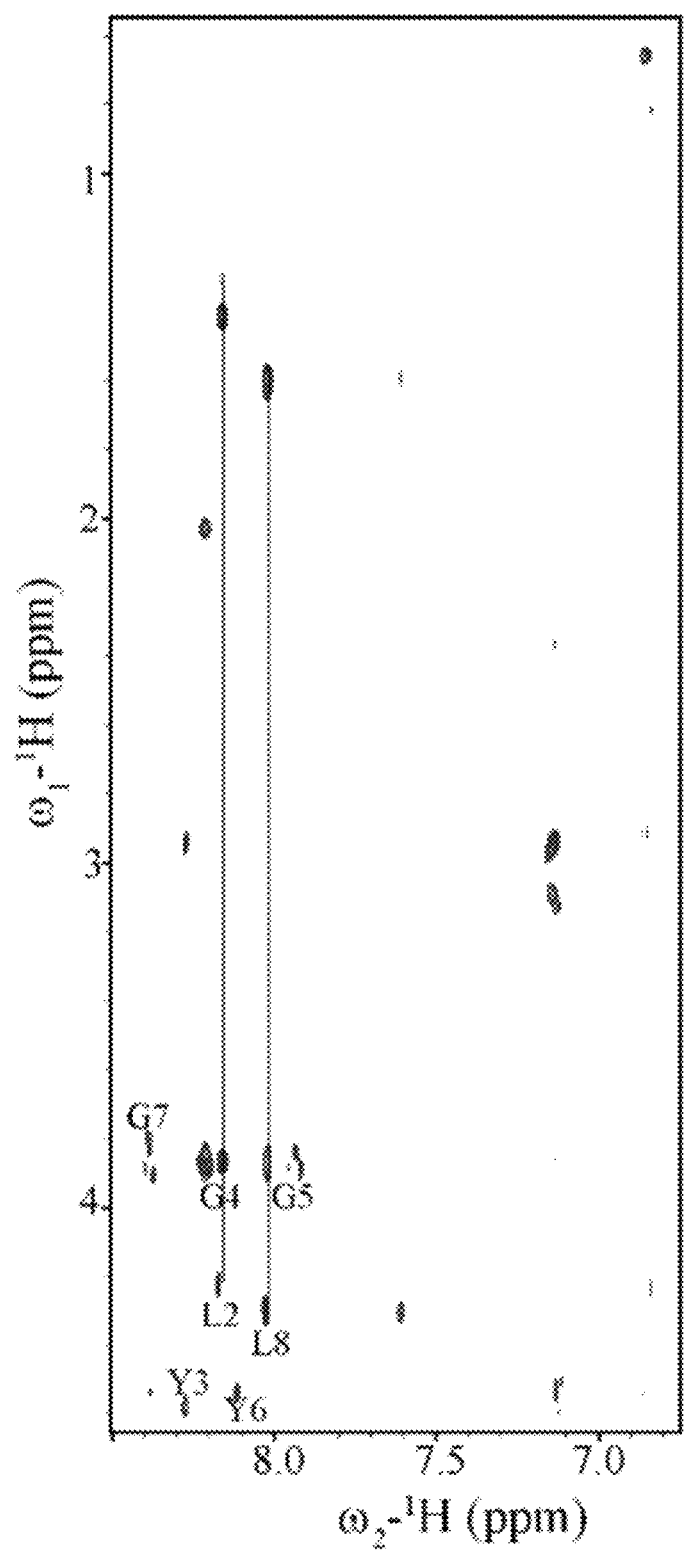
Figure 13D:
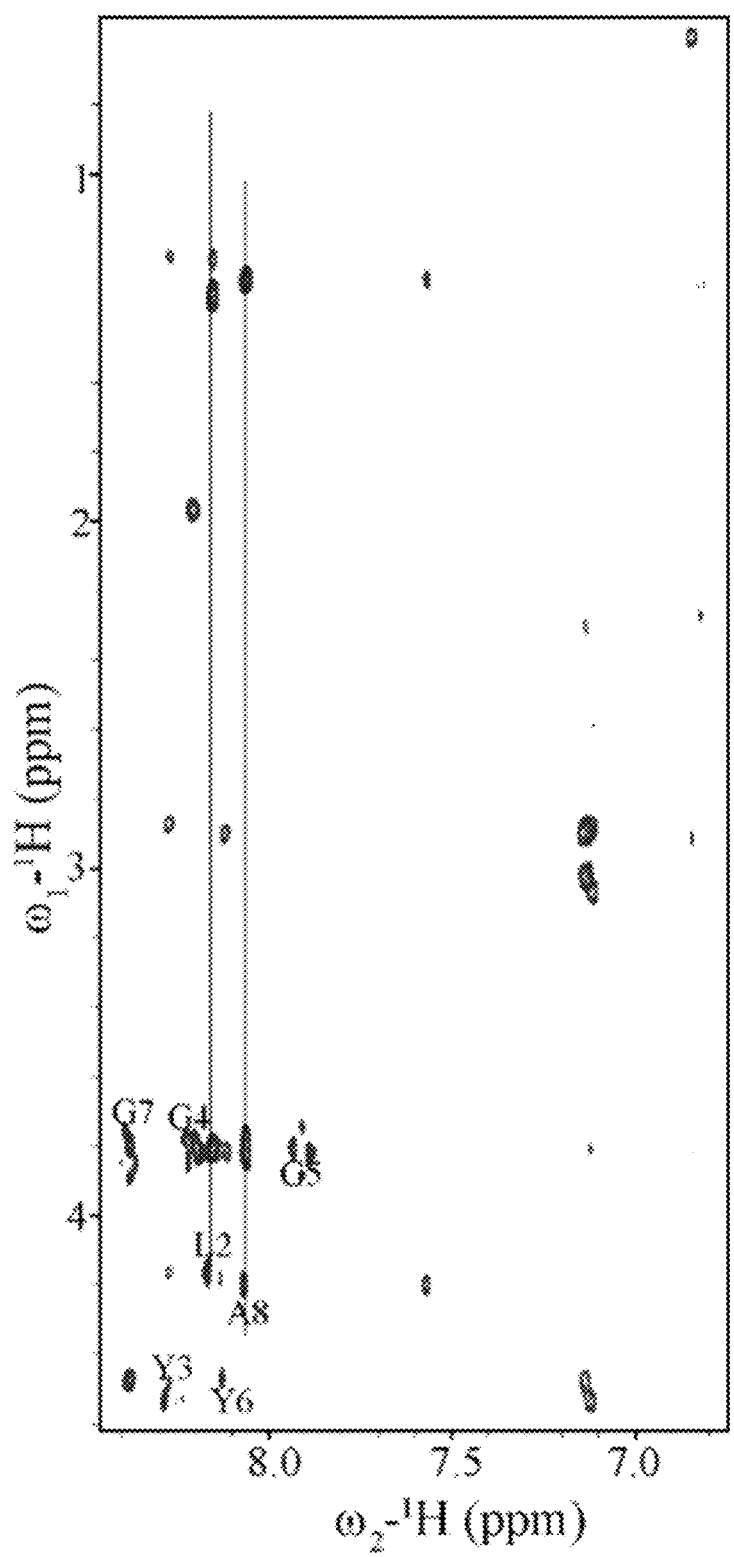

In order to obtain the molecular level structure of GV8, we analyzed the 3D structure of the peptide in solution using NMR. To maintain the peptide in soluble form, its concentration was kept at 0.5 mM. 2D $^1$H-$^1$H TOCSY (TOtal Correlation SpectroscopY) and $^1$H-$^1$H NOESY (Nuclear Overhauser Effect SpectroscopY) spectra showed well-resolved cross-peaks assigned to the individual amino acid residues of GV8 (FIGS. 12A and 12C). The $^1$H$^\alpha$ CSD (D. S. Wishart et al. *Biochem.* 1992, 31, 1647) exhibited negative chemical shifts suggestive of a predominantly helical structure (FIG. 13). However, precise examination of the $^1$H-$^1$H NOESY spectrum revealed the absence of (i, i+4) medium range (H$^\alpha$-H$^N$) NOE connectivities typically observed in α-helix (FIG. 12B). Instead, we only detected (i, i+3) H$^\alpha$-H$^N$ NOEs in addition to the strong (i, i+1) H$^N$-H$^N$ NOEs, suggesting the presence of $3_{10}$ helix (G. L. Millhauser et al. *J. Mol. Biol.* 1997, 267, 963). Further analysis also revealed the presence of ring proton NOEs between Y3 and Y6 stabilizing the $3_{10}$ helical structure (FIG. 12C). Collectively, these data indicated that the aromatic side chain interactions between Y3 and Y6 may lead the GV8 peptide to adopt a well-defined $3_{10}$ helix. This was also supported by NOEs between aliphatic side chains of L2 and V8 along the helical axis (FIG. 12C). The 3D structure of the GV8 monomeric $3_{10}$ helix calculated using a total of 39 NOE constraints (FIG. 14) is shown in FIGS. 12D and 12E. When Val8 was mutated to Leu (GL8) and Ala (GA8), the aromatic interactions between Y3 and Y6 disappeared and both mutated peptides remained in extended conformations (FIGS. 13C and 13D).

To monitor gel formation, both 1D proton and 2D $^1$H-$^1$H NOESY spectra of 20 mM GV8 were recorded during a 4-hour period. The peak intensities of the amide protons arising from residual peptides in solution decreased with time (FIG. 13B), implying that an increasing amount of peptide underwent structural rearrangement and were incorporated in the hydrogel.

Figure 15A:
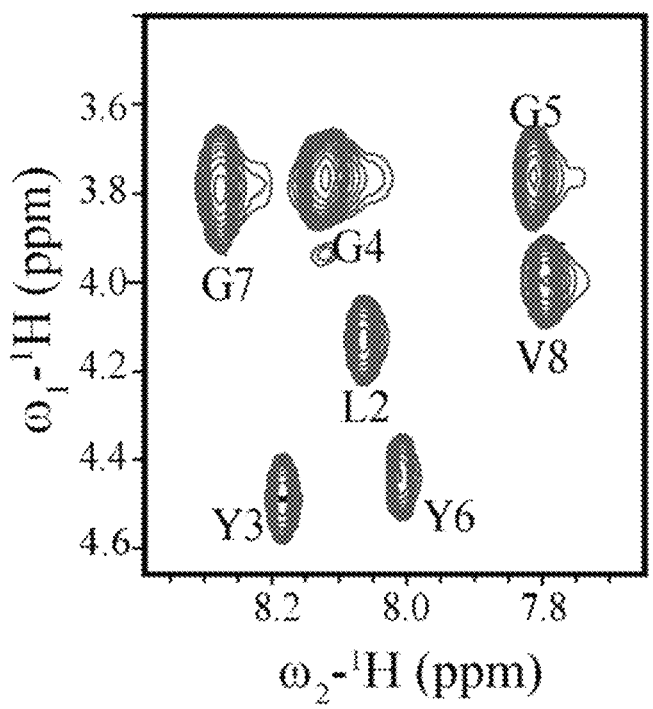
FIG. 15A-15E. Solution NMR characterization of GV8 at oligomeric concentration (20 mM).
Figure 15B:
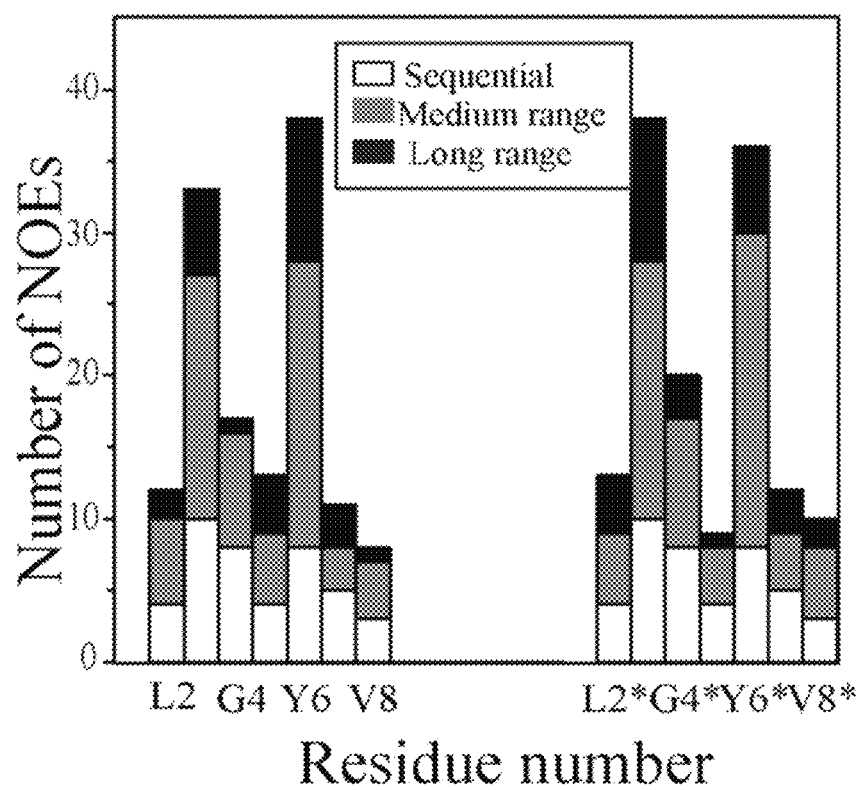
Figure 15C:
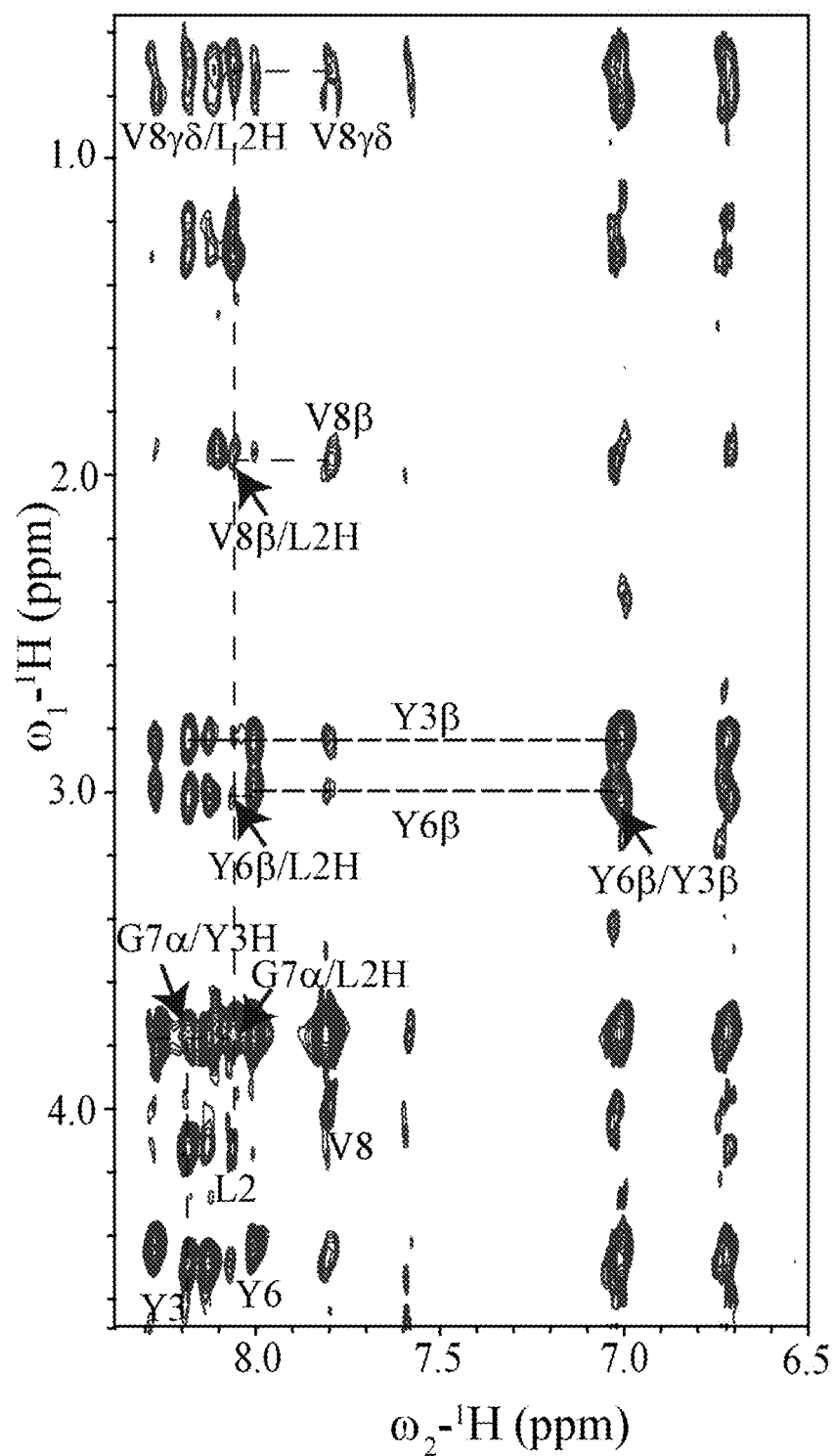

Analysis of 2D $^1$H-$^1$H TOCSY spectra acquired after 20 hours demonstrated well resolved cross-peaks corresponding to individual spins of GV8 peptide (FIG. 15A). 2D $^1$H-$^1$H NOESY spectra displayed the (i, i+3) NOEs that are fingerprints of a $3_{10}$ helix (G. L. Millhauser et al. *J. Mol. Biol.* 1997, 267, 963) as shown in FIG. 15C. Strikingly, residues at the C-terminal (G7 and V8) were involved in displaying long range NOEs with residues at N-terminal (Y3 and L2) (FIG. 15C). The H$^\alpha$ of G7 interacted with L2 and Y3 residues (arrows and dotted lines, FIG. 15C) and side chain β protons of V8 were also found to interact with L2 protons. These long-range NOEs are attributed to cross-strand NOEs resulting from oligomerization of the GV8 peptide after 20 hours (FIG. 15B). The aromatic packing interactions between Y3 and Y6 were also clearly detected owing to the high peptide concentration (FIG. 15C).

Figure 15D:
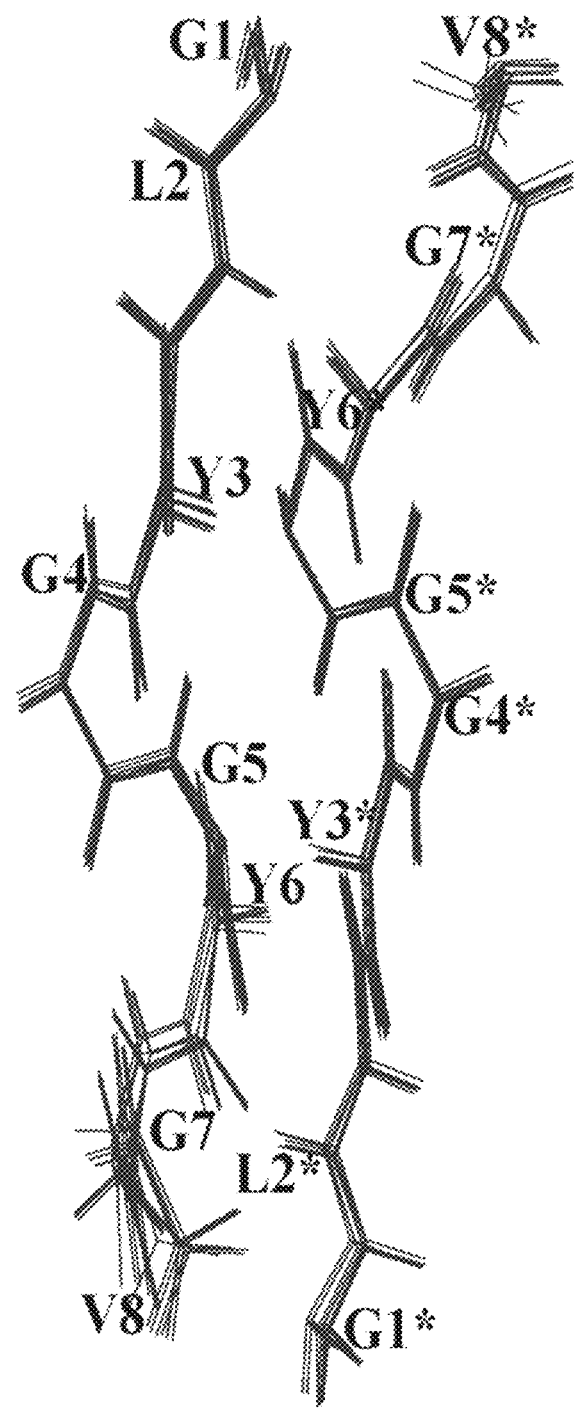
Figure 15E:
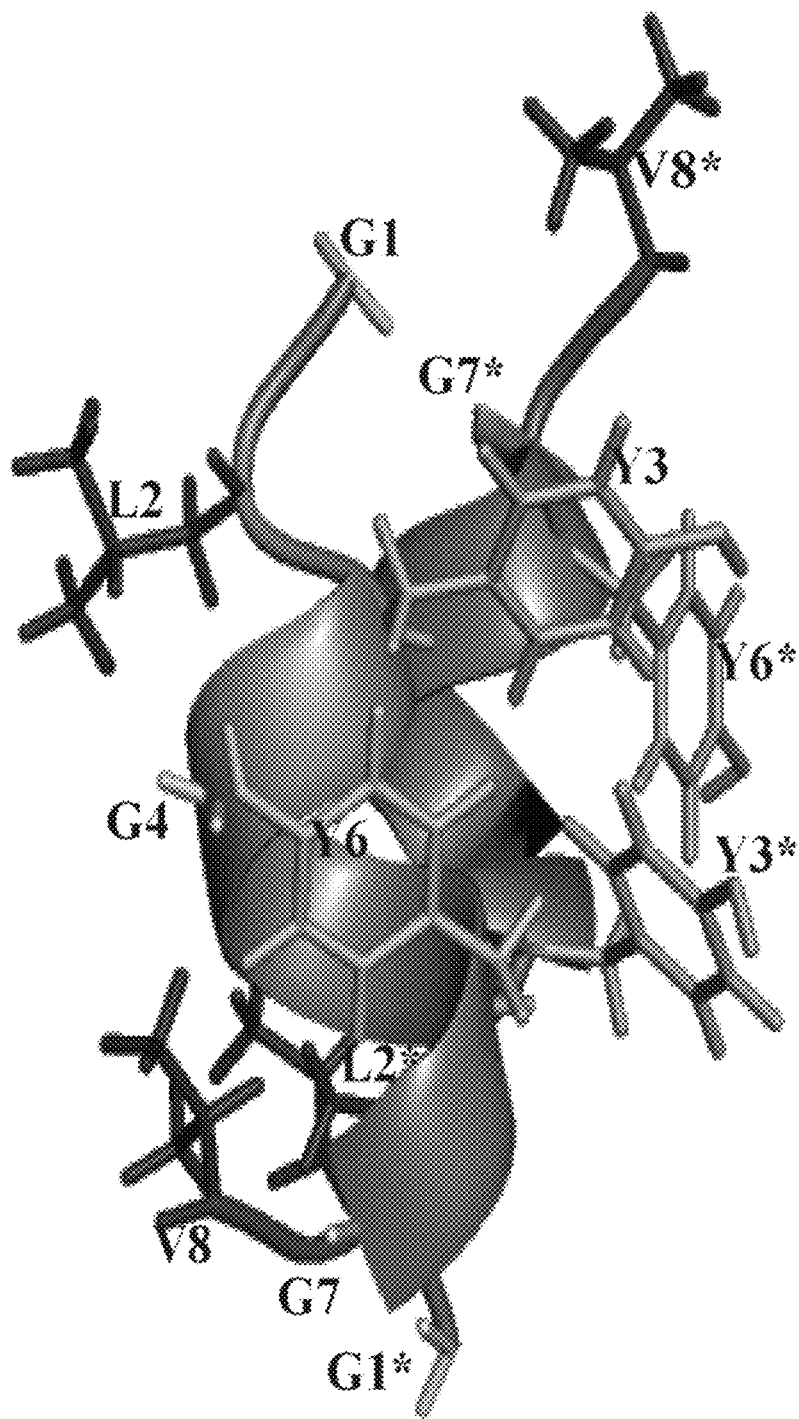

Using a total of 138 NOE constraints (FIG. 14), we calculated an ensemble of 10 structures for GV8 composed of dimeric $3_{10}$ helical building blocks (adding 5 Gly as a linker between the two monomers). The aromatic residues Y3 and Y6 delineated a higher number of medium and long-range NOEs (FIG. 15B). Superposition of 10 lower energy conformers led to root mean square deviations (RMSD) of backbone and heavy chains of 0.65 Å and 0.70 Å, respectively (FIGS. 14 and 15D). 3D structure calculation revealed that the hydrophobic face of the dimeric $3_{10}$ helix is composed of π-stacking interactions between Y3 and Y6, while the exposed side of the dimeric helix is made up of aliphatic side chains L2 and V8 (FIGS. 15D and 15E). Procheck analysis of the 3D structure revealed that all residues resided in the sterically allowed regions (FIG. 14).

1.6 Amide Temperature Coefficient and H/D Exchange NMR Studies

Figure 16A:
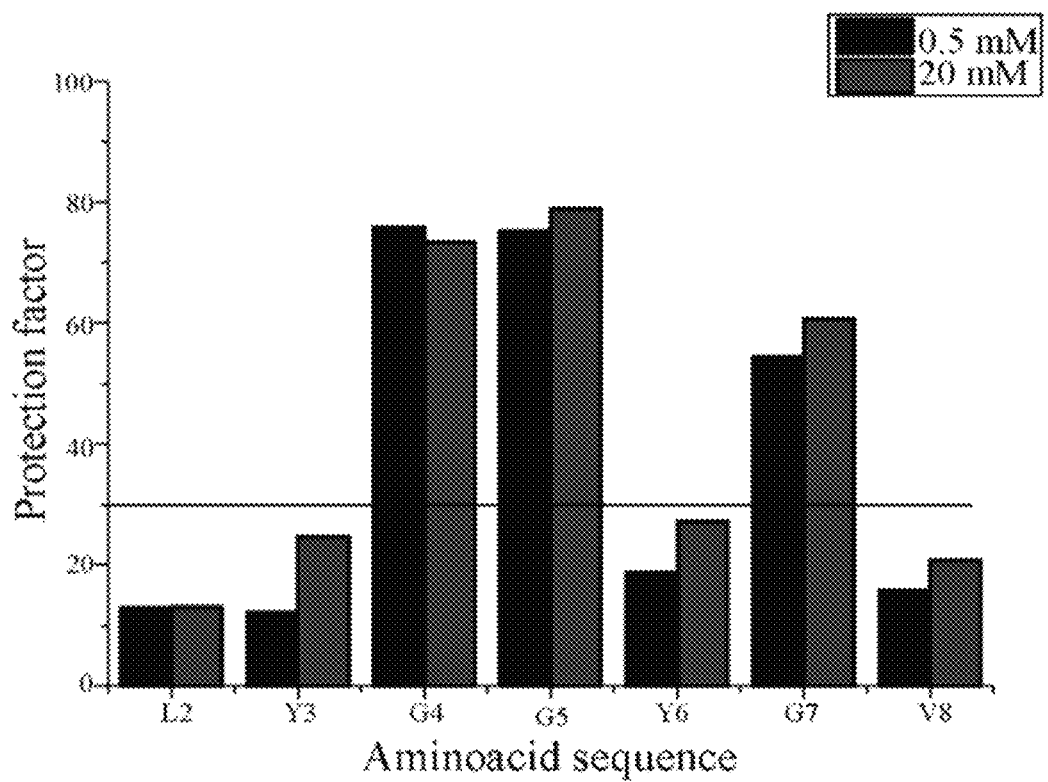
FIG. 16A-B. Validation of hydrogen bonds stabilization by H/D exchange NMR and Temperature coefficient parameter.
Figure 16B:
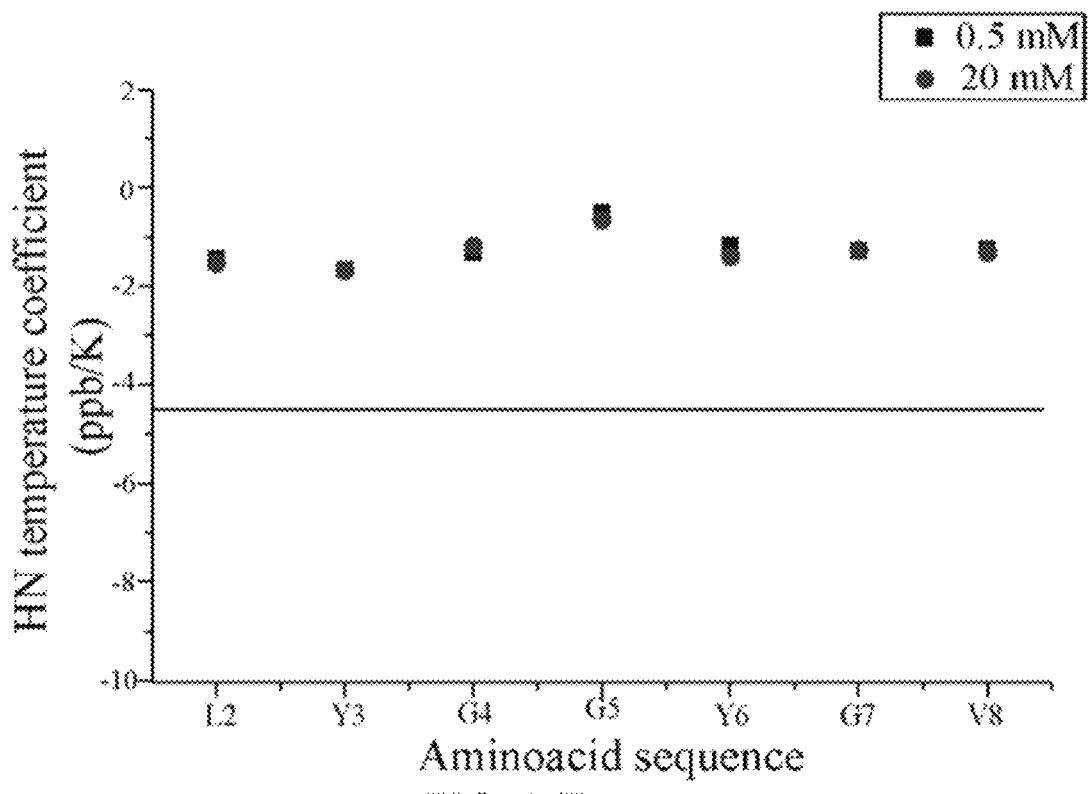

The role of hydrogen bonds in stabilizing the $3_{10}$ helix was studied by calculating the protection factors from H/D exchange as well as the amide proton temperature coefficients ($\Delta\delta_{NH}/\Delta T$) at various temperatures. A series of 2D $^1$H-$^1$H TOCSY spectra were recorded every 30 min for the 0.5 mM and 20 mM GV8 peptide dissolved in D$_2$O. All Gly residues for both the monomer (0.5 mM) and the oligomer (20 mM) concentrations displayed protection factor of 60 to 80, supporting a significant H/D exchange protection inside the core of the $3_{10}$ helical structure (FIG. 16). The protection factor of Y3 and Y6 increased with the peptide concentration, indicating enhanced aromatic interactions for the oligomeric form (FIG. 16). Comparably, the amide proton temperature coefficients of all GV8 residues at both monomer and oligomer concentrations exhibited values more positive than −4.6 ppb/K (J. O. Tornasz Cierpicki. *J. Biomole. NMR.* 2001, 21, 249). The Gly residues also exhibited more positive values in line with their higher protection factor values (FIG. 16).

1.7 Solid State NMR

Figure 17A:
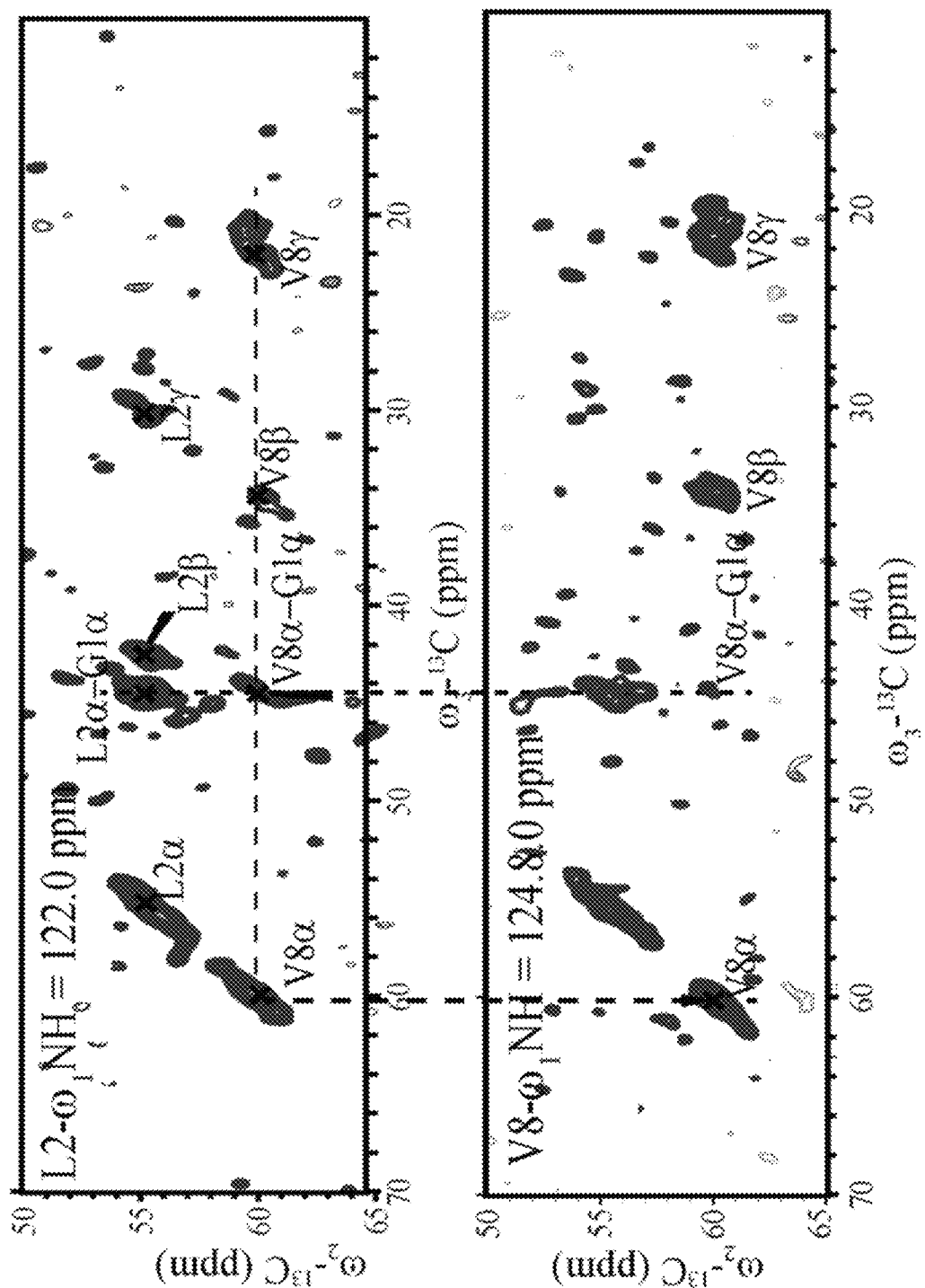
FIG. 17A-17D. Solid NMR characterization of $^{13}$C-$^{15}$N labeled GV8 hydrogel.
Figure 17B:
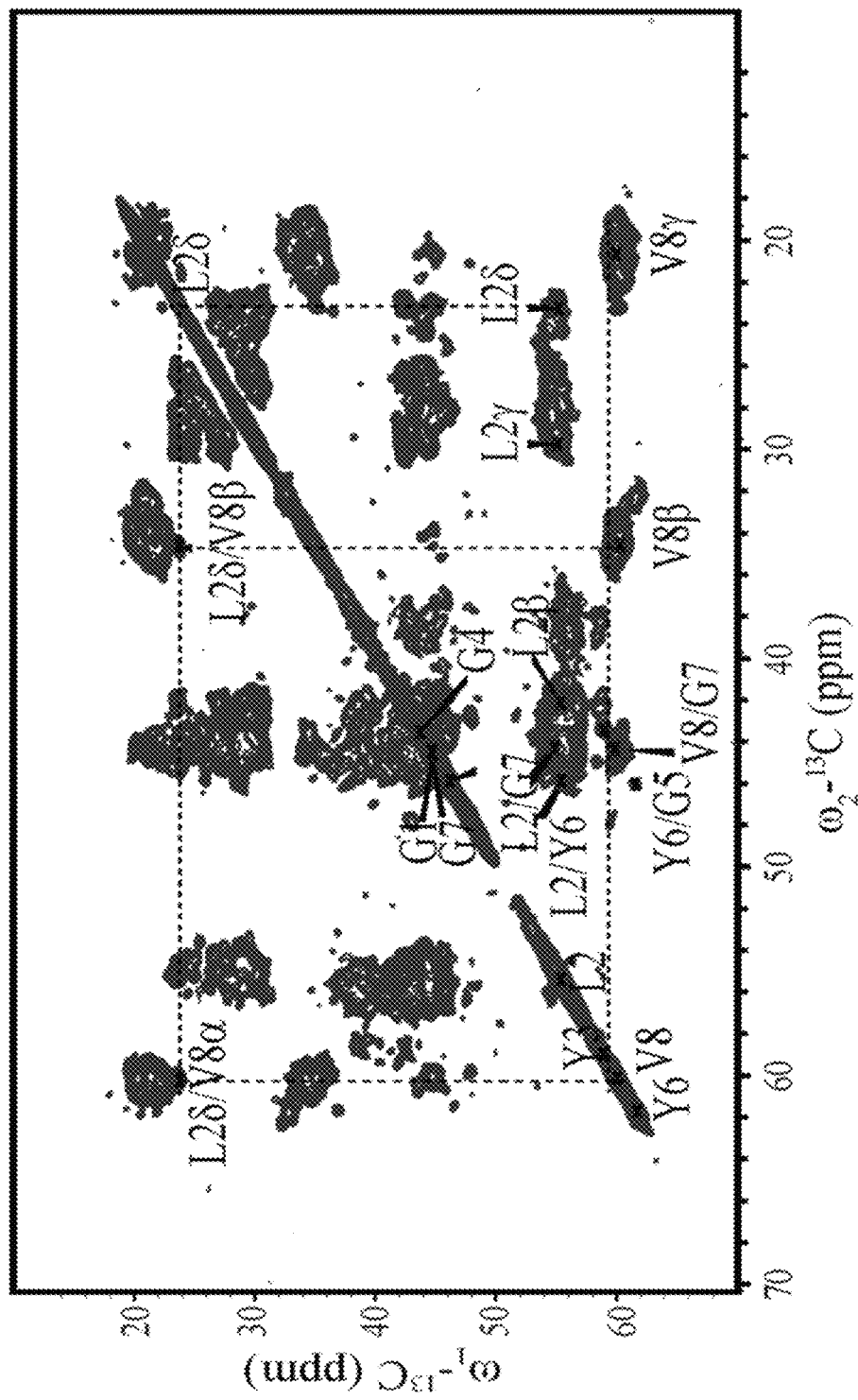

NMR characterizations of the gel state were conducted by ssNMR under Magic Angle Spinning (MAS) conditions. All amino acids of GV8 hydrogel prepared with uniformly labeled $^{13}$C and $^{15}$N peptide were unambiguously assigned using the sequential walking method of 3D NCACX, NCOCX and CANcoCX spectra (FIG. 17A). Analysis of the 2D $^{13}$C-$^{13}$C DARR spectra acquired at 50 ms contact time revealed long range dipolar contacts between L2 and V8 side chains (FIGS. 17A and 17B). The Y3/Y6 ring packing interactions that were detected in oligomeric solutions of GV8 were no longer present in the hydrogel state.

Figure 17C:
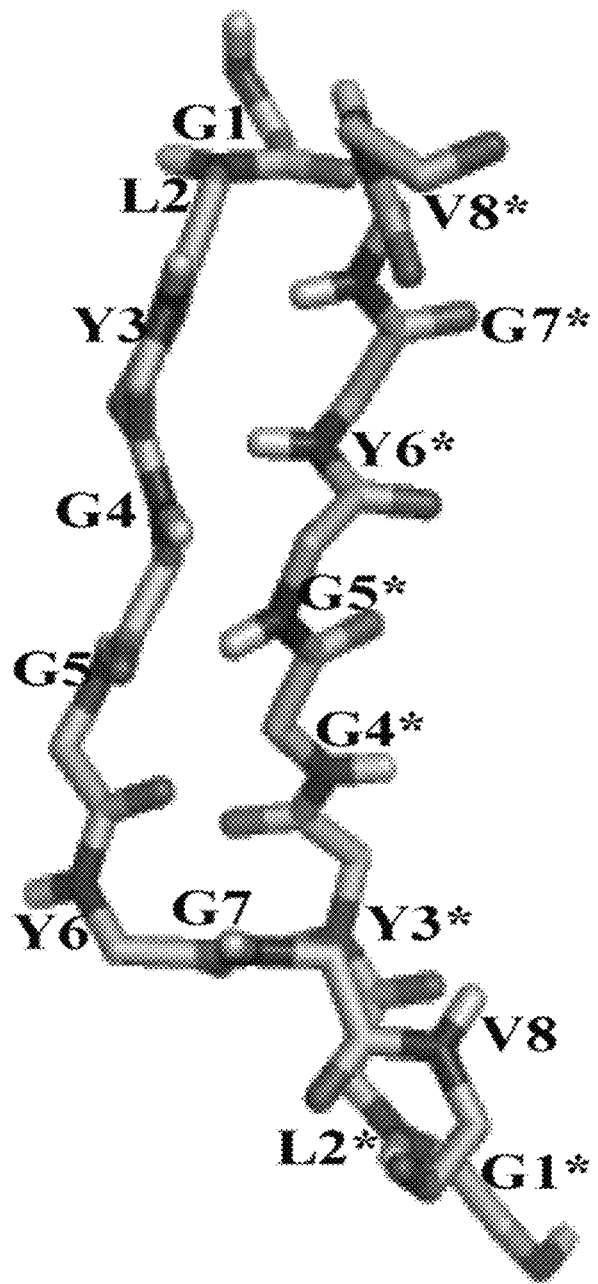
Figure 17D:
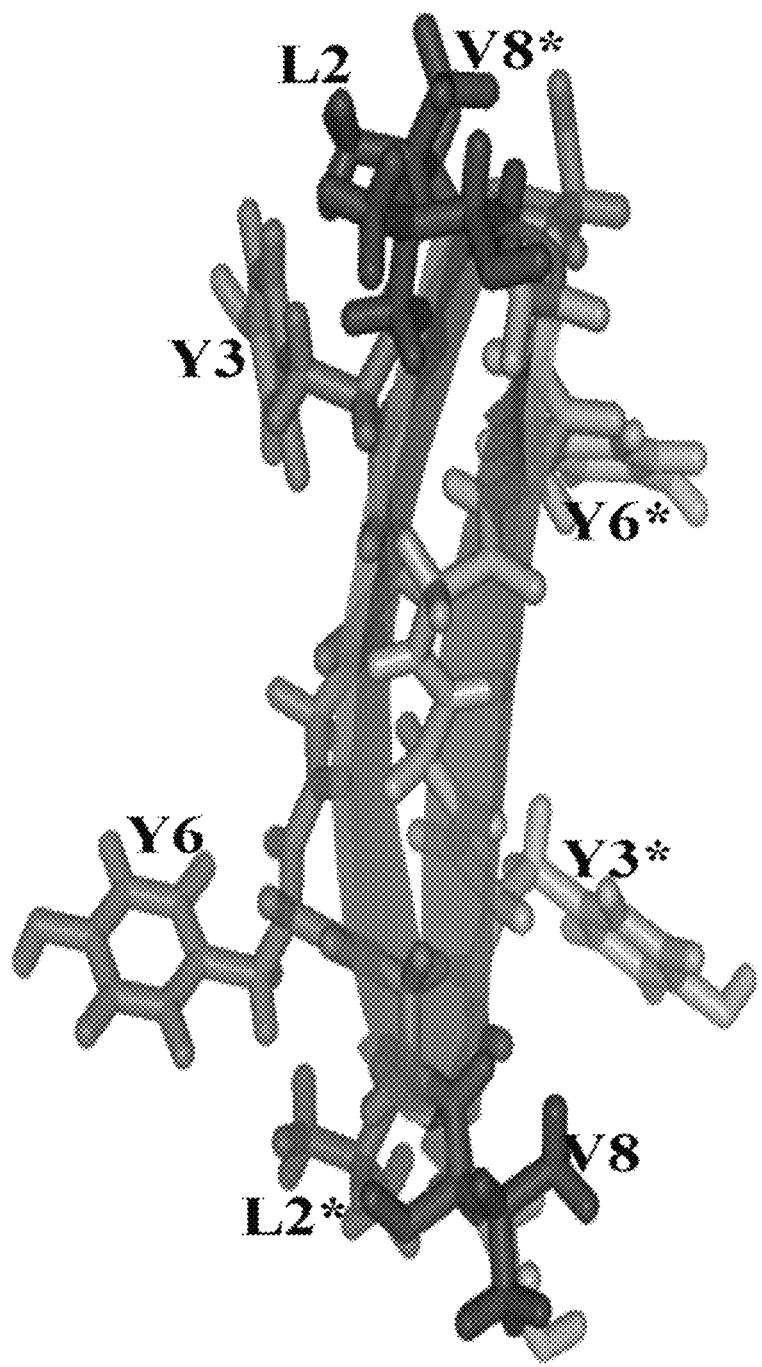

We then calculated the dimeric conformation of GV8 in the hydrogel state using intra-residue and sequential dipolar constraints. An overview of 10 lowest energy structures resulted in RMSD value of 1.49 Å for backbone atoms and 1.75 Å for heavy side chain atoms (FIG. 14). The lowest energy structure revealed that the GV8 hydrogel comprised of extended anti-parallel β-sheets (FIG. 17C). The absence of Tyr ring packing interactions strongly suggests that during gelation, Tyr side chains (Y3 and Y6) rearranged to be exposed to solvent, and that at the same time stronger hydrophobic interactions between L2, V8, L2* and V8* stabilized the antiparallel β-strand conformation of the GV8 hydrogel (FIG. 17D). Extended $3_{10}$ helices have been shown to act as intermediate seeds for the formation of amyloid (β-sheet rich) aggregates (Y. Singh et al. *Chem.—A Eur. J.* 2011, 17, 151), but to the best of our knowledge it has previously not been reported to induce hydrogel formation. Furthermore, none of the Val8-mutated peptides (FIG. 4) gelled under the same conditions and neither control peptides GL8 nor GA8 formed $3_{10}$ helices in solution (FIGS. 13C and 13D) hence corroborating that $3_{10}$ helix is a critical transient conformation leading to gelation of GV8. Val8 at the C-termini therefore plays a crucial role in stabilizing the $3_{10}$ helix structural intermediate by hydrophobic interactions, and the inability of GA8 and GL8 to form well-defined $3_{10}$ helices was attributed to the absence of Val.

1.8 WAXS of Extruded GV8 Hydrogel and MD Simulations

Figure 9B:
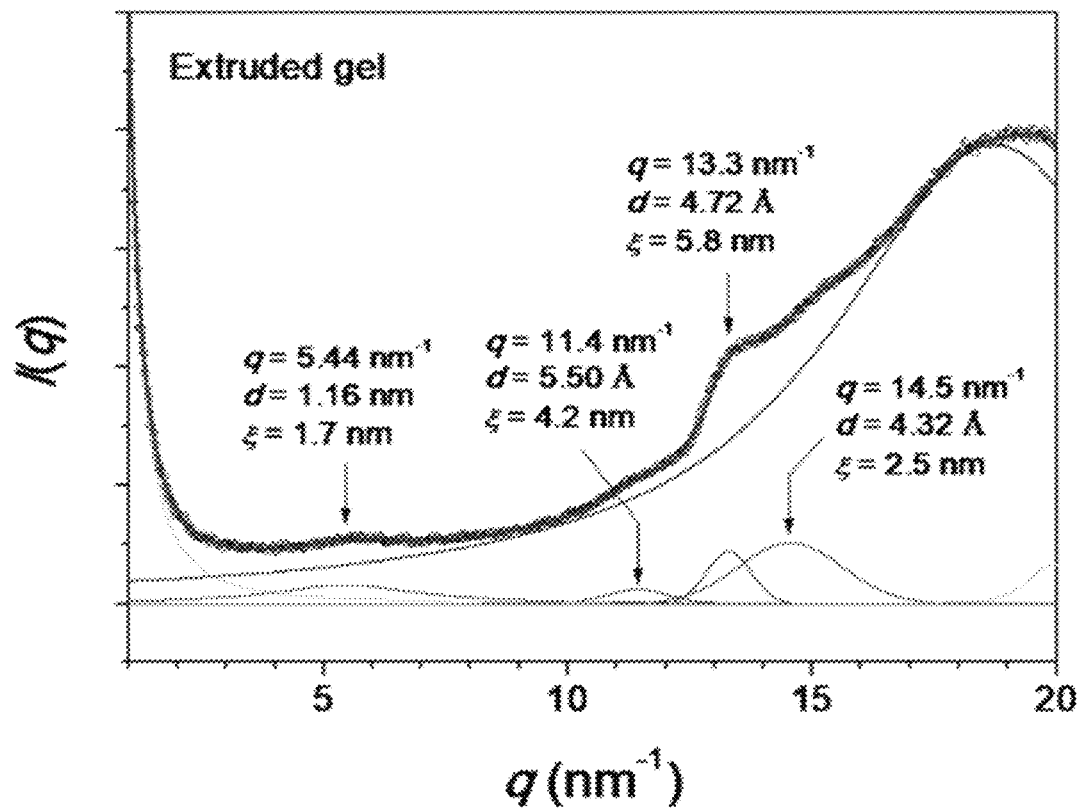
Figure 9C:
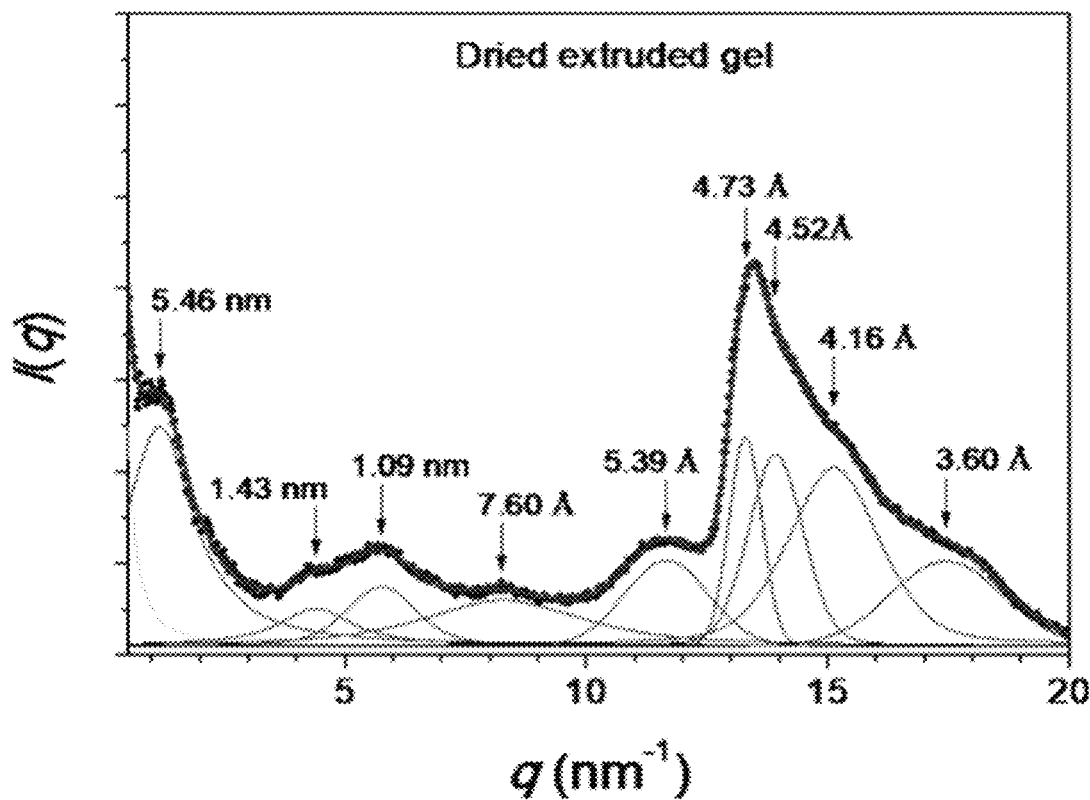

Confirmation of β-sheet presence in the gel was gained by performing WAXS measurements in both the wet and dry states. In the wet state (FIG. 9B) a peak at q=5.44 nm$^{-1}$ and a shoulder at 13.3 nm$^{-1}$ were observed, corresponding to distances of 1.16 nm and 4.7 Å, respectively. These features are the hallmark of β-sheet rich amyloid fibrils, with 1.16 nm corresponding to the inter-β-sheet spacing and 4.7 Å to the inter-strand distance of β-sheets. Interestingly, both features were greatly enhanced upon drying of the gel: the peak at 1.16 nm shifted to 1.09 nm due to dehydration, whereas the 4.7 Å peak now became the dominant scattering peak of the dried gel. The emergence of additional correlations is highlighted by a deconvolution of the intensity profile with Laurentian curves as shown in FIG. 9C.

Figure 18A:
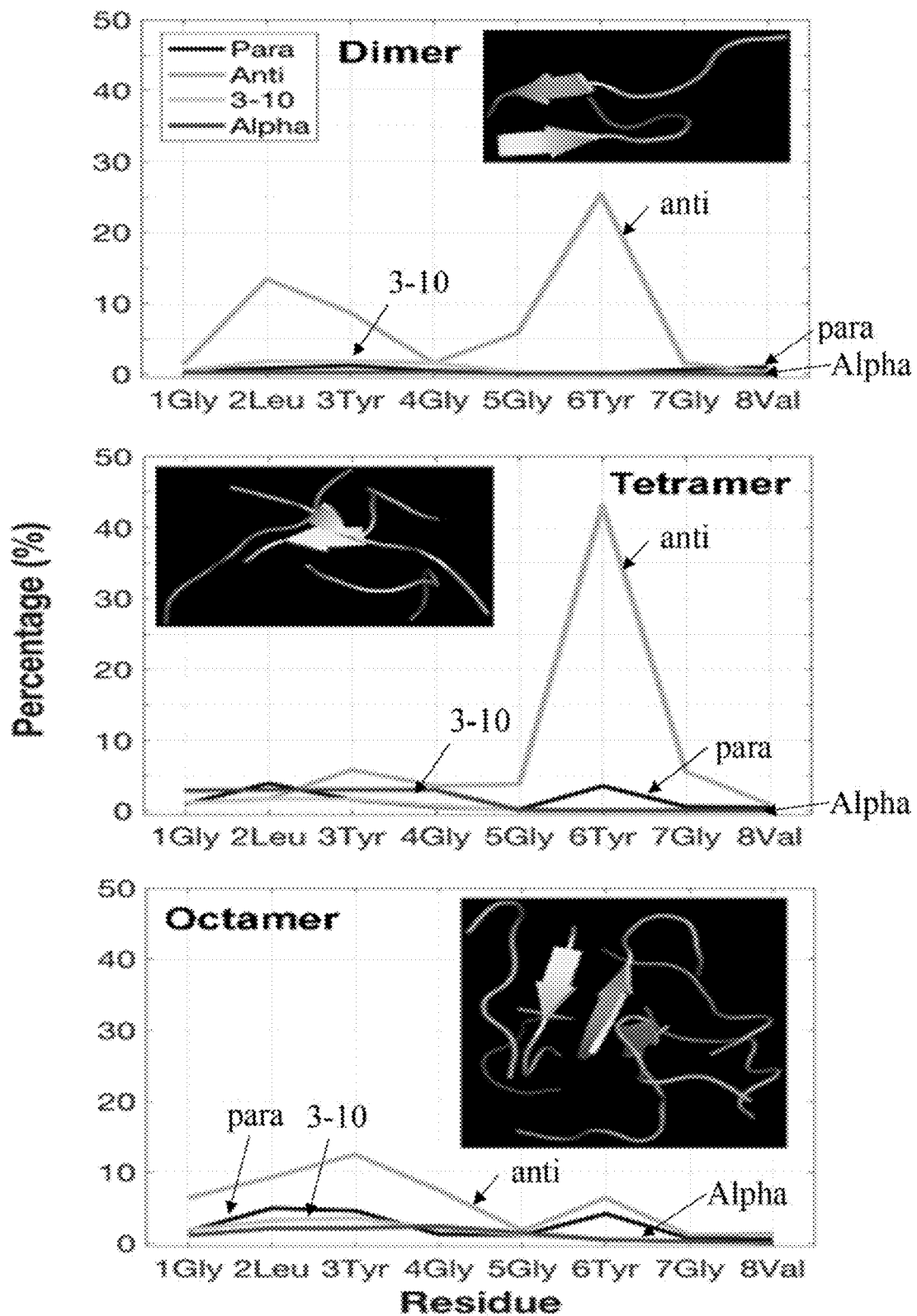
FIG. 18A-18B. MD simulations of GV8 conformation and oligomeric self-assembly.
Figure 18B:
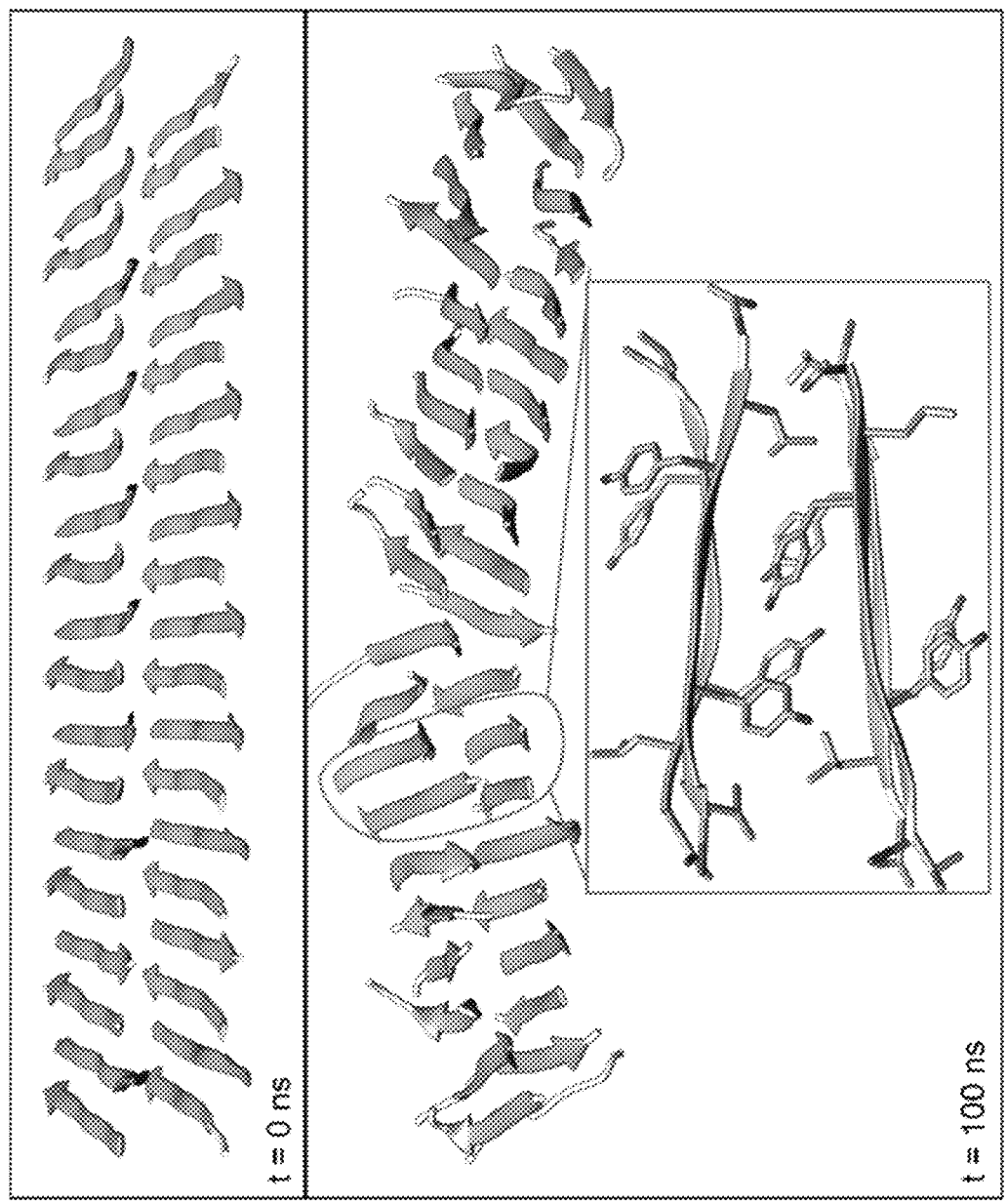

To further assess the conformation propensity of GV8, we conducted MD simulations on both oligomeric and 40-mer constructs. These simulations predicted that oligomers of GV8 prefer the anti-parallel β-sheet conformation, especially the Leu2, Tyr3, and Tyr6 residues (FIG. 18A), whereas $3_{10}$ helices were not stable thus resulting in a very low concentration of $3_{10}$ helices after 200 ns simulations. These results indicate that anti-parallel β-sheets constituted the most stable structure at equilibrium. It is important to emphasize that the peptide concentration during MD simulations is much higher than in the soluble form and more representative of the gel state. Therefore, the very low concentration of $3_{10}$ helices at equilibrium is in line with the conformational transition detected in the gel by NMR. Based on solid-state NMR and WAXS data in the gel state, we then conducted simulations on a 40-mer anti-parallel β-sheet construct. The 100 ns simulation indicated a very high stability of anti-parallel β-sheets, in agreement with the WAXS measurements. Furthermore, the simulations indicated that β-strands were stabilized by inter-sheet π-π stacking of Tyr residues (FIG. 18B). This result corroborates the molecular-level structure of GV8 by solid-state NMR, which indicated that Tyr side-chains in the gel state pointed out perpendicular to the strand direction, making them available to engage in inter-sheet interactions as predicted by the simulations. In addition, in-register anti-parallel β-sheets were observed for both ssNMR and MD simulations, which was postulated to be due to the arrangement of the Tyr side-chains in the least sterically-hindered conformation.

1.9 Conclusion

GV8 is an 8 amino acid long peptide repeat from suckerin-19—the most abundant protein forming the load-bearing squid sucker ring teeth—that forms stiff hydrogels in water with tunable elastic modulus. Using CD, FTIR and solution NMR spectroscopy, we have determined that GV8 self-assembles into unusual $3_{10}$ monomeric helices at low peptide concentration, which are intra-molecularly stabilized by π-π stacking aromatic interactions between Y3 and Y6 residues, as well by the aliphatic side chains L2 and V8. As the concentration increases, GV8 dimerizes into antiparallel $3_{10}$ helices driven by π-stacking interactions between Tyr residues Y3, Y6, Y3*, and Y6*. In the gel state, ssNMR and WAXS measurements indicate that GV8 is made of anti-parallel β-sheets, inferring that gelation proceeds by a $3_{10}$ helix to β-sheet conformational re-arrangement. This mechanism is starkly different from previous reports on fibrous peptide-based hydrogels. During this conformational transition, Tyr side-chains reorient perpendicular to the chain direction according to both ssNMR and MD simulations, allowing to mediate inter-sheet interactions. Peptide-based hydrogels with water gelation and the ability to tune the stiffness 25-fold simply by increasing the peptide concentration may find notable opportunities for biomedical applications, such as tissue engineering, encapsulation of therapeutics, soft tissue adhesives or matrix for stem cell differentiation.

2. Example 2: Characterization of Secretome and VEGF Release by GV8+ Hydrogel

2.1 Rheology Characterization and Circular Dichroism

Figure 20A:
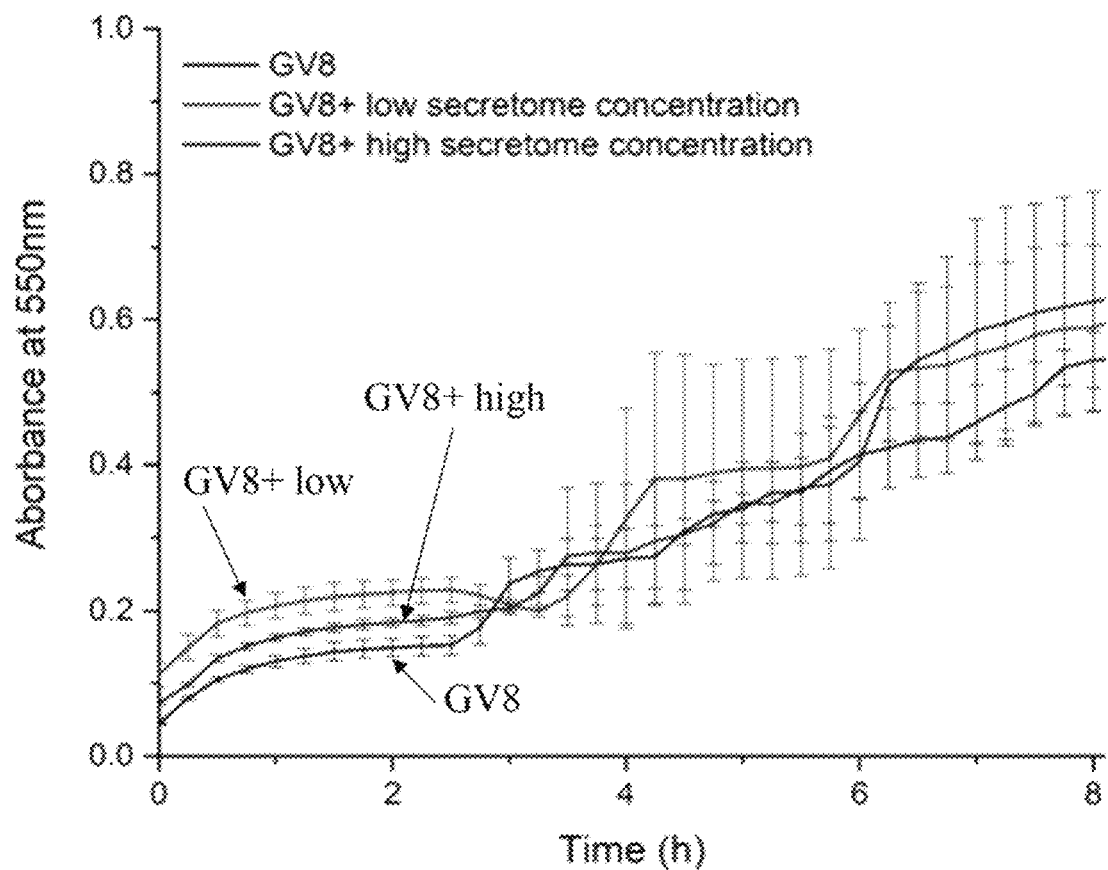
FIG. 20A-20C. Characterization of the gelation process.
Figure 20B:
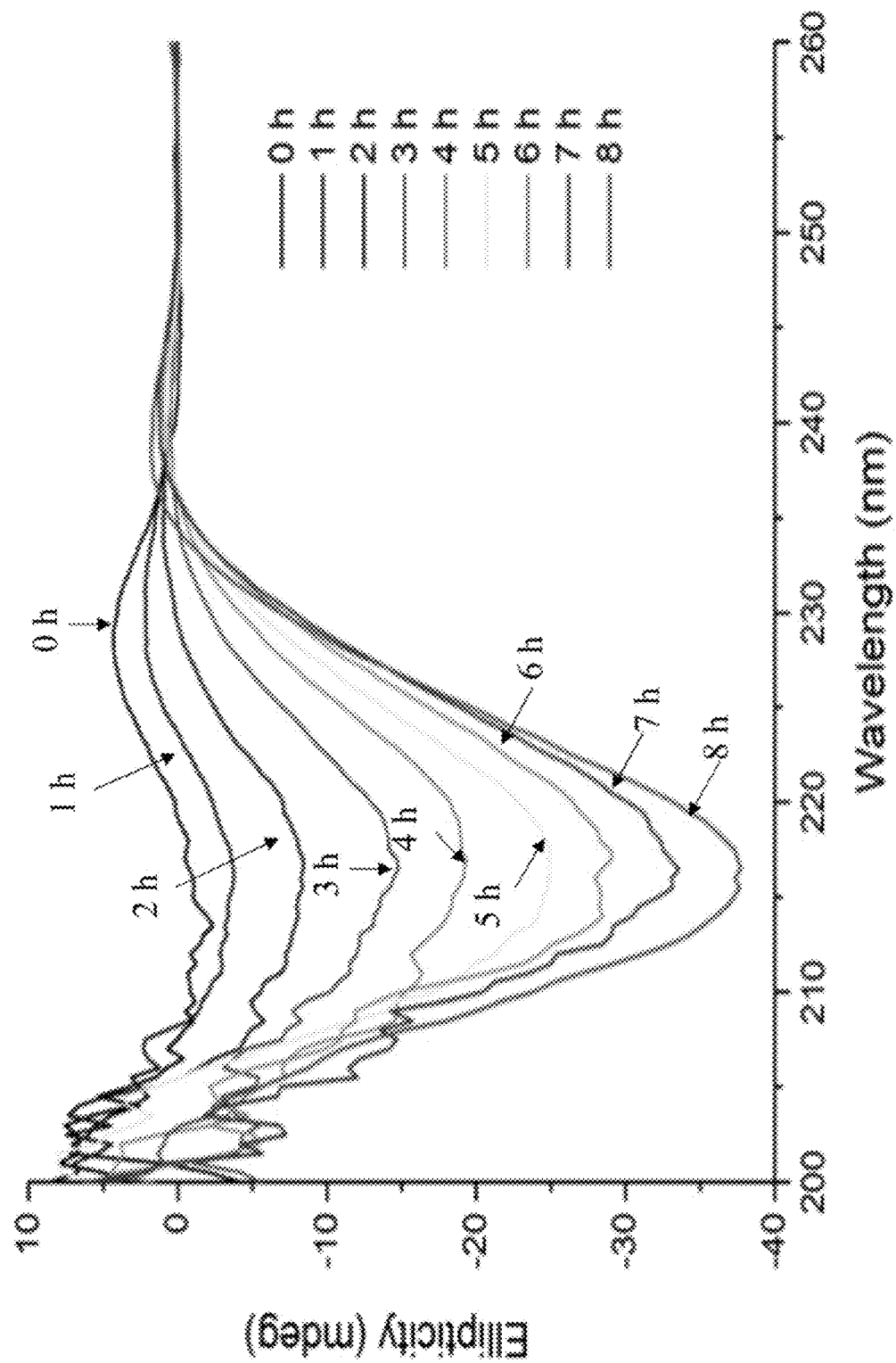
Figure 20C:
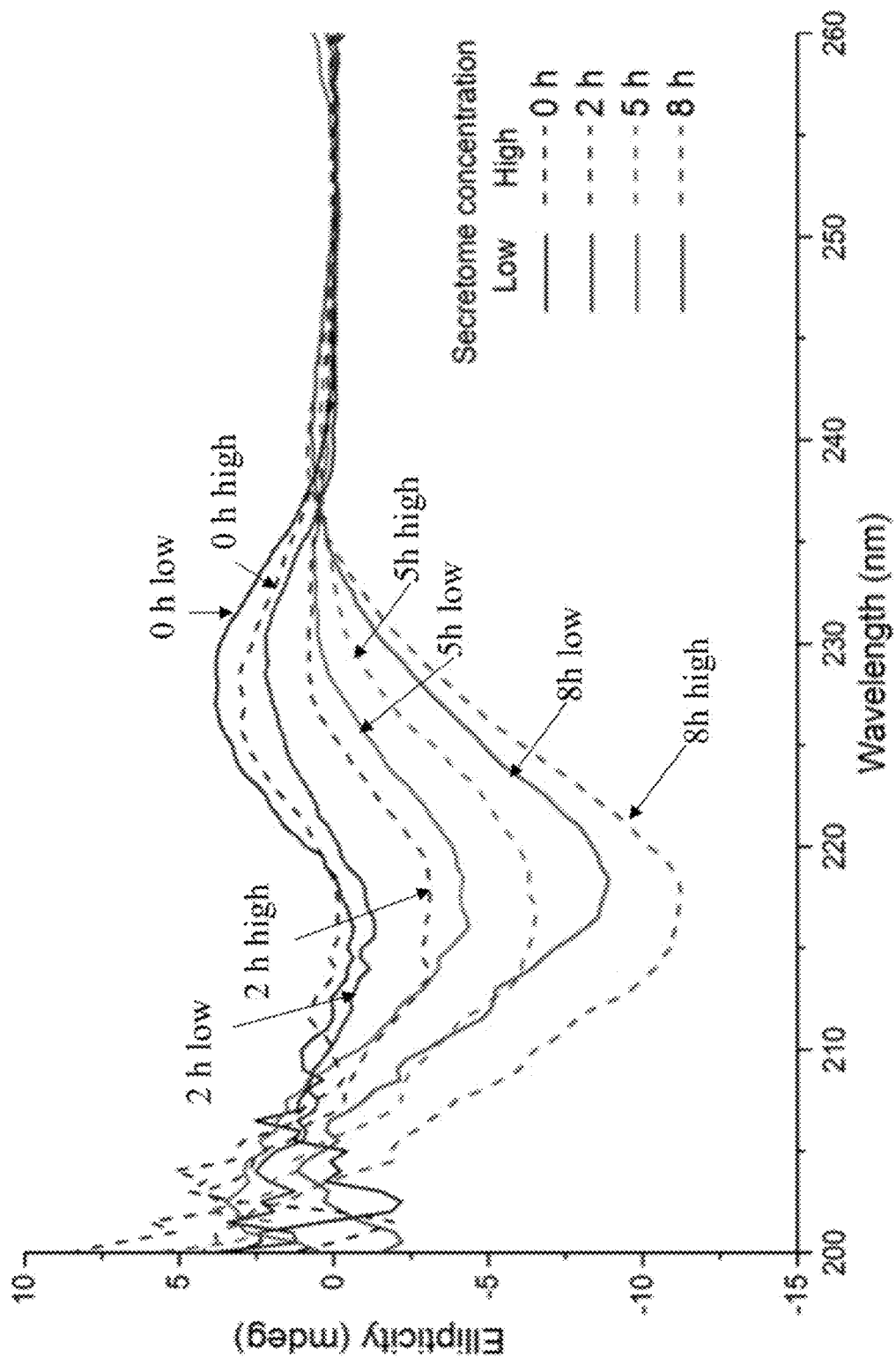
Figure 21A:
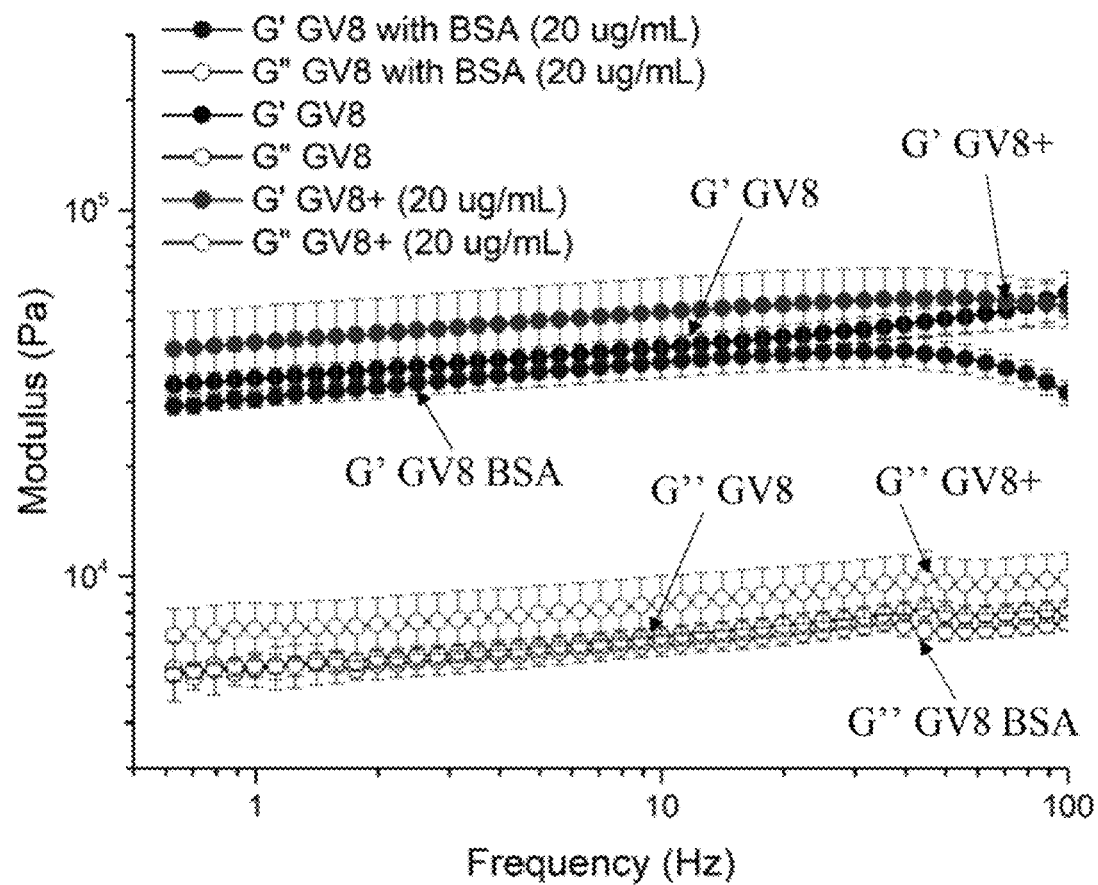
FIG. 21A-21B. Rheological measurements of GV8 hydrogels.
Figure 21B:
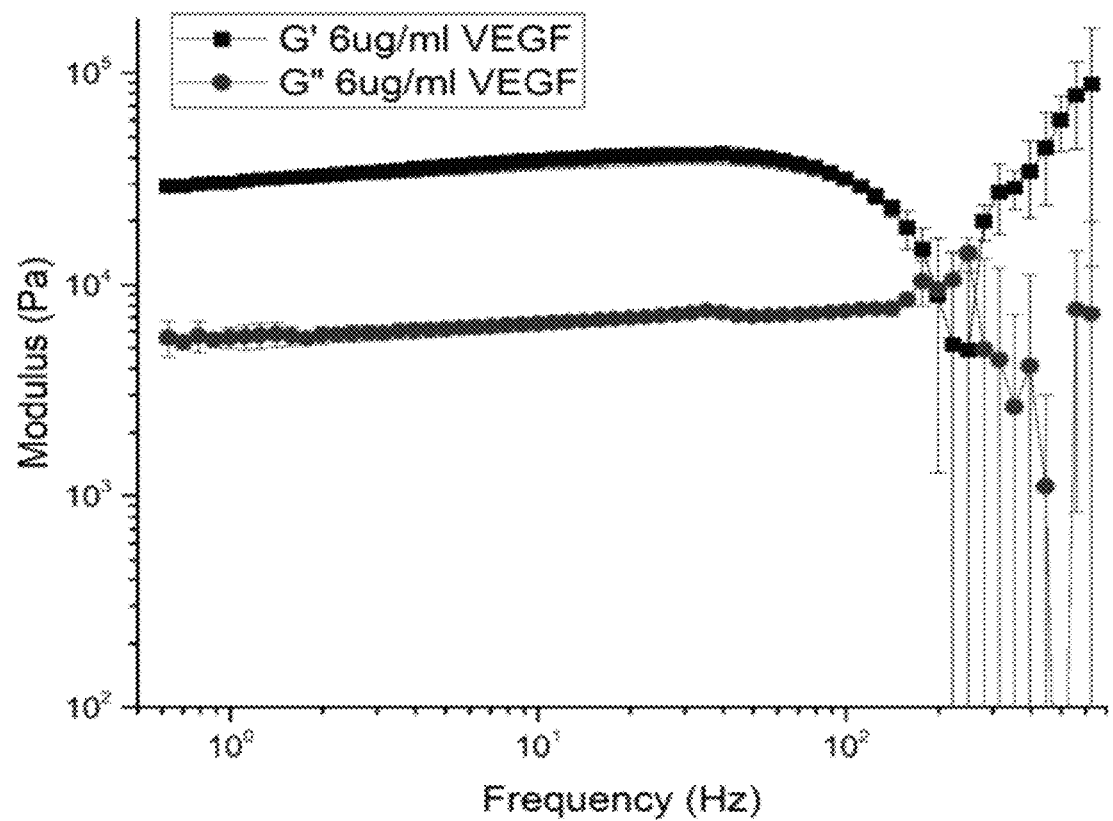

For the fabrication of secretome-loaded GV8+ hydrogel, secretome was loaded into the GV8 precursor prior to gelation. The resulting GV8+ hydrogels showed good structural integrity (FIGS. 3A and 3B), and had enhanced shear modulus (FIG. 19A), suggesting that the incorporation of secretome did not interfere with the overall gelation process, as shown in FIG. 20. The gelation kinetics observed from absorbance at 550 nm (FIG. 20A) indicates an increase in optical density during gelation before reaching a plateau, and the CD spectra obtained during the gelation process showed similar profiles (FIG. 20B) indicative of the $3_{10}$ helix to β-sheet transition as reported above (FIG. 6E). Decreased ellipticity intensities of the CD spectra of GV8+ hydrogel with secretome (FIG. 20C) was anticipated and attributed to the increase in the amount of optically active amide bonds from the protein components within secretome. It was observed that the interaction between secretome components and the GV8 peptide enhanced the structural integrity of the GV8+ hydrogel (FIG. 21A), which was not achieved otherwise by common standard proteins, such as VEGF (FIG. 21B) or BSA with the same loading concentration (FIG. 21). The improvement in the physical properties of the GV8+ hydrogel may be attributed to the physical interactions, such as hydrophobic and π-π interactions between the GV8 peptide and the secretome protein components, resulting in the enhanced structural integrity of the networks.

Figure 19A:
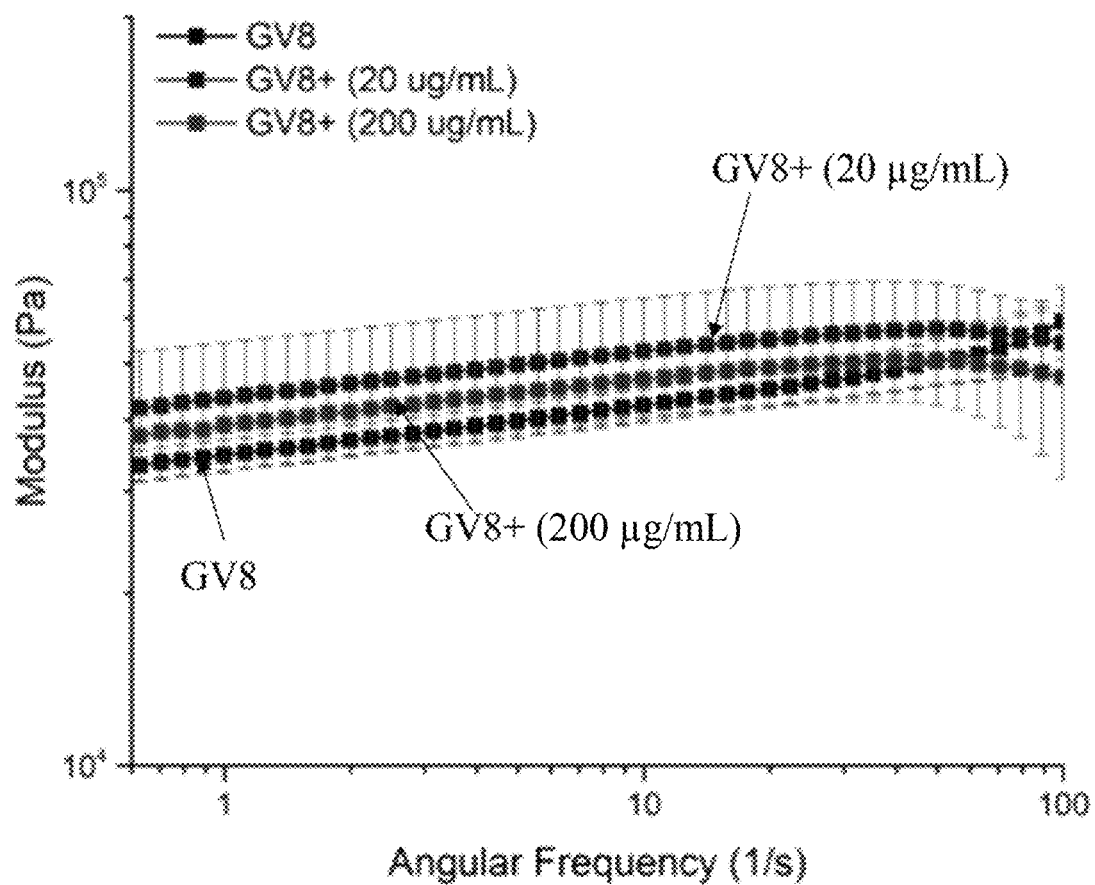
FIG. 19A-19B. Enhanced mechanical properties of GV8 hydrogels with secretome incorporation (i.e. GV8+ hydrogels).
Figure 19B:
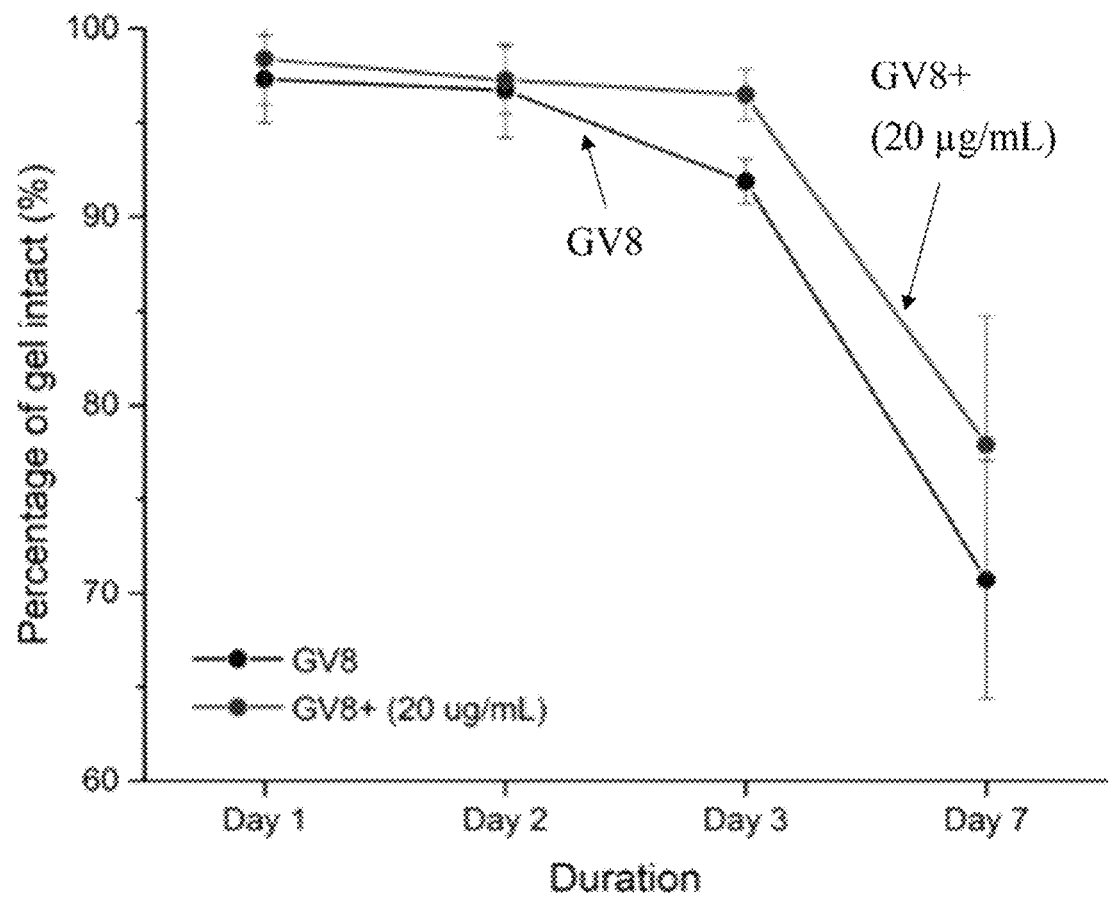

A reduction in the degradation rates (FIG. 19B) was also observed in the GV8+ hydrogel as compared to the GV8 hydrogel, which agrees with the rheological results where the presence of the secretome enhanced the physico-chemical stability of the hydrogels (FIG. 19A).

2.2 Controlled-Release Kinetics of Secretome

Figure 22A:
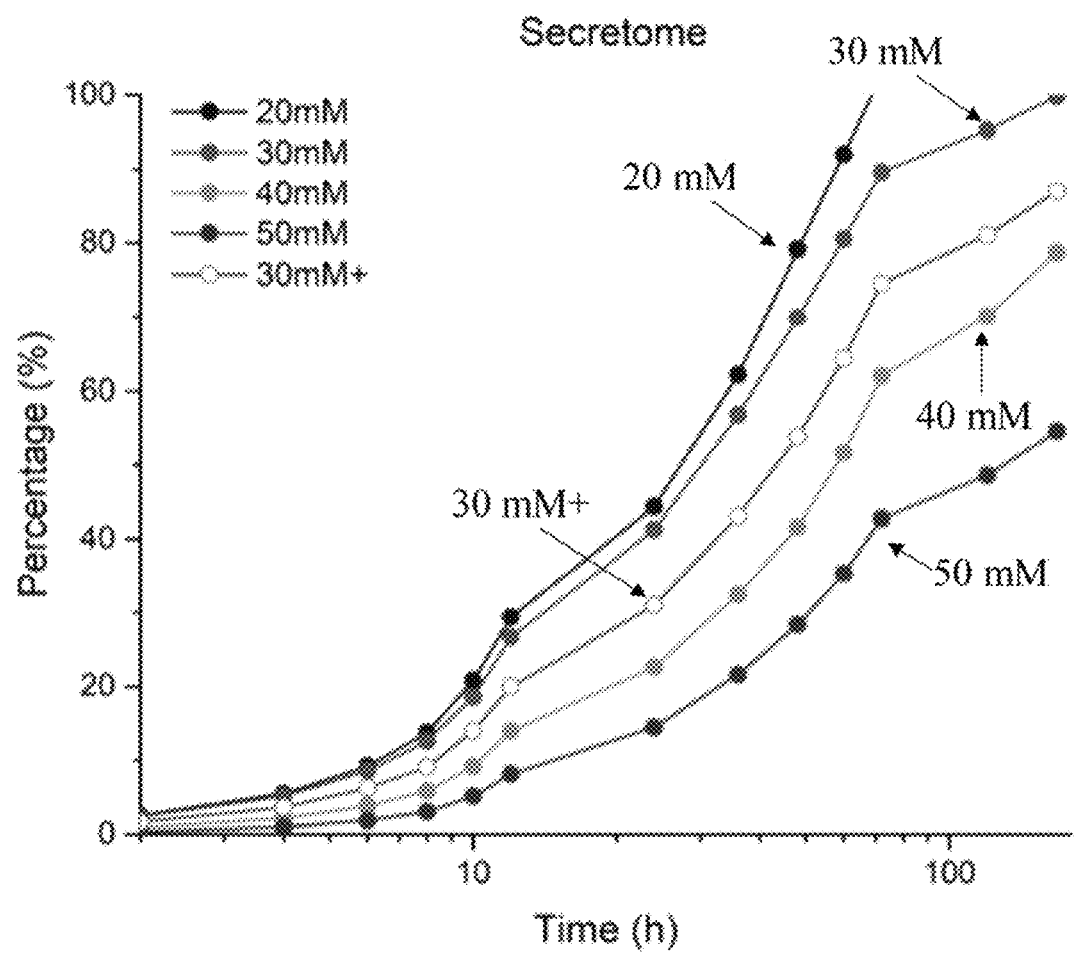
FIG. 22A shows the GV8+ hydrogel percentage release profiles of loaded FITC-tagged secretome. Plot legend indicates GV8 peptide hydrogel concentrations. All hydrogels were loaded with 20 µg/mL of FITC-tagged secretome except for 30 mM+, which was loaded at 200 µg/mL of FITC-tagged secretome.
Figure 22B:
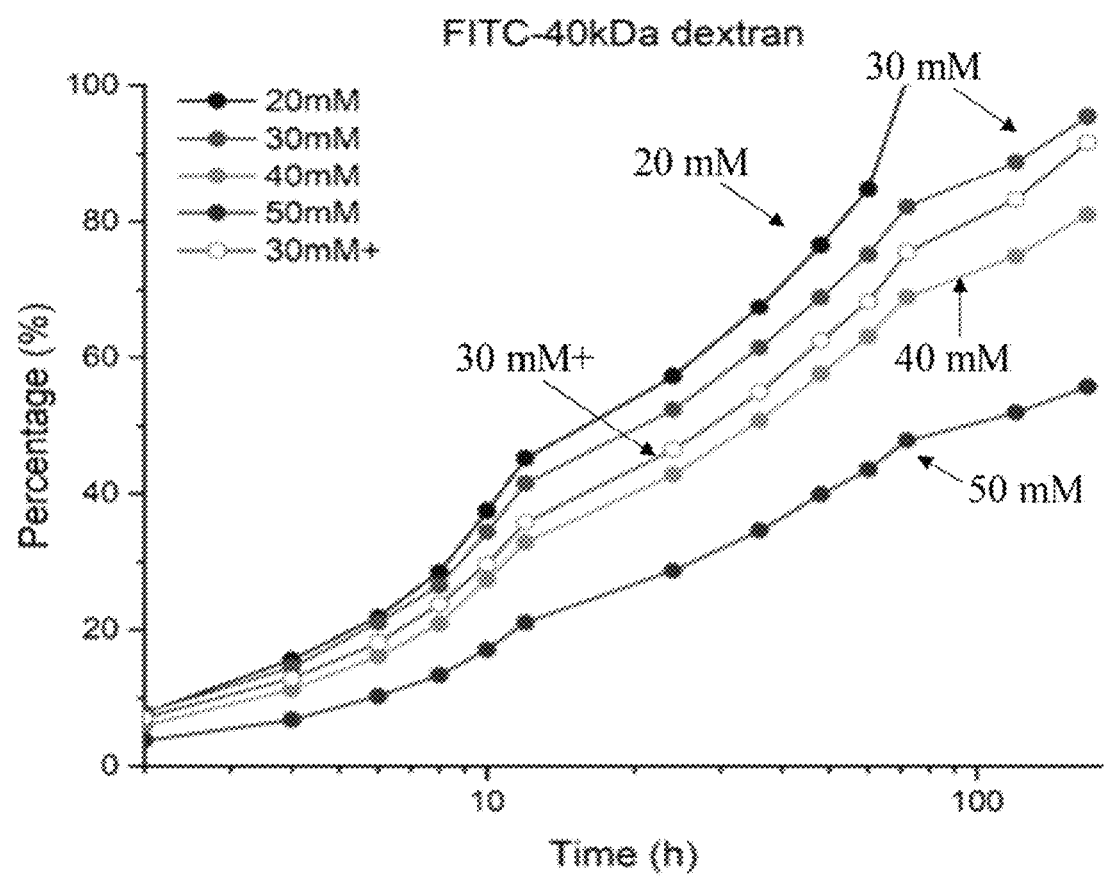
FIG. 22B shows the GV8+ hydrogel percentage release profiles of loaded FITC-tagged 40 kDa dextran in solution. Plot legend indicates GV8 peptide hydrogel concentrations. All hydrogels were loaded with 20 µg/mL of FITC-40 kDa dextran except for 30 mM+, which was loaded at 200 µg/mL of FITC-40 kDa dextran.

The secretome release kinetics was further evaluated as shown in FIG. 22. FIG. 22A shows the secretome release profiles from GV8+ hydrogel with different initial loading densities of secretome (i.e. 20 µg/mL and 200 µg/mL) and at varying GV8 peptide concentrations (i.e. 20 mM to 50 mM). The amount of secretome that was released into the surrounding solution was relative to the initial loading density of secretome. Further analysis suggested that the general trend of percentage release of loaded secretome remained consistent across a range of GV8 peptide hydrogel concentrations, where similar release kinetics was achieved regardless of the initial loading amount. In a separate experiment to investigate the release profiles of non-protein-based molecules, FITC-tagged 40 kDa dextran was loaded and tested in a similar manner (FIG. 22B). GV8 hydrogels were observed to be capable of loading and releasing both compounds, as observed in FIGS. 22A and 22B. Further, the rate of release of the loaded compound can be achieved by adjusting the hydrogel's concentration. It is likely that an increase in the GV8 concentration reduces the porosity of the hydrogel, resulting in a slower release profile of the loaded compound. Further, the interactions between the GV8 peptide and secretome components which strengthened the structural integrity of the GV8+ hydrogels were postulated to avoid burst release behavior, resulting in a sustainable and consistent release profile of the secretome from the GV8+ hydrogels. The unique combination between the GV8 peptide and secretome in GV8+ hydrogels may delay the release of secretome and reduce the diffusion of secretome components within the porous network, resulting in the controlled release of secretome.

2.3 Cytocompatibility Assay

Figure 23A:
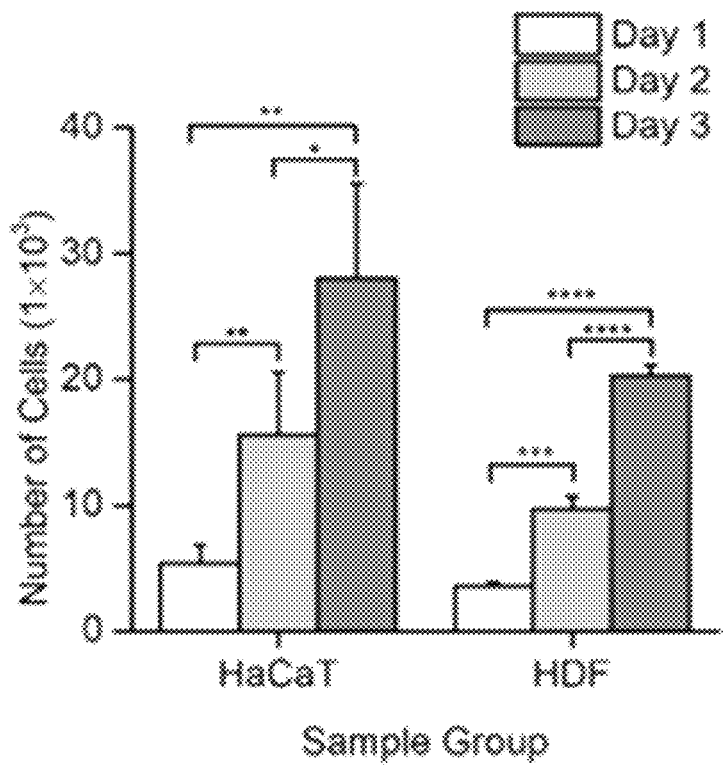
FIG. 23A-23C. GV8 hydrogel cytocompatibility.
Figure 23B:
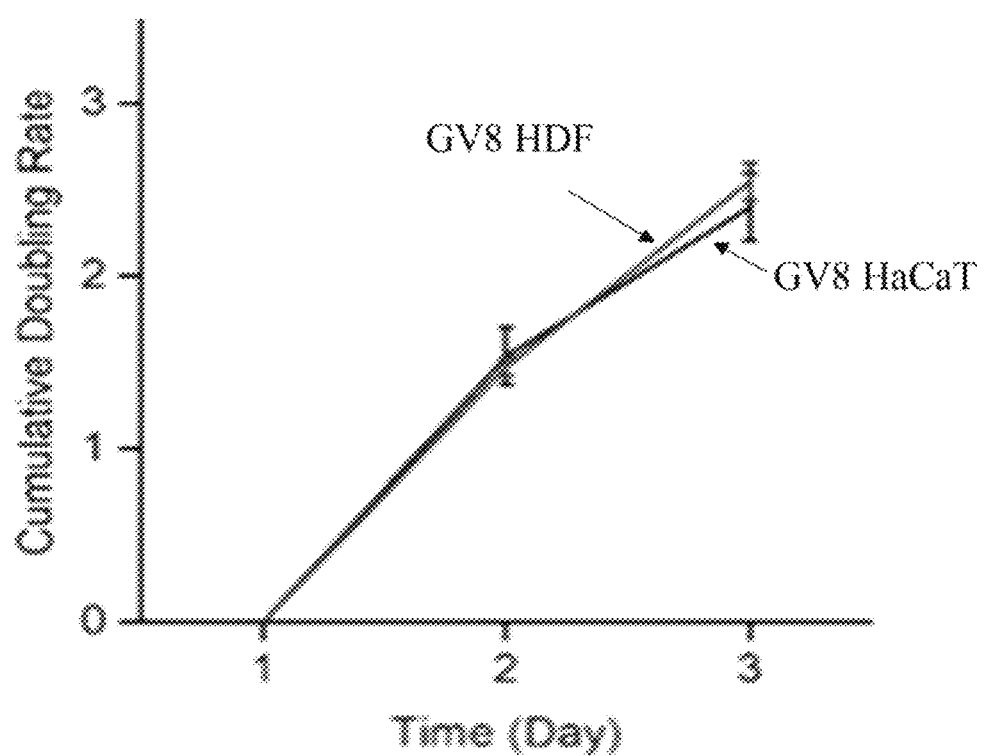
Figure 23C:
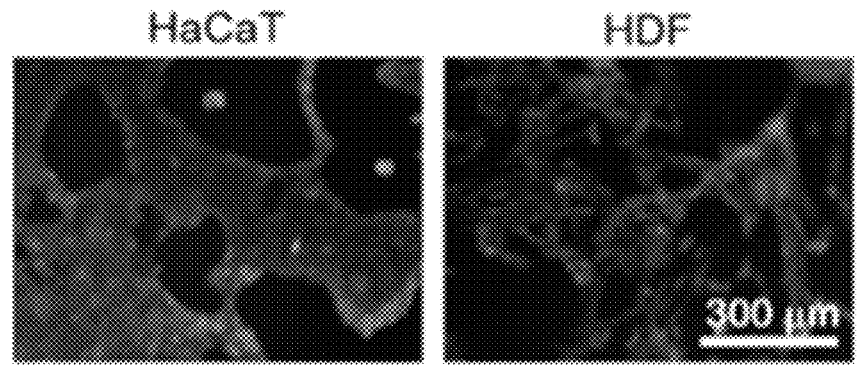

To assess if the GV8 hydrogels were suitable for biological applications, hydrogels of 30 mM peptide concentration were tested for their biocompatibility with HaCaT keratinocytes and HDFs (FIG. 23A). Both HaCaT keratinocyte and HDFs were seeded separately on GV8 hydrogels which were pre-formed in TCP wells and allowed to attach overnight. Statistical analysis of cell proliferation on GV8 hydrogels showed that proliferation for both cell types was significant when comparing the 1 d and 3 d cell counts, indicating that the gel did not hinder cell proliferation. The cumulative doubling rate of HaCaT keratinocyte and HDF cells on GV8 hydrogels are shown in FIG. 23B, illustrating that both cell types proliferate after cell adhesion onto the GV8 hydrogel material. FIG. 23C presents fluorescence staining images of HaCaT keratinocyte and HDF cells on the surface of both GV8 hydrogel at 3 d. Some morphological differences were observed, which may be expected for softer substrates like hydrogels. More importantly, these results show that the cells remained viable on the GV8 hydrogel material, indicating that the hydrogels are biocompatible and non-cytotoxic to skin cells such as keratinocytes and fibroblasts.

2.4 Cell Migration Assay

Figure 24:
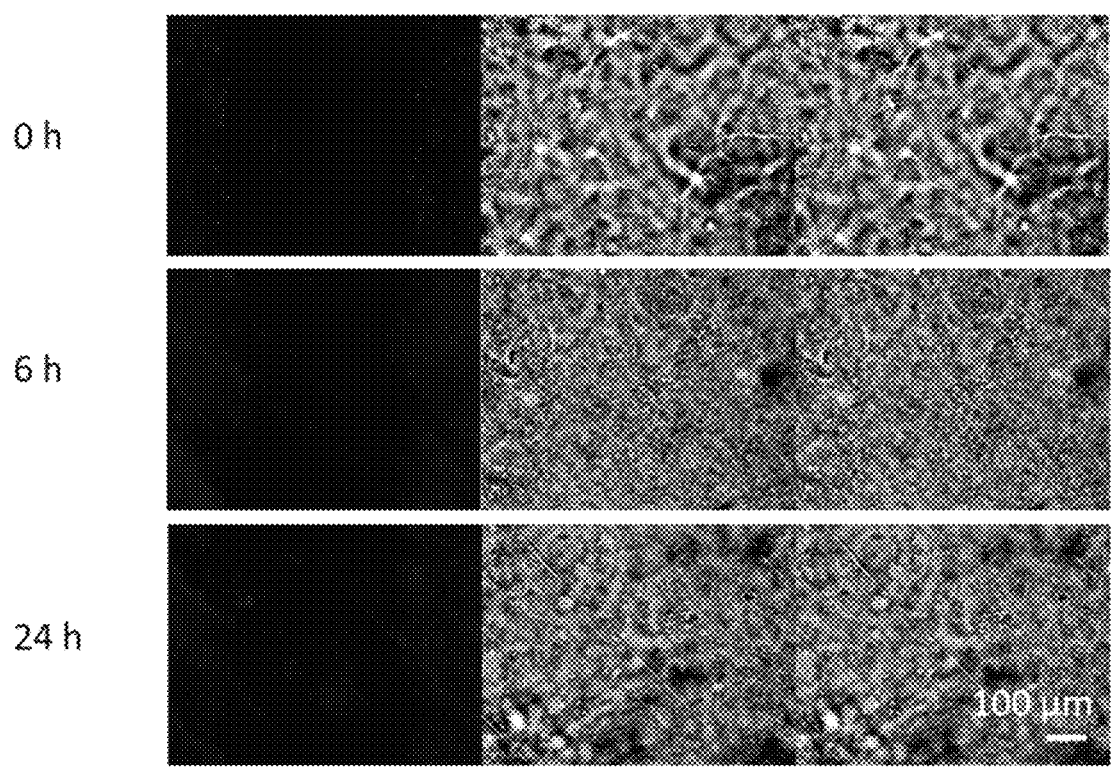
FIG. 24. Scratch-wound assay showing HaCaT keratinocytes cell migration which was observable within 6 h after cell attachment on the GV8+ hydrogel.

A proof-of-concept study was conducted to assess the effect of GV8+ hydrogels on cell migration in serum-starved HaCaT keratinocyte cells. As shown in FIG. 24, GV8+ hydrogels were observed to promote the migration of HaCaT keratinocyte within 24 h, suggesting the suitability of the GV8+ hydrogels for wound applications.

2.5 Angiogensis Assay

To further evaluate the compatibility and wound healing properties of the GV8 hydrogel, GV8+ hydrogel and GV8+ VEGF hydrogel, ex ovo compatibility and the angiogenic potential of the hydrogels were evaluated using the CAM assay with fertilized chicken eggs. It was demonstrated that GV8 hydrogel is safe for ex ovo, given the presence of angiogenesis from the formation of new vessels and thickening of vessels for the fertilized eggs treated with GV8 hydrogel (FIG. 25).

Figure 25A:
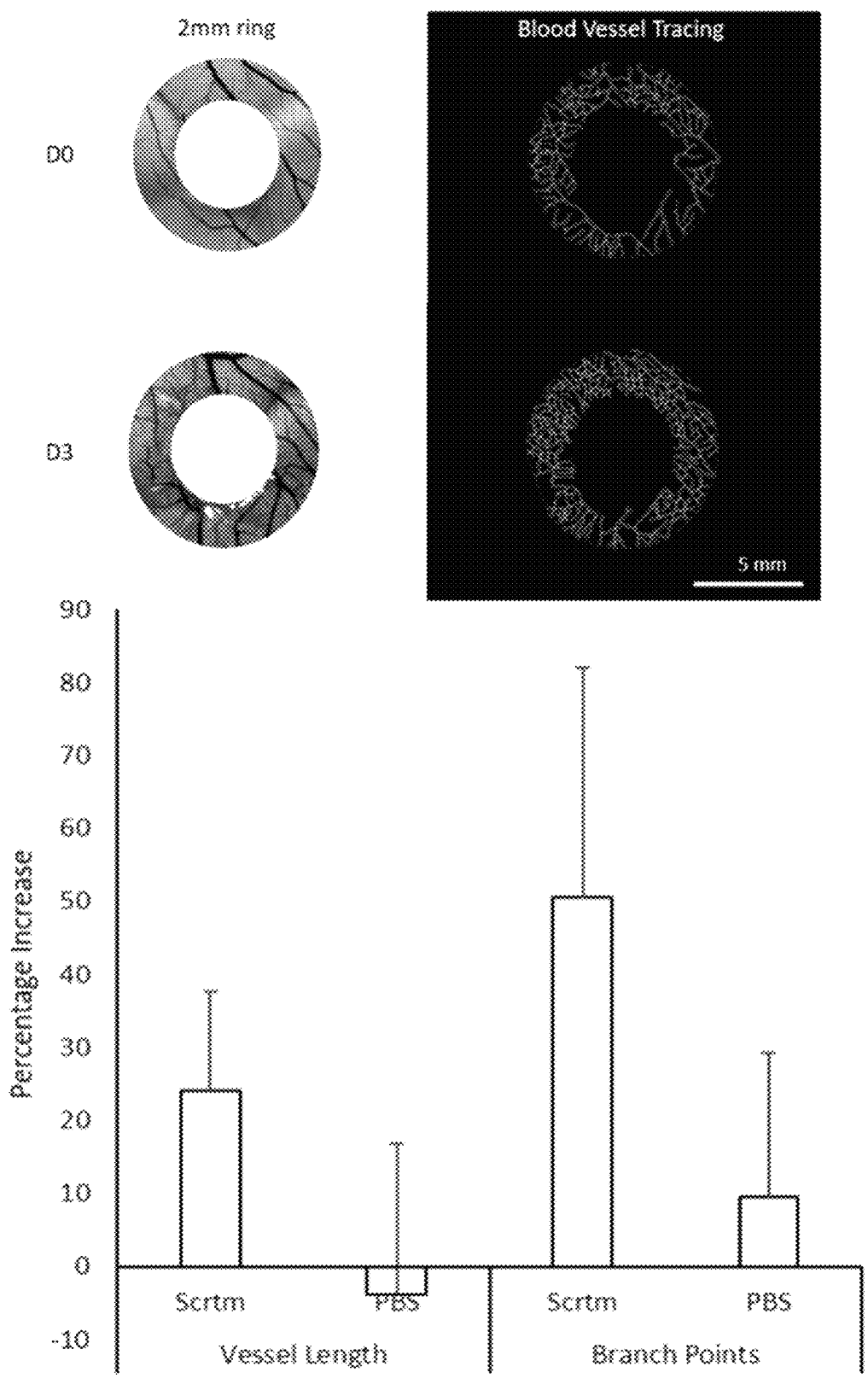
FIG. 25A-25C. Chick chorioallantoic membrane (CAM) assay in GV8+ hydrogels.

GV8+ hydrogels were demonstrated to support and promote angiogenesis in CAM assays as shown in FIG. 25A. After 3 d of GV8+ hydrogel application on the CAM of 11 d old ex-ovo embryos, an increase in the blood vessel length and branch points was observed (as compared to the PBS solution control). The increase in blood vessel length and branch points may be attributed to the consistent release of secretome components from the GV8+ hydrogels which promote and support blood vessel formation. It is likely that the GV8+ hydrogels serve as a reservoir of cytokines and growth factors which is continuously supplied to the wound site to facilitate moisturization, and tissue repair for a period of 3 d to 7 d. Also, the size and volume of the GV8+ hydrogels may be tailored to match the wound shape and size. Fresh GV8+ hydrogels can also be replaced to the wound bed if required—which may be necessary for chronic wounds. As GV8 is a short peptide, it is likely biodegradable, undergoes proteolysis and rapid clearance by the body.

Figure 25B:
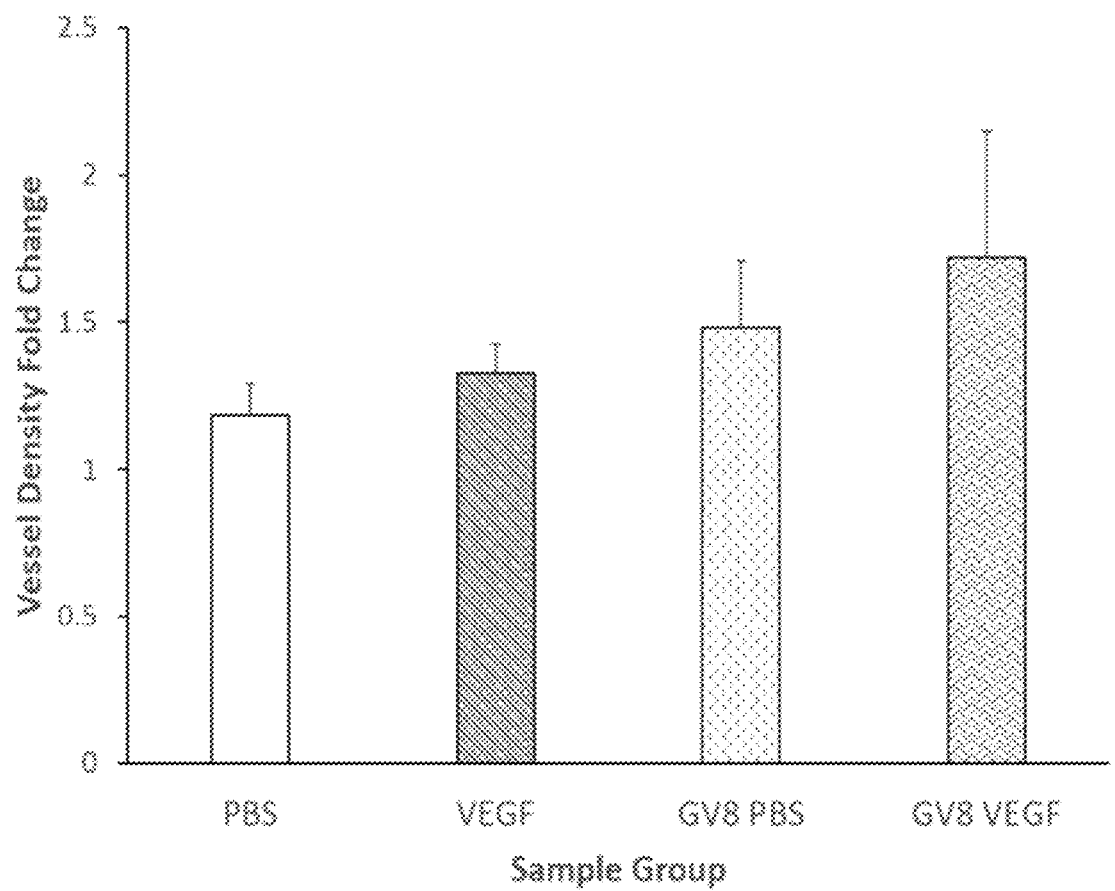
Figure 25C:
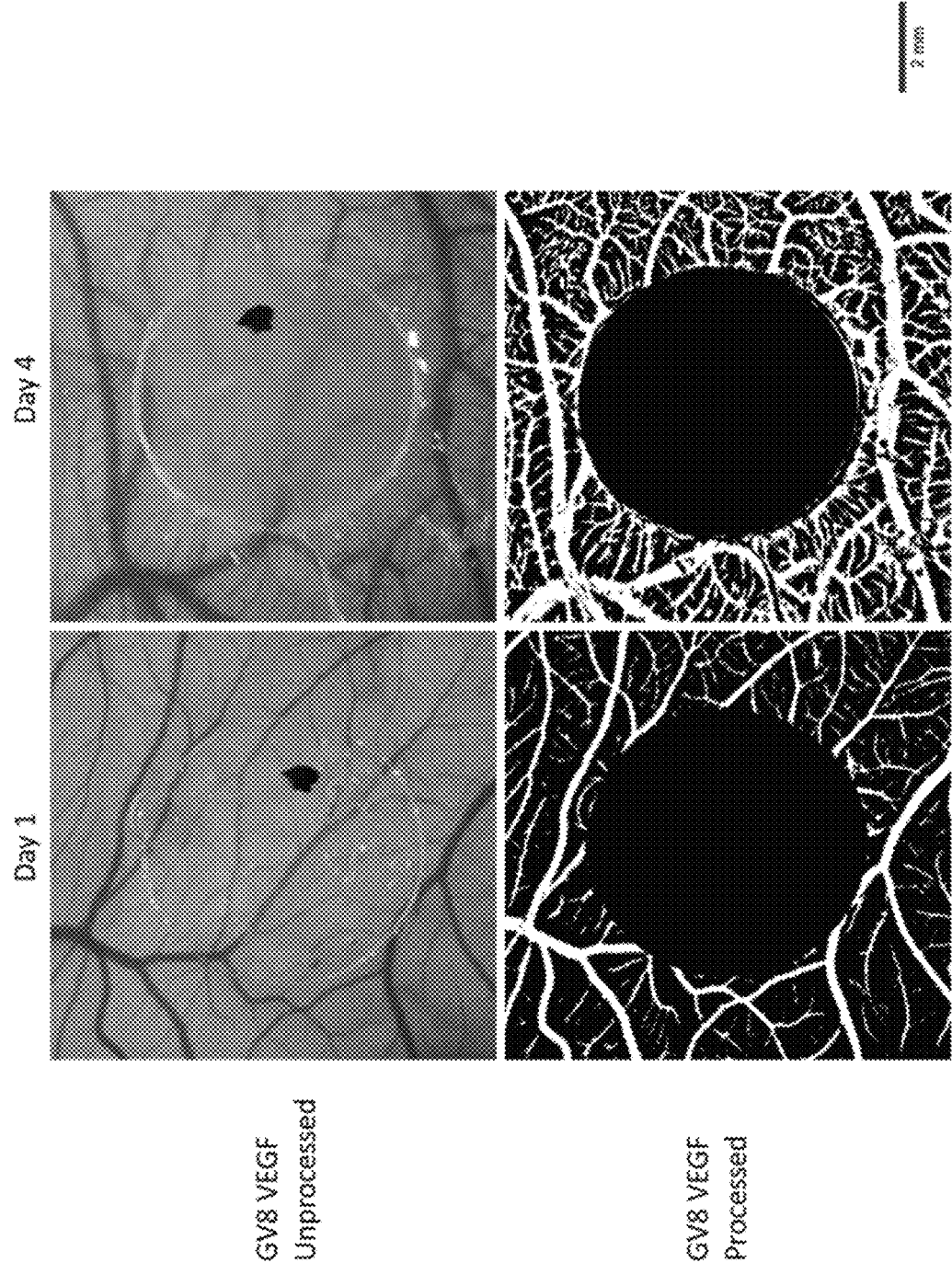

Similarly, GV8+ VEGF hydrogels were demonstrated to support and promote angiogenesis in CAM assays as shown in FIG. 25B. CAM assays were performed over 3 days with GV8+ VEGF hydrogel (FIG. 25B). An observed average of 48% and 72% increase in vessel density was observed after 3 d for the GV8 hydrogel loaded with PBS (i.e. negative control), and VEGF at 6 µg/mL (GV8+ VEGF), respectively. In contrast, the negative control (PBS) and non-encapsulated VEGF hydrogels only showed a 24% and 32% increase in vessel density. However, this observation is not statistically significant due to high variance amongst egg samples. Nonetheless, the increase in the number of vessels and thickening of the vessels can be observed in images of the eggs after 3 d (FIG. 25C), and this presence of angiogenesis and the survival of the embryo for the experimental groups demonstrated that the GV8 hydrogel is safe for ex ovo as well.

2.6 In-Vivo Assay—Delivery of Secretome for Wound Healing

Figure 26:
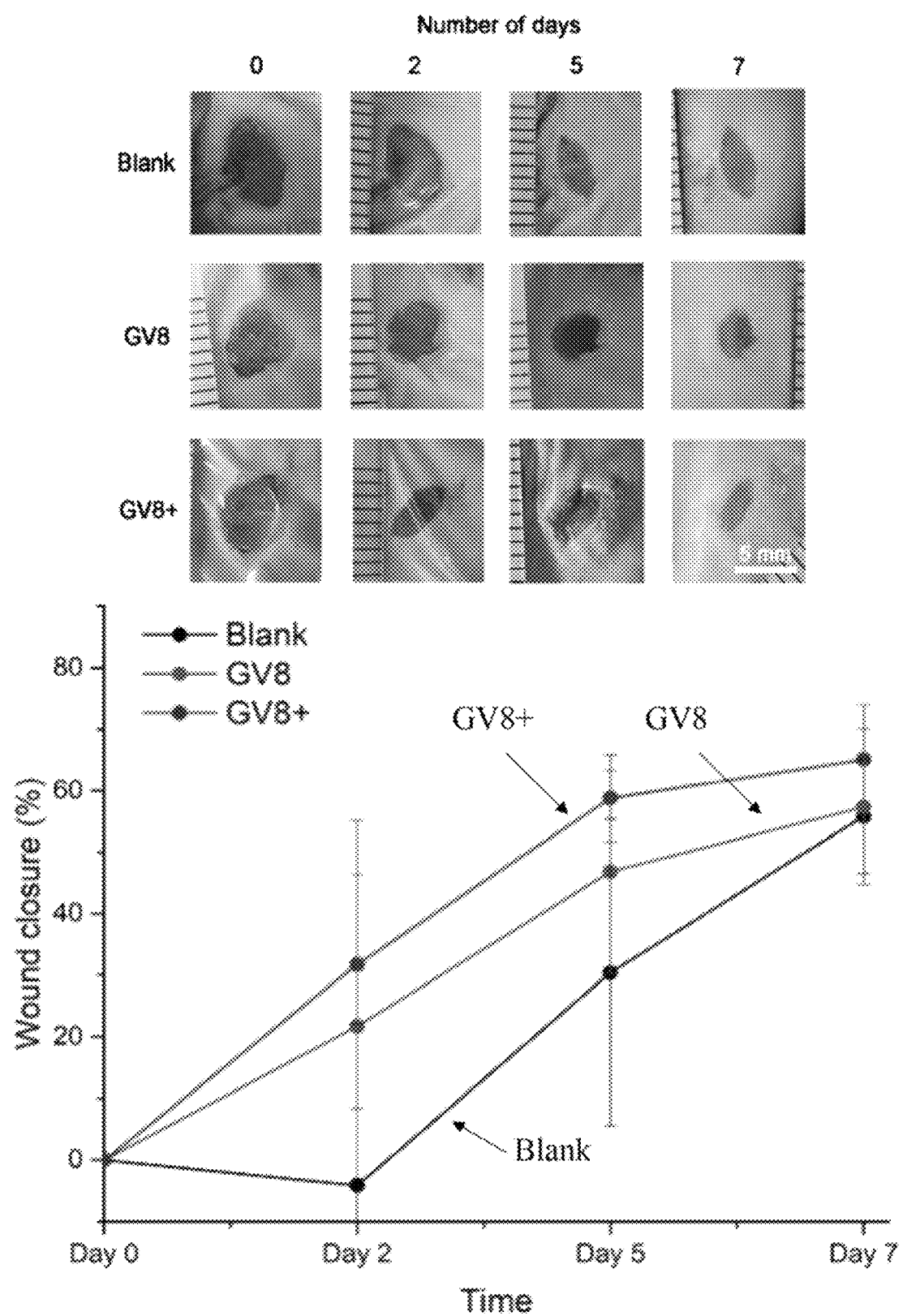
FIG. 26. Topical application of GV8 and GV8+ hydrogels. Both GV8 and GV8+ hydrogels demonstrated the capability to promote and accelerate wound closure on PPARABG mice models.

To investigate the wound healing property of the hydrogels, 30 µL GV8 and GV8+ hydrogels loaded with 200 µg/mL ADMSC secretome were applied to topical puncture wounds on non-diabetic mice models. Representative wounds have been presented in FIG. 26, illustrating the healing of untreated (blank) and treated wounds over 7 d. Wound closure versus time was plotted with n=3 samples, showing that both GV8 and GV8+ hydrogels promoted and accelerated wound closure especially at the initial stages (i.e. 0 d to 2 d) of wound healing, as compared to the control wounds. It was observed that GV8+ hydrogels demonstrated the best wound closure efficacy, achieving 65.1%±8.8% closure at 7 d. In comparison, GV8 hydrogels achieved a 57.4%±12.7% closure, and the untreated wounds a 55.8%±9.3% closure at 7 d. FIG. 26 demonstrated that the in-vivo topical delivery of ADMSC secretome via GV8+ hydrogels facilitates and increases wound healing rate.

2.7 Additional Properties of GV8 Hydrogel

Figure 27A:
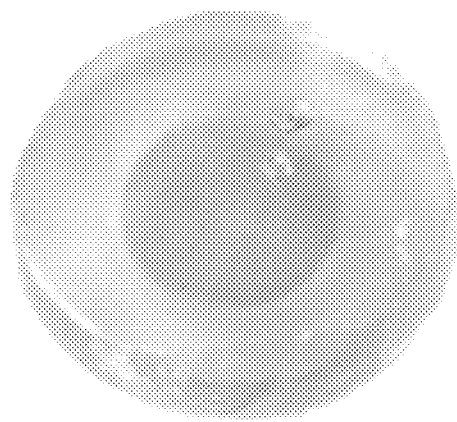
FIG. 27A-27B. Additional features that can be achieved with GV8 peptide hydrogels.

GV8 and GV8+ hydrogels could also be prepared in a concentric manner (FIG. 27A) by forming a new hydrogel layer over the core GV8 hydrogel layer. As shown in FIG. 27A, bromophenol blue dye was added to the GV8 precursor solution to form the core hydrogel. A new layer of the GV8 hydrogel was subsequently formed to encapsulate the core hydrogel layer, which was formed by a precursor solution without the bromophenol blue dye. Some bromophenol blue dye was observed to be released into the external GV8 hydrogel layer, as exposure to solution (in this case, the GV8 precursor solution) facilitated the release of loaded molecules (FIG. 27A), resulting in a hydrogel with a dye concentration gradient. The ability to form concentric gels may provide a greater control of the release of encapsulated active agent within the GV8 hydrogels.

Figure 27B:
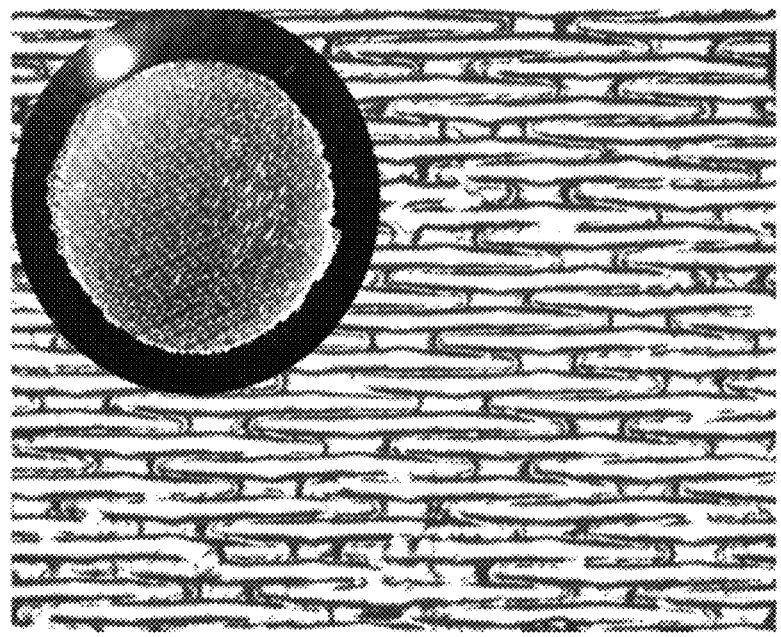
Figure 28A:
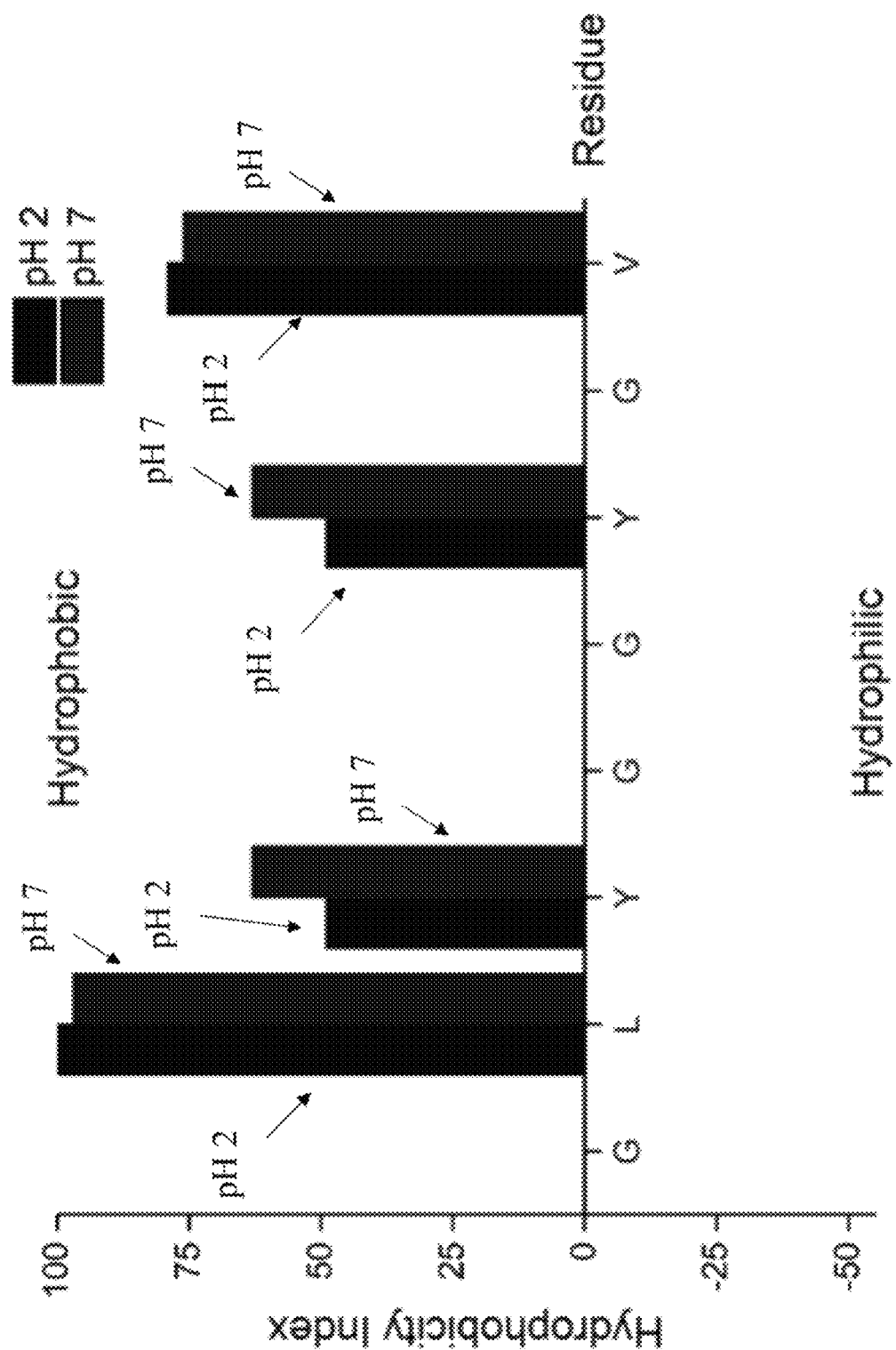
FIG. 28A-28B. Additional properties of the GV8 peptide and GV8 hydrogel.
Figure 28B:
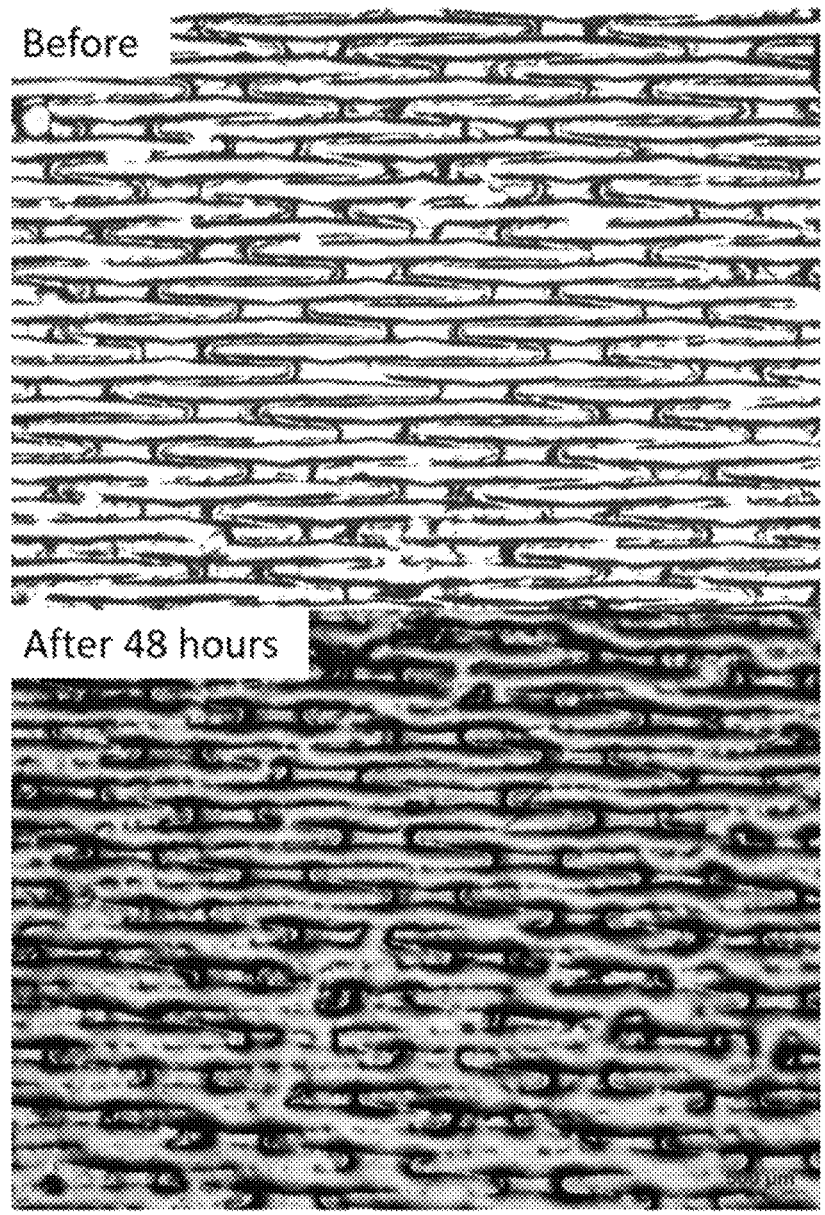

In addition, the surface of the GV8 hydrogels can also be patterned as shown in FIG. 27B. Further, since the GV8 peptide is a non-hydrophilic precursor (FIG. 28A; O. D. Monera et al. *J. Peptide Sci.* 1995, 1, 319; T. J. Sereda et al. *J. Chromatography A.* 1994, 676, 139), the patterned GV8 hydrogels do not swell and deform, and thus patterning was retained for >48 h in solution (FIG. 28B).

3. Advantageous

There are a multitude of advantages with the present invention, including:
  (i) the GV8 peptide is constructed of only natural amino acids and synthesis can be performed by both manual and microwave solid phase peptide synthesis—thus synthesis of the GV8 peptide can be easily scaled up to increase production;
  (ii) the GV8 peptide is a short peptide, which is biocompatible, biodegradable and likely to undergo proteolysis and rapid clearance by the body;
  (iii) as compared to hydrogels (M. K. Nguyen et al. *Prog. Poly. Sci.* 2014, 39, 1235) that require the addition of chemicals and/or additional crosslinking steps for gelation, GV8 hydrogels gelate via a unique transitional change in peptide conformation requiring only ambient temperature and mild conditions. In other words, the GV8 hydrogels gelate in the absence of toxic chemicals and free radical generated by UV exposure. The GV8 hydrogel also has the ability to gelate in buffers with a wide pH range. The simplicity and ease of the GV8 gelation process, which requires a minimum of 5 h, also protects the properties and functionalities of the encapsulated active agent, for example, secretome or VEGF;
  (iv) the GV8 hydrogels exhibit tunable concentration-dependent mechanical properties, whereby the storage modulus (G') of the hydrogels can be adjusted by changing the concentration of the GV8 peptide. GV8 hydrogels have high storage modulus (G'), with about 30 kPa to 40 kPa for a hydrogel of 30 mM concentration. With the addition of secretome, the hydrogel system is further strengthened by about 5 kPa to 10 kPa, depending on secretome concentration. The complementary peptide-protein system of the GV8+ hydrogels increases the stability and structural of the hydrogel both in vitro and in vivo;
  (v) the release properties of GV8 hydrogels may be easily tailored by changing the GV8 peptide concentration. The density of the fibrous network can be increased by increasing GV8 peptide concentration to increase crosslinks and thus slow the diffusion and release of entrapped components from the GV8 hydrogel. Likewise, crosslinks can be decreased by decreasing the peptide concentration to enable entrapped components to diffuse rapidly and be released from the GV8 hydrogel network. Hence, control of the GV8+ hydrogel release profile can be easily achieved, as compared to existing methods which require precise mixing of at least 2 components prior to secretome encapsulation, and may be performed by lesser trained personnel;
  (vi) the incorporation of the active agent (i.e. secretome or VEGF) requires a straightforward and simple procedure of mixing the active agent (i.e. concentrated secretome or VEGF) with the GV8 peptide solution prior to gelation, as compared to lengthy and uncontrollable adsorption methods described in the Background section. The active agent (i.e. secretome or VEGF) may also be protected from degradation due to ambient gelation temperature and a relatively short gelation duration (hence incorporation time), as compared to methods which require at least a 24 h adsorption or incorporation process under harsh conditions, for example, UV exposure. In the present invention, the concentration of the active agent (i.e. secretome) can be controlled, and a high secretome concentration of up to 200 µg/µL has been shown to be successfully loaded into the GV8+ hydrogels. Similarly, the concentration of the active agent, VEGF can be controlled, and VEGF concentration of 6 µg/µL was successfully loaded into the GV8+ VEGF hydrogels;
  (vii) owing to its stiffness (i.e. high storage modulus, G'), the GV8 and GV8+ hydrogels can be patterned by simply allowing the solution to gelate in a mould or over a patterned surface. Since the GV8 peptide precursor is non-hydrophilic (i.e. hydrophobic), GV8 hydrogels formed will not swell and deform through the absorption of water. This allows the GV8 and GV8+ hydrogels to retain their patterning, which remains stable for more than 48 h in solution. Further, microchannels may be imprinted onto the surface of the GV8 and GV8+ hydrogels, which may serve as contact guides for cells during cell migration (C. Y. Tay et al. *Small* 2011, 7, 1361; Y. Hwang et al. *Poly. (Basel)* 2017, 9, 580; I. Lee et al. *PLoS One.* 2018, 13, e0201418; A. Marmaras et al. *Soft Matter* 2012, 8, 6922); and
  (viii) fluorescence labels may be tagged to an active agent (e.g. fluorescence-tagged secretome or VEGF) during the synthesis of GV8, GV8+, GV8+ VEGF hydrogels, which may facilitate the design of novel pharmaceutical platforms to investigate the mechanics of active agent delivery and/or therapies.

Collectively, the aforementioned advantages associated with the GV8, GV8+, GV8+ VEGF hydrogels provides an improved hydrogel, in particular, a hydrogel with the ability to encapsulate and deliver active agent(s) (i.e. secretome or VEGF) for wound healing.

All documents cited herein, are hereby incorporated by reference in their entirety. The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group. Further embodiments of the invention will become apparent from the following claims.

The invention claimed is:

1. An isolated peptide consisting of the amino acid sequence:

$$(GX_1Z_1GGZ_2GB)_n (X_2)_m (GX_1Z_1GGZ_2GB)_o \quad (\text{SEQ ID NO: 3})$$

wherein each B is independently valine (V) or isoleucine (I);

each $X_1$ independently is an aliphatic amino acid, preferably leucine (L);

each $Z_1$, $Z_2$ is independently an aromatic amino acid, preferably tyrosine (Y);

$X_2$ is any amino acid; and m is 0 or an integer from 1 to 10; n and o are independently 0 or an integer selected from 1, 2 or 3, provided that n+o is at least 1.

2. The isolated peptide of claim 1, wherein
(i) wherein the isolated peptide is at least partially in a $3_{10}$ helix conformation in an aqueous solution; and/or
(ii) m is 0; and/or
(iii) o is 0; and/or
(iv) the isolated peptide consists of the amino acid sequence $(GX_1Z_1GGZ_2GV)_n$ (SEQ ID NO: 12) or $(GX_1Z_1GGZ_2GI)_n$ (SEQ ID NO: 13); and/or
(v) wherein the isolated peptide is up to 30 amino acids in length, up to 25 amino acids in length, up to 20 amino acids in length, up to 16 amino acids in length, up to 10 amino acids in length, and up to 8 amino acids in length; and/or
(vi) the isolated peptide consists of the amino acid sequence $(GLYGGYGV)_n$ (SEQ ID NO: 5) or GLYGGYGV (SEQ ID NO: 1); and/or
(vii) the isolated peptide consists of the amino acid sequence $(GLYGGYGI)_n$ (SEQ ID NO: 6) or GLYGGYGI (SEQ ID NO: 2).

3. The isolated peptide of claim 1,
wherein the isolated peptide is further acetylated at the N-terminus, and amidated at the C-terminus.

4. A composition or material for delivery of an active agent, the composition or material comprising a hydrogel, wherein the hydrogel comprises:
(i) one or more isolated peptides according to claim 1,
(ii) an active agent encapsulated in the hydrogel, and wherein the isolated peptides in the hydrogel are at least partially in a β-sheet conformation.

5. The composition or material of claim 4,
wherein the active agent is selected from the group comprising: complete cells, cellular components, proteins, polypeptides, carbohydrates, nucleic acids, lipids, small chemical compounds, nanoparticles, and combinations thereof.

6. The composition or material of claim 4,
wherein the active agent is a pharmaceutical or diagnostic agent.

7. The composition or material of claim 6,
wherein the pharmaceutical or diagnostic agent is secretome derived from mesenchymal stem cells (MSC) and/or vascular endothelial growth factor (VEGF).

8. The composition or material of claim 4,
wherein the hydrogel is a pharmaceutical or diagnostic formulation for administration to a subject.

9. The composition or material of claim 4,
wherein the composition or material is in the form of any one selected from the group of: a fibre, a filament, a film, a nano fibre, or a colloidal solution.

10. The composition or material of claim 4,
wherein the pH of the composition or material is >4.0 and <8.0.

11. A multi-layered composition or material for delivery of an active agent, the multi-layered composition or material comprising a multi-layered hydrogel, wherein the hydrogel comprises:
   (i) one or more isolated peptides according to claim 1,
   (ii) an active agent encapsulated in the multi-layered hydrogel, and
      wherein the isolated peptides in the multi-layered hydrogel are at least partially in a β-sheet conformation.

12. A method for the encapsulation of an active agent in a hydrogel, the method comprising:
   (i) providing an aqueous solution of hydrogel-forming peptides, wherein the hydrogel-forming peptides comprises one or more isolated peptides, the one or more isolated peptides consisting the amino acid sequence:

$$(GX_1Z_1GGZ_2GB)_n(X_2)_m(GX_1Z_1GGZ_2GB)_o \quad \text{(SEQ ID NO: 3)}$$

wherein
      each B is independently valine (V) or isoleucine (I);
      each $X_1$ independently is an aliphatic amino acid, preferably leucine (L);
      each $Z_1$, $Z_2$ is independently an aromatic amino acid, preferably tyrosine (Y);
      $X_2$ is any amino acid;
      m is 0 or an integer from 1 to 10;
      n and o are independently 0 or an integer selected from 1, 2 or 3, provided that n+o is at least 1;
   (ii) combining the aqueous solution of the hydrogel-forming peptides with a solution of an active agent; and
   (iii) inducing formation of the hydrogel, wherein the isolated peptides in the hydrogel are at least partially in a β-sheet conformation.

13. The method of claim 12,
wherein the solution of the active agent is buffered such that the combination of the solution of the active agent with the aqueous solution of the hydrogel-forming peptides has a pH of >4.0 and <8.0.

14. The method of claim 12,
wherein inducing the formation of the hydrogel is at a temperature of >15° C. and <30° C.

15. The method of claim 12,
wherein inducing the formation of the hydrogel is at a time of >2 h and <50 h.

16. The method of claim 12,
wherein a concentration of the hydrogel-forming peptides in the combined aqueous solution of the hydrogel-forming peptides and the active agent is >10 mM and <80 mM.

17. The method of claim 12,
wherein a concentration of the active agent in the combined aqueous solution of the hydrogel-forming peptides and the active agent is >5 μg/mL and <500 μg/mL.

18. A method for treating or diagnosing a tissue injury in a human subject in need thereof, comprising:
   (i) administering a composition or material comprising a hydrogel to the subject, wherein the hydrogel comprises:
      a. hydrogel-forming peptides comprising one or more isolated peptides, the isolated peptides consisting the amino acid sequence:

$$(GX_1Z_1GGZ_2GB)_n(X_2)_m(GX_1Z_1GGZ_2GB)_o \quad \text{(SEQ ID NO: 3)}$$

wherein
      each B is independently valine (V) or isoleucine (I);
      each $X_1$ independently is an aliphatic amino acid, preferably leucine (L);
      each $Z_1$, $Z_2$ is independently an aromatic amino acid, preferably tyrosine (Y);
      $X_2$ is any amino acid;
      m is 0 or an integer from 1 to 10;
      n and o are independently 0 or an integer selected from 1, 2 or 3, provided that n+o is at least 1;
      wherein the isolated peptides in the hydrogel are at least partially in a β-sheet conformation, and
      b. a pharmaceutical or diagnostic agent, wherein the pharmaceutical or diagnostic agent is encapsulated in the hydrogel.

19. The method of claim 18,
wherein the pharmaceutical or diagnostic agent is secretome derived from MSCs, and
wherein the administration of the hydrogel is topical, and secretome is released from the hydrogel in a controlled manner.

20. The method of claim 18,
wherein the pharmaceutical or diagnostic agent is VEGF, and
wherein the administration of the hydrogel is topical, and VEGF is released from the hydrogel in a controlled manner.

* * * * *

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Suckerin-inspired derivative

<400> SEQUENCE: 1

Gly Leu Tyr Gly Gly Tyr Gly Val
1               5

<210> SEQ ID NO 2
<211> LENGTH: 8
<212> TYPE: PRT
<213> ORGANISM: Artificial Sequence
<220> FEATURE:
<223> OTHER INFORMATION: Suckerin-inspired derivative

<400> SEQUENCE: 2

Gly Leu Tyr Gly Gly Tyr Gly Ile
1               5

<210> SEQ ID NO 3
<211> LENGTH: 58
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2,10,18,36,44,52
<223> OTHER INFORMATION: Xaa = aliphatic amino acid, preferably leucine
      (L)
<220> FEATURE:
<221> NAME/KEY: VARIANT
<222> LOCATION: 3,11,19,37,45,53
<223> OTHER INFORMATION: Xaa = aromatic amino acid, preferably tyrosine
      (Y)
<220> FEATURE:
<221> NAME/KEY: VARIANT
<222> LOCATION: 6,14,22,40, 48, 56
<223> OTHER INFORMATION: Xaa = aromatic amino acid, preferably tyrosine
      (Y)
<220> FEATURE:
<221> NAME/KEY: VARIANT
<222> LOCATION: 8,16,24,42,50,58
<223> OTHER INFORMATION: Xaa = valine (V) or isoleucine (I)
<220> FEATURE:
<221> NAME/KEY: VARIANT
<222> LOCATION: (25)...(34)
<223> OTHER INFORMATION: Xaa = any amino acid
<220> FEATURE:
<221> NAME/KEY: VARIANT
<222> LOCATION: (9)...(24)
```

```
<223> OTHER INFORMATION: any one or all of amino acids 9-24 can either
      be present or absent.
<220> FEATURE:
<221> NAME/KEY: VARIANT
<222> LOCATION: (25)...(34)
<223> OTHER INFORMATION: any one or all of amino acids 25-34 can either
      be present or absent.
<220> FEATURE:
<221> NAME/KEY: VARIANT
<222> LOCATION: (43)...(58)
<223> OTHER INFORMATION: any one or all of amino acids 43-58 can either
      be present or absent.

<400> SEQUENCE: 3

Gly Xaa Xaa Gly Gly Xaa Gly Xaa Gly Xaa Xaa Gly Gly Xaa Gly Xaa
1               5                   10                  15

Gly Xaa Xaa Gly Gly Xaa Gly Xaa Xaa Xaa Xaa Xaa Xaa Xaa Xaa
            20                  25                  30

Xaa Xaa Gly Xaa Xaa Gly Gly Xaa Gly Xaa Gly Xaa Xaa Gly Gly Xaa
                35                  40                  45

Gly Xaa Gly Xaa Xaa Gly Gly Xaa Gly Xaa
        50                  55

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2,10,18
<223> OTHER INFORMATION: Xaa = aliphatic amino acid, preferably leucine
      (L)
<220> FEATURE:
<221> NAME/KEY: VARIANT
<222> LOCATION: 3,11,19
<223> OTHER INFORMATION: Xaa = aromatic amino acid, preferably tyrosine
      (Y)
<220> FEATURE:
<221> NAME/KEY: VARIANT
<222> LOCATION: 6,14,22
<223> OTHER INFORMATION: Xaa = aromatic amino acid, preferably tyrosine
      (Y)
<220> FEATURE:
<221> NAME/KEY: VARIANT
<222> LOCATION: 8,16,24
<223> OTHER INFORMATION: Xaa = valine (V) or isoleucine (I)

<400> SEQUENCE: 4

Gly Xaa Xaa Gly Gly Xaa Gly Xaa Gly Xaa Xaa Gly Gly Xaa Gly Xaa
1               5                   10                  15

Gly Xaa Xaa Gly Gly Xaa Gly Xaa
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (9)...(24)
<223> OTHER INFORMATION: any one or all of amino acids 9-24 can either
      be present or absent.

<400> SEQUENCE: 5

Gly Leu Tyr Gly Gly Tyr Gly Val Gly Leu Tyr Gly Gly Tyr Gly Val
1               5                   10                  15
```

```
Gly Leu Tyr Gly Gly Tyr Gly Val
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (9)...(24)
<223> OTHER INFORMATION: any one or all of amino acids 9-24 can either
      be present or absent.

<400> SEQUENCE: 6

Gly Leu Tyr Gly Gly Tyr Gly Ile Gly Leu Tyr Gly Gly Tyr Gly Ile
1               5                   10                  15

Gly Leu Tyr Gly Gly Tyr Gly Ile
            20

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 1
<220> FEATURE:
<221> NAME/KEY: AMIDATION
<222> LOCATION: 8

<400> SEQUENCE: 7

Gly Leu Tyr Gly Gly Tyr Gly Val
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 1
<220> FEATURE:
<221> NAME/KEY: AMIDATION
<222> LOCATION: 8

<400> SEQUENCE: 8

Gly Leu Tyr Gly Gly Tyr Gly Ile
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 1
<220> FEATURE:
<221> NAME/KEY: VARIANT
<222> LOCATION: 2
<223> OTHER INFORMATION: Xaa = aliphatic amino acid, preferable leucine
      (L)
<220> FEATURE:
```

-continued

```
<221> NAME/KEY: VARIANT
<222> LOCATION: 3,6
<223> OTHER INFORMATION: Xaa = aromatic amino acid, preferably tyrosine
      (Y)
<220> FEATURE:
<221> NAME/KEY: AMIDATION
<222> LOCATION: 8

<400> SEQUENCE: 9

Gly Xaa Xaa Gly Gly Xaa Gly Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 1
<220> FEATURE:
<221> NAME/KEY: VARIANT
<222> LOCATION: 2
<223> OTHER INFORMATION: Xaa = aliphatic amino acid, preferably leucine
      (L)
<220> FEATURE:
<221> NAME/KEY: VARIANT
<222> LOCATION: 3,6
<223> OTHER INFORMATION: Xaa = aromatic amino acid, preferable tyrosine
      (Y)
<220> FEATURE:
<221> NAME/KEY: AMIDATION
<222> LOCATION: 8

<400> SEQUENCE: 10

Gly Xaa Xaa Gly Gly Xaa Gly Val
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: ACETYLATION
<222> LOCATION: 1
<220> FEATURE:
<221> NAME/KEY: VARIANT
<222> LOCATION: 8
<223> OTHER INFORMATION: Xaa = V, L, A, F, S, and K
<220> FEATURE:
<221> NAME/KEY: AMIDATION
<222> LOCATION: 8

<400> SEQUENCE: 11

Gly Leu Tyr Gly Gly Tyr Gly Xaa
1               5

<210> SEQ ID NO 12
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2,10,18
<223> OTHER INFORMATION: Xaa = aliphatic amino acid, preferably lysine
      (L)
<220> FEATURE:
<221> NAME/KEY: VARIANT
```

```
<222> LOCATION: 3,6,11,14,19, 22
<223> OTHER INFORMATION: Xaa = aromatic amino acid preferable tyrosine
      (Y)
<220> FEATURE:
<221> NAME/KEY: VARIANT
<222> LOCATION: (9)...(24)
<223> OTHER INFORMATION: any one or all of amino acids 9-24 can either
      be present or absent.

<400> SEQUENCE: 12

Gly Xaa Xaa Gly Gly Xaa Gly Val Gly Xaa Xaa Gly Gly Xaa Gly Val
1               5                   10                  15

Gly Xaa Xaa Gly Gly Xaa Gly Val
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2,10,18
<223> OTHER INFORMATION: Xaa = aliphatic amino acid, preferable lysine
      (L)
<220> FEATURE:
<221> NAME/KEY: VARIANT
<222> LOCATION: 3,6,11,14,19,22
<223> OTHER INFORMATION: Xaa = aromatic amino acid, preferable tyrosine
      (Y)
<220> FEATURE:
<221> NAME/KEY: VARIANT
<222> LOCATION: (9)...(24)
<223> OTHER INFORMATION: any one or all of amino acids 9-24 can either
      be present or absent.

<400> SEQUENCE: 13

Gly Xaa Xaa Gly Gly Xaa Gly Ile Gly Xaa Xaa Gly Gly Xaa Gly Ile
1               5                   10                  15

Gly Xaa Xaa Gly Gly Xaa Gly Ile
            20
```